US007582442B2

(12) United States Patent
Shayman et al.

(10) Patent No.: US 7,582,442 B2
(45) Date of Patent: *Sep. 1, 2009

(54) METHODS AND COMPOSITIONS FOR USING ALEVEOLAR MACROPHAGE PHOSPHOLIPASE A2

(75) Inventors: James A. Shayman, Ann Arbor, MI (US); Akira Abe, Ann Arbor, MI (US); Miki Hiraoka, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 328 days.

This patent is subject to a terminal disclaimer.

(21) Appl. No.: 11/080,257

(22) Filed: Mar. 15, 2005

(65) Prior Publication Data

US 2006/0008455 A1   Jan. 12, 2006

Related U.S. Application Data

(60) Provisional application No. 60/553,641, filed on Mar. 16, 2004.

(51) Int. Cl.
  *C12Q 1/42* (2006.01)
(52) U.S. Cl. .................. 435/21; 435/198; 424/94.6
(58) Field of Classification Search ............... 424/94.6; 435/198, 21
  See application file for complete search history.

(56) References Cited

U.S. PATENT DOCUMENTS

| 4,367,110 | A | 1/1983 | Yoshikawa |
| 4,452,901 | A | 6/1984 | Gordon et al. |
| 4,861,719 | A | 8/1989 | Miller |
| 4,873,191 | A | 10/1989 | Wagner et al. |
| 5,139,941 | A | 8/1992 | Muzyczka et al. |
| 5,156,950 | A | 10/1992 | Akino et al. |
| 5,252,479 | A | 10/1993 | Srivastava |
| 5,328,688 | A | 7/1994 | Roizman |
| 5,366,861 | A | 11/1994 | Hosoda et al. |
| 5,474,935 | A | 12/1995 | Chatterjee et al. |
| 5,585,362 | A | 12/1996 | Wilson et al. |
| 5,622,856 | A | 4/1997 | Natsoulis |
| 5,658,776 | A | 8/1997 | Flotte et al. |
| 5,661,033 | A | 8/1997 | Ho et al. |
| 5,670,328 | A | 9/1997 | Inoue et al. |
| 5,670,488 | A | 9/1997 | Gregory et al. |
| 5,686,278 | A | 11/1997 | Williams et al. |
| 5,693,509 | A | 12/1997 | Cotten et al. |
| 5,707,618 | A | 1/1998 | Armentano et al. |
| 5,770,414 | A | 6/1998 | Gage et al. |
| 5,773,289 | A | 6/1998 | Samulski et al. |
| 5,789,390 | A | 8/1998 | Descamps et al. |
| 5,824,544 | A | 10/1998 | Armentano et al. |
| 5,830,725 | A | 11/1998 | Nolan et al. |
| 5,830,727 | A | 11/1998 | Wang et al. |
| 5,834,441 | A | 11/1998 | Philip et al. |
| 5,849,571 | A | 12/1998 | Glorioso et al. |
| 5,851,521 | A | 12/1998 | Branellec et al. |
| 5,856,152 | A | 1/1999 | Wilson et al. |
| 5,856,196 | A | 1/1999 | Alvarez et al. |
| 5,863,541 | A | 1/1999 | Samulski et al. |
| 5,879,934 | A | 3/1999 | DeLuca |
| 5,888,502 | A | 3/1999 | Guber et al. |
| 5,916,911 | A | 6/1999 | Shayman et al. |
| 5,945,442 | A | 8/1999 | Shayman et al. |
| 5,952,370 | A | 9/1999 | Shayman et al. |
| 6,019,965 | A | 2/2000 | Dunn et al. |
| 6,030,995 | A | 2/2000 | Shayman et al. |
| 6,040,332 | A | 3/2000 | Shayman et al. |
| 6,051,598 | A | 4/2000 | Shayman et al. |
| 6,098,631 | A | 8/2000 | Holoshitz et al. |
| 6,255,336 | B1 | 7/2001 | Shayman et al. |
| 6,518,259 | B1 | 2/2003 | Holoshitz et al. |
| 6,569,889 | B2 | 5/2003 | Shayman et al. |

FOREIGN PATENT DOCUMENTS

| EP | 0 273 085 | 7/1988 |
| EP | 0 367 566 | 5/1990 |
| WO | WO-91/18982 | 12/1991 |

OTHER PUBLICATIONS

Abe et al., J. Biol. Chem., 271(24):14383-14389 (1996).
Abe et al., J. Biol. Chem., 273(14):8467-8474 (1998).
Bhattacharyya et al., J. Clin. Invest., 55:914-920 (1975).
Benvenisty et al., Proc. Natl. Acad. Sci. USA, 83:9551-9555 (1986).
Brinster et al., Proc. Natl. Acad. Sci. USA, 82:4438-4442 (1985).
Chen et al., J. Biol. Chem., 275(37):28421-28427 (2000).
Chen et al:, Mol. Cell Biol., 7(8):2745-2752 (1987).
Coffey et al., J. Biol. Chem., 267(1):570-576 (1992).
Coffey et al., J. Immunol., 165(7):3592-3598 (2000).
Dubensky et al., Proc. Natl. Acad. Sci. USA, 81:7529-7533 (1984).
Engelhard et al., Proc. Natl. Acad. Sci. USA, 91:3224-3227. (1994).

(Continued)

*Primary Examiner*—Tekchand Saidha
(74) *Attorney, Agent, or Firm*—Marshall, Gerstein & Borun LLP

(57) ABSTRACT

The present invention is directed to methods and compositions for improving pulmonary surfactant catabolism. More specifically, the specification describes methods and compositions for making and using a lysosomal phospholipase A2 in methods for the diagnosis, and treatment of disorders of phospholipid catabolism such as pulmonary alveolar proteinosis.

3 Claims, 12 Drawing Sheets

OTHER PUBLICATIONS

Fechheimer et al., Proc. Natl. Acad. Sci. USA, 84:8463-8467 (1987).
Ferkol et al., FASEB J., 7:1081-1091 (1993).
Fisher et al., Am. J. Physiol. Lung Cell. Mol. Physiol., 280:L748-L754 (2001).
Fisher et al., Biochem. J., 288:407-411 (1992).
Fraley et al., Proc. Natl. Acad. Sci. USA, 76(7):3348-3352 (1979).
Genbank Accession No. AY072914.
Genbank Accession No. AY179884.
Genbank Accession No. AY490816.
Genbank Accession No. P97570.
Gopal, Mol. Cell. Biol., 5(5):1188-1190 (1985).
Harland et al., J. Cell Biol., 101:1094-1099 (1985).
Hiraoka et al., J. Biol. Chem., 277(12):10090-10099 (2002).
Huffman et al., J. Clin. Invest., 97(3):649-655 (1996).
Kato et al., J. Biol. Chem., 266(6):3361-3364 (1991).
Kim et al., Am. J. Physiol., 274(5 Pt 1):L750-L761 (1998).
Okayama et al., Mol. Cell. Biol., 3(2):280-289 (1983).
Paine et al., J. Immunol., 164:2602-2609 (2000).
Perales et al., Proc. Natl. Acad. Sci. USA, 91:4086-4090 (1994).
Potter et al., Proc. Natl. Acad. Sci. USA, 81:7161-7165 (1984).
Radler et al., Science, 275:810-814 (1997).
Reasor et al., Exp. Biol. Med., 226(9):825-830 (2001).
Rippe et al., Mol. Cell. Biol., 10(2):689-695 (1990).
Rosenwald et al., J. Lipid. Res., 35:1232-1240 (1994).
Tur-Kaspa et al., Mol. Cell. Biol., 6(2):716-718 (1986).
Wagner et al., Proc. Natl. Acad. Sci. USA, 87:3410-3414. (1990).
Wang et al., J. Biol. Chem., 278(27):25179-25190 (2003).
Wu et al., J. Biol. Chem., 262(10):4429-4432 (1987).
Yang et al., Proc. Natl. Acad. Sci. USA, 87:9568-9572 (1990).
deMello et al., *Pediatr. Pathol. Mol. Med.*, 20(5):413-432 (2001).
Ikegami et al., *Am. J. Physiol.*, 270(4 Pt 1):L650-L658 (1996).
King, *J. Appl. Physiol.*, 53(1):1-8 (1982).
Mo et al., *FEBS Lett.*, 555(2):192-198 (2003).
Montenez et al., *Eur. J. Pharmacol.*, 314(1-2):215-227 (1996).
Reasor et al.,*Proc. Soc. Exp. Biol. Med.*, 211(4):346-352 (1996).
Reasor et al., *Toxicol. Appl. Pharmacol.*, 97(1):124-133 (1989).
Shelley et al., *Am. J. Obstet. Gynecol.*, 144(2):224-228 (1982).
Sueishi et al., *Biochim. Biophys. Acta*, 665(3):442-453 (1981).
Valko et al., *J. Pharm. Sci.*, 89(8):1085-1096 (2000).
van Bambeke et al., *Eur. J. Pharmacol.*, 314(1-2):203-214 (1996).
Winstead et al., *Biochim. Biophys. Acta*, 1488(1-2):28-39 (2000).

vehicle                    15 μM amiodarone

METHODS AND COMPOSITIONS FOR USING ALEVEOLAR MACROPHAGE PHOSPHOLIPASE A2

The present application claims the benefit of priority of U.S. Provisional Application No. 60/553,641, which was filed Mar. 16, 2004. The entire text of the aforementioned application is specifically incorporated herein by reference.

This invention was made with government support under grant number DK 55823 awarded by National Institutes of Health. The government has certain rights in the invention.

BACKGROUND

1. Field of the Invention

The present invention is generally directed to methods and compositions for increasing phospholipid catabolism and/or the treatment of lung disease.

2. Background of the Related Art

Lung surfactant is the surface-active agent comprised of phospholipids and proteins that lines pulmonary alveolae. Surfactant stabilizes the alveolar volume by reducing surface tension. This complex consists of approximately 90% phospholipids and 5-10% protein (King, J. Appl. Physiol. Exercise Physiol. 53, 1-8 1982). The protein fraction of the surfactant is composed of nonserum and serum proteins. The major surfactant associated protein is reportedly a 35,000 dalton nonserum, sialoglycoprotein (Bhattacharyya et al., J. Clin. Invest. 55, 914-920, 1975; Shelly et al., Am. J. Obstet. Gynecol. 144, 224-228, 1982; Sueishin and Benson, Biochem. Biophys. Acta 665, 442-453, 1981). The phospholipid component of pulmonary surfactant is largely in the form of dipalmitoylphosphatidylcholine.

Pulmonary alveolar proteinosis (PAP) is a rare diffuse lung disease that is characterized by the alveolar and interstitial accumulation of a periodic acid-Schiff stain-positive phospholipoprotein derived from the pulmonary surfactant. This disorder is known to occur in primary and secondary forms. Primary PAP is idiopathic. However, PAP also may manifest as a secondary disorder that is associated with hematologic malignancies, such as chronic myeloid leukemia and lymphomas. In addition PAP has been documented in association with occupational exposure to mineral dusts and fumes. Mineral dust exposures associated with PAP include aluminum dust, titanium dioxide, cement dust, fibrous insulation material, and nitrogen dioxide, as reported in several studies. PAP also is thought to result in association with infections, including infection by Nocardia, *Mycobacterium tuberculosis*, non-tuberculous mycobacteria, cytomegalovirus, and fungal infections, such as histoplasmosis and cryptococcosis. PAP also has been described by Ruben and Talamo in patients with AIDS, including AIDS patients with coincident Pneumocystis pneumonia infection. Others have suggested that PAP may be a congenital in origin, resulting from a lysinuric protein intolerance (according to Parto et al) or deficiency of surfactant protein B.

Congenital alveolar proteinosis (CAP) is a specific and severe form of alveolar proteinosis in which the predominant symptoms, which occur shortly after birth, include neonatal respiratory distress, dyspnea, tachypnea, diminished exercise tolerance, feeding difficulty, failure to thrive, and loss of weight. In neonatal respiratory distress, the patient with CAP presents with progressive respiratory failure and marked hypoxemia shortly after birth. In the absence of therapeutic intervention CAP has a 100% mortality rate. To date, the only effective therapeutic intervention has been whole lung transplantation in these patients. However, even with this drastic intervention, remission has been observed.

Thus, the etiology of PAP is varied and the underlying causes of the disorder remain poorly understood. However, in all cases there is an abnormal accumulation of phospholipids in lung tissue. The symptoms of PAP are generally those associated with a syndrome known as phospholipidosis, a generalized condition observed in both animals and humans that is characterized by the appearance of concentric lamellar bodies within cells and the intracellular accumulation of phospholipids. Phospholipidosis is an acquired condition observed in patients treated with a variety of commonly prescribed cationic amphiphilic drugs (CADs) that include amiodarone, gentamicin, fluoxetine, and chloroquine. Phospholipidosis is thought to arise by the inhibition of one or more acidic lysosomal phospholipases. However, the failure to identify the lysosomal phospholipase that is the target for drug-induced phospholipidosis has hindered the understanding of the pathogenesis and significance of this condition.

Treatment of PAP involves periodic therapeutic bronchioalveolar lavages. In such therapy, a periodic whole-lung lavage is administered in which the excessive phospholipids are washed from the lung. This therapy requires hospitalization and specially trained physicians. In severe cases, lung transplantation is required. The current therapies are often inadequate because spontaneous remission, as well as, progressive respiratory failure is often observed. In addition, these therapeutic interventions have attendant complications related to secondary infections. The requirement for such intervention in CAD-induced phospholipidosis greatly diminishes the therapeutic utility of CADs.

Therefore, there remains a need for a better understanding of the causes of phospholipid catabolism disorders and for the identification of new therapeutic interventions for such disorders.

SUMMARY OF THE INVENTION

The present invention is directed to phospholipid catabolism and/or the treatment of lung disease. More specifically, in one aspect, the present invention describes a method of increasing degradation of glycerophospholipids in pulmonary surfactant comprising contacting a sample containing pulmonary surfactant with a composition comprising a lysosomal phospholipase A2 (LPLA2) protein having an amino acid sequence of SEQ ID NO:2, or a biologically active fragment or variant of a protein having an amino acid sequence of SEQ ID NO:2. Preferably, the sequence is from a human source. In other embodiments, the sequence is from another mammalian source such as a bovine or a murine sequence. As an alternative to SEQ ID NO:2, SEQ ID NO:11 or SEQ ID NO:13 also could be used. In certain embodiments, the pulmonary surfactant is a component of an alveolar macrophage. In particular embodiments, the alveolar macrophage is located in vitro, in other embodiments, the alveolar macrophage is located in vivo. In some examples, the contacting comprises administering a composition comprising the lysosomal phospholipase A2 protein in combination with a pharmaceutically acceptable carrier. In particular embodiments, the composition is formulated as an inhalant.

Another aspect of the invention contemplates a method of increasing the in vivo breakdown of pulmonary surfactant comprising administering to the mammal a composition comprising a LPLA2 protein having an amino acid sequence of SEQ ID NO:2, or a biologically active fragment or variant of a protein derived from the amino acid sequence of SEQ ID NO:2. Alternatively, similar methods may use compositions comprising SEQ ID NO:11 or SEQ ID NO:13 or fragments or variants thereof. In specific circumstances, the breakdown of pulmonary surfactant comprises increasing the degradation of the phospholipid component of the pulmonary surfactant. The phospholipid is typically any phospholipid known to those of skill in the art. In specific embodiments, the phospholipid component is selected from the group consisting of phosphatidylcholine (PC), phosphatidylethanolamine (PE), phosphatidylserine (PS), phosphatidylinositol (PI), phosphatidylglycerol (PG), cardiolipin (CL), a sphingolipid, sphingomyelin (SM), and phosphatidic acid (PA). In particular embodiments, the phospholipid component is dipalmitoyl PC. However, it should be understood that the phospholipid may contain any fatty acyl moiety typically found on a phospholipid, diacylyglycerol or triacylglycerol moiety. In other specific embodiments, the phospholipid component is PE.

In certain aspects of the methods of the invention, the LPLA2 composition is administered locally. In other aspects, the locally administered LPLA2 composition is administered in the form of an inhalant. In some treatment methods described herein the mammal is suffering from pulmonary alveolar proteinosis and the administration of the LPLA2 alleviates one or more of the symptoms of pulmonary alveolar proteinosis.

The invention further contemplates a method of treating pulmonary alveolar proteinosis, and conditions associated therewith, in a mammal comprising increasing LPLA2 activity in the alveolar macrophages of the mammal. Also described herein are exemplary embodiments in which the increasing LPLA2 activity comprises administering to the mammal a first composition comprising LPLA2 in a pharmaceutically acceptable carrier in an amount effective to increase phospholipid catabolism in the alveolar macrophages of the mammal. Other embodiments contemplate that the first composition comprising the LPLA2 comprises a LPLA2 protein composition. In further embodiments, the increasing LPLA2 activity comprises administering to the mammal a composition comprising a stimulator of LPLA2 activity of a protein of SEQ ID NO:2. Alternatively, the stimulator stimulates the activity of a protein of SEQ ID NO:11 or a protein of SEQ ID NO:13. In yet other examples, increasing the activity of LPLA2 comprises increasing the expression of LPLA2 in the alveolar macrophages of the mammal. In specific examples, the increasing expression of LPLA2 in the alveolar macrophages of the mammal comprises contacting the macrophages with an expression construct comprising an isolated polynucleotide encoding a LPLA2 operably linked to a promoter that promotes the expression of the LPLA2 in the alveolar macrophages. In more particular embodiments, the isolated polynucleotide encoding the LPLA2 comprises a polynucleotide encoding a protein of SEQ ID NO: 2 or a polynucleotide encoding an active fragment of a protein of SEQ ID NO:2. Alternatively, the isolated polynucleotide encodes a protein of SEQ ID NO:11 or SEQ ID NO:13.

In the treatment methods of the invention, the mammal being treated manifests a symptom of pulmonary alveolar proteinosis selected from the group consisting of respiratory insufficiency, dry cough, polycythemia, hypergammaglobulinemia, hypoxemia, and chest X-ray showing butterfly pattern opacity and the treating alleviates one or more of the symptoms.

The methods of the invention also contemplate combination treatment which comprises administering a second composition comprising a potassium iodide, a proteolytic enzyme, a corticosteroid, a cytokine. The cytokine to be administered may be any cytokine that reduces an inflammatory disorder or the like. In specific embodiments, the cytokine is GM-CSF. Other cytokines also may be used.

Also contemplated is a method of inhibiting the accumulation of phospholipid in alveolar macrophage tissue comprising contacting the alveolar macrophage tissue with a composition comprising LPLA2 in an amount effective to increase the catabolism of pulmonary surfactant.

Another aspect of the invention is directed to a method of diagnosing pulmonary alveolar proteinosis in a test mammal suspected of having the disorder comprising comparing LPLA2 activity and/or expression in the test mammal to the LPLA2 activity and/or expression of a reference mammal known not have such a disorder, wherein a decreased LPLA2 activity and/or expression in the test mammal compared to the reference mammal indicates pulmonary alveolar proteinosis in the test mammal.

Yet another diagnostic method contemplates diagnosing pulmonary alveolar proteinosis in a test mammal suspected of having the disorder comprising determining the presence of LPLA2 activity and/or expression in the alveolar macrophages of the test mammal; comparing the LPLA2 activity and/or expression to the LPLA2 activity and/or expression of a reference mammal that does not have such a disorder and diagnosing pulmonary alveolar proteinosis in the test mammal if the test mammal has a decreased LPLA2 activity and/or expression as compared to the reference mammal.

The present invention also contemplates methods of screening for a modulator of alveolar phospholipid catabolism comprising: comparing activity of LPLA2 in the presence and absence of a candidate substance, wherein an alteration in the activity of the LPLA2 activity in the presence of the candidate substance indicates that the substance is a modulator of alveolar phospholipid catabolism.

Another screening method contemplated is one which involves screening for a modulator of alveolar phospholipid catabolism comprising: contacting a LPLA2 of SEQ ID NO:2 with a candidate modulator; monitoring the activity of the LPLA2; and comparing the activity of LPLA2 in the presence and absence of the candidate substance; wherein an alteration in the activity of the LPLA2 activity indicates that the substance is a modulator of alveolar phospholipid catabolism. Similar screening assays also are set up in which an LPLA2-type protein such as one having a sequence of e.g., SEQ ID NO: 11 or SEQ ID NO:13 is contacted with the candidate modulator.

The modulator of the LPLA2 is a stimulator of the phospholipid catabolism is some embodiments and also is an activator of the LPLA2 activity in other embodiments. The candidate substance is selected from the group consisting of a small molecule from a small molecule library, an antibody, and a proteolytic enzyme.

Also provided is a method of treating alveolar proteinosis and conditions associated therewith in a human patient, the method comprising introducing into the lung tissue of the patient an effective amount of functionally active LPLA2 thereby increasing the LPLA2 activity of the alveolar macrophages and producing an increase in catabolism of the phospholipid components of the pulmonary surfactant of the patient.

Another aspect of the invention provides a method of treating alveolar proteinosis in a human patient, the method comprising the steps of: introducing into lung tissue of the patient an effective amount of a polynucleotide that encodes a functionally active LPLA2; and expressing the LPLA2 in the alveolar macrophages of the patient thereby increasing the LPLA2 activity of the alveolar macrophages and producing an increase in catabolism of the phospholipid components of the pulmonary surfactant of the patient.

Also taught herein is a composition comprising a LPLA2 protein for use in the treatment of a disorder caused by decreased phospholipid catabolism. The composition is provided for use in the treatment of pulmonary alveolar proteinosis and conditions associated therewith.

Another embodiment contemplates a composition comprising an expression construct that encodes a biologically active LPLA2 protein operably linked to a promoter functional in alveolar macrophages for use in the treatment of a disorder caused by decreased phospholipid catabolism. The composition is contemplated for use in the treatment of pulmonary alveolar proteinosis and conditions associated therewith.

The invention is further directed to a transgenic mouse comprising a disrupted lpla2 gene, wherein the transgenic mouse is homozygous for the disrupted lpla2 gene, and wherein the transgenic mouse exhibits a phenotype in which the mice lack phospholipase activity and show an accumulation of phospholipids in one or more tissues selected from the group consisting of alveolar macrophages, peritoneal macrophages, and spleen, as compare to non-transgenic mice of the same lineage. In specific embodiments, the lpla2$^{-/-}$ mice were generated by the systemic deletion of the lpla2 gene exon 5, which encodes the lipase motif essential for LPLA2 activity. The mice present a phospholipidosis characteristic, while the mice are healthy at birth and fertile, they showed no lysosomal phospholipase A2 activity systemically and, at an early age, showed significant accumulation of PE and PC in alveolar macrophages, peritoneal macrophages, and spleen that is characteristic of phospholipidosis. In specific embodiments, it is shown that there is particularly an accumulation of phospholipids that comprise two saturated fatty acids (i.e., are disaturated phospholipids). In more particular embodiments, the disaturated phospholipids are disaturated PC moieties, more particularly, dipalmitoyl PC is accumulated.

Also provided herein are methods of making a transgenic mouse having a disrupted lpla2 gene, comprising providing a murine embryonic stem cell comprising an intact lpla2 gene that contains exon 5 of lpa2 gene sequence; providing a targeting vector capable of disrupting the lpla2 gene upon homologous recombination; introducing the targeting vector into the murine embryonic stem cell under conditions where the targeting vector will undergo homologous recombination with the lpla2 gene of the murine embryonic stem cell to produce a disrupted gene; introducing the murine embryonic stem cell into a blastocyst; implanting the blastocyst into a pseudopregnant female mouse; and delivering a first transgenic mouse comprising a disrupted lpla2 gene from the pseudopregnant female; repeating the above steps to obtain a second transgenic mouse comprising a disrupted lpla2 gene; and breeding the first transgenic mouse comprising a disrupted lpla2 gene to the second transgenic mouse comprising a disrupted lpla2 gene to obtain one or more mice homozygous for a disrupted lpla2 gene.

The invention is further directed to a murine cell line comprising a disrupted lpla2 gene, wherein substantially all cells of the cell line have both copies of the lpla2 gene disrupted.

Other features and advantages of the invention will become apparent from the following detailed description. It should be understood, however, that the detailed description and the specific examples, while indicating particular embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIG. 1A shows LPLA2 activity in MDCK cell homogenates. The activity was assayed in the presence of varying concentrations of amiodarone, and D-t-PDMP, and tetracycline (an inactive control). Each compound was active in the inhibition of the phospholipase A2 activity. LPLA2 activity was measure as the formation of N-acetylsphingosine as described below. FIG. 1B shows the total phospholipid content measured following a 7-day exposure to 15 mM amiodarone and D-t-PDMP. Amiodarone treatment led to a greater level of total phospholipid consistent with its greater inhibitory activity against LPLA2. The changes in individual species of phospholipids following amiodarone (FIG. 1C) and PDMP (FIG. 1D) were also measured.

FIG. 4A. LPLA2 activity on unsaturated phosphatidylcholine. Soluble fraction (2 µg of protein) obtained from 3 month-old lpla2$^{+/+}$ mice was incubated for a suitable time period at 37° C. in citrate buffer, pH 4.5, with 40 μM NAS incorporated into phospholipid liposomes (DOPC or POPC/dicetyl phosphate/NAS (7:1:2 in molar ratio)) and formation of 1-O-oleoyl-NAS was determined as described in Example 4. The left panel shows TLC. The right panel shows formation of 1-O-oleoyl-NAS from DOPC or POPC/dicetyl phosphate/NAS liposomes by the soluble fraction. OA indicates oleic acid.

Figure 4A:
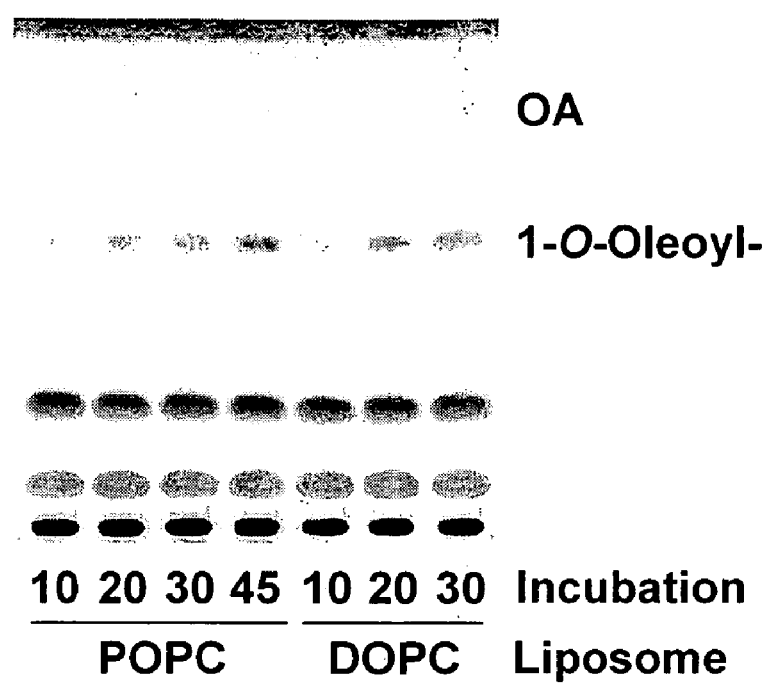
Figure 4B:
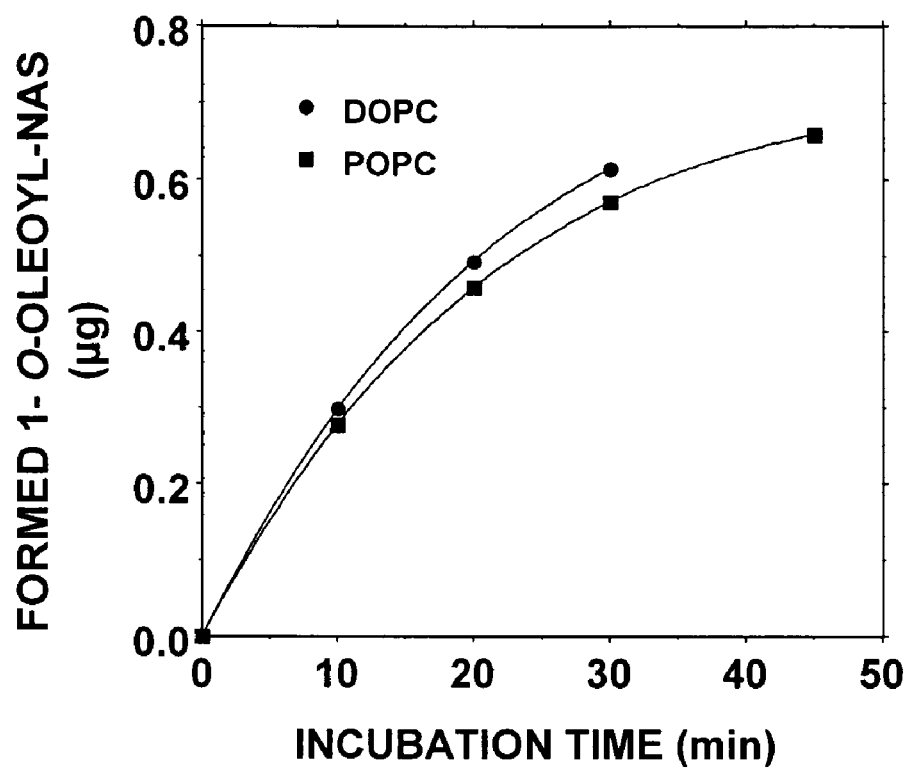

FIG. 4B. Degradation of 1-palmitoyl-2-[$^{14}$C]-oleoyl-ns-3-glycero-phosphorylcholine by AM. AM ($1.3 \times 10^6$ cells) obtained from 3 month-old lpla2$^{+/+}$ and lpla2$^{-/-}$ mice were incubated with [$^{14}$C]-labeled POPC/dicetyl phosphate (10:1 in molar ratio) liposomes for 4 h at 37° C. After the incubation, the cellular lipid was extracted as described in Example 4. Lipid extract was applied to an HPTLC and developed in a solvent system consisting of chloroform/acetic acid (9:1) (left) or chloroform/methanol/water (60:35:8) (right). After the development, the plate sprayed with ENHANCE was exposed on an X-ray film at −80° C. LysoPC indicates lysophosphatidylcholine.

Figure 5A:
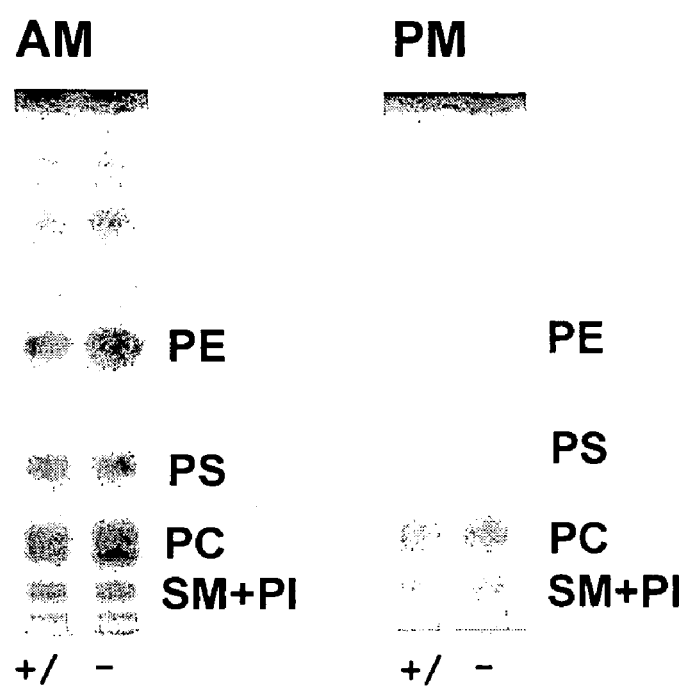

FIG. 5A. Phospholipid accumulation in AM and PM obtained from lpla2$^{-/-}$ mice. 3 month-old lpla2$^{+/+}$ and lpla2$^{-/-}$ mice were used. Each cell homogenate prepared from AM and PM was dispersed in chloroform/methanol mixture and lipid extraction was carried out as described in Example 4. In this study, lipid extracts obtained from 32 μg of protein of AM homogenate and 12 μg of protein of PM homogenate were developed by an HPTLC. PE, PS, PC, PI and SM indicate phosphatidylethanolamine, phosphatidylcholine, phosphatidylserine, phosphatidylinositol and sphingomyelin, respectively.

Figure 5B:
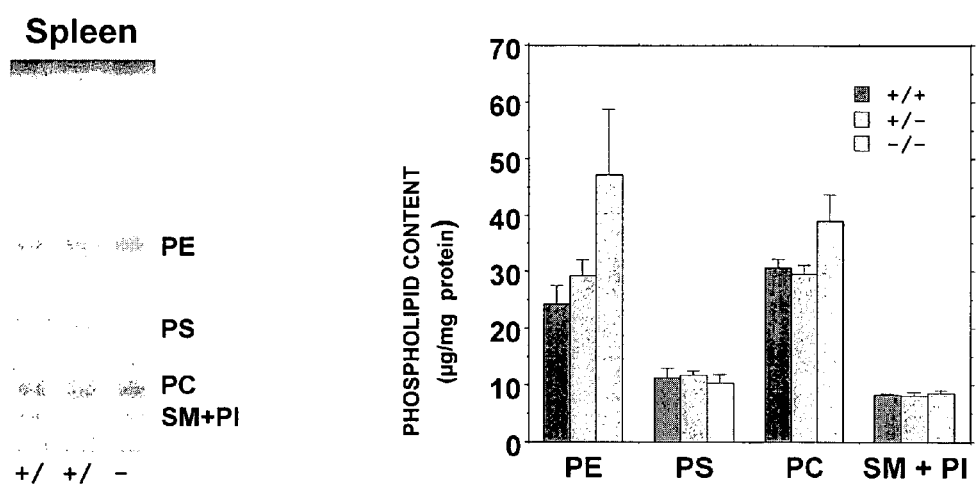

FIG. 5B. Phospholipid accumulation in spleen obtained from lpla2$^{-/-}$ mice. Spleen homogenate obtained from 3 month-old LPLA2$^{+/+}$, LPLA2$^{+/-}$ and lpla2$^{-/-}$ mice dispersed in chloroform/methanol mixture and lipid extraction was carried out as described in the Example 4. In the left panel, lipid extract obtained from 30 μg of protein of spleen homogenate was developed by an HPTLC. The right panel shows the major phospholipid profile in spleen obtained from the lpla2$^{+/+}$, lpla2$^{+/-}$ and lpla2$^{-/-}$ mice. Error bar indicates S. D. (n=4).

FIG. 6. Electron micrographs of AM and PM obtained from 3 month-old lpla2$^{+/+}$ and lpla2$^{-/-}$ mice. A and B, and C and D show AM and PM, respectively. A and C are from lpla2$^{+/+}$ mice. B and D are from lpla2$^{-/-}$ mice.

DESCRIPTION OF THE PREFERRED EMBODIMENTS

Pulmonary alveolar proteinosis is a disorder of impaired catabolism of surfactant phospholipids and proteins. This disorder manifests as an excess surfactant accumulation in the lungs associated with the engorgement of lipids within alveolar macrophages. Present treatments of this disorder involve removal of the excessive lipids using a bronchioalveolar lavage or even lung transplants. The present invention is directed to providing alternative methods of therapeutic intervention of this disorder.

In brief, the present application discloses the involvement of a particular lysosomal phospholipase A2 in catabolism of alveolar surfactant phospholipids. This phospholipase A2, termed LPLA2, has specificity towards the phospholipids phosphatidylcholine (PC) and phosphatidylethanolamine (PE). The phospholipase is localized to lysosomes, is calcium independent, has an acidic pH optimum, and transacylates ceramide. The protein is selectively and highly expressed in alveolar macrophages but is also present to a lesser degree in peritoneal macrophages, peripheral blood monocytes, or other tissues. Other macrophage-associated phospholipase A2s do not show a comparable distribution. This LPLA2 is present at high specific activity and recognizes disaturated-phosphatidylcholine as substrate. The LPLA2 is present at significantly reduced levels and activity in alveolar macrophages from mice with a targeted deletion of GM-CSF, a model of impaired surfactant catabolism, and is present at higher levels and activity in transgenic mice that over-express GM-CSF. Thus, LPLA2 is a major enzyme of pulmonary surfactant phospholipid degradation and may be deficient in disorders of surfactant metabolism. The present specification is directed to methods and compositions for exploiting these findings. Such methods and compositions are described in further detail herein below.

In addition to the above findings, the present invention is directed to model animals that provide a model of phospholipidosis. The present invention provides lpla2$^{-/-}$ mice that were generated by the systemic deletion of the lpla2 gene exon 5, which encodes the lipase motif essential for LPLA2 activity. These mice were healthy at birth and fertile, they showed no lysosomal phospholipase A2 activity systemically and, at an early age, showed an accumulation of PE and PC in alveolar macrophages, peritoneal macrophages, and spleen that is characteristic of phospholipidosis. A similar trend in the phospholipid profile was also observed in tissues such as liver and lung. The selective accumulation of PE and PC in lpla2$^{-/-}$ mice is consistent with the substrate specificity of LPLA2. Both phospholipids are preferred substrates of LPLA2. Electron microscopy revealed the presence of excessive lamellar inclusion bodies in lpla2$^{-/-}$ alveolar and peritoneal macrophages. This foam cell phenotype is characteristic of cellular phospholipidosis and in this case is due to a marked accumulation of phospholipid in lysosomes induced by the impairment of phospholipid degradation by the deficiency of lpla2.

Alveolar macrophages were found to be the most sensitive cells for the development of phospholipidosis in the lpla2$^{-/-}$ mice. LPLA2 protein is highly expressed in alveolar macrophages and these mice further demonstrate that this enzyme plays an important role in phospholipid degradation of pulmonary surfactant.

It has been reported that DPPC, the major lipid of pulmonary surfactant, is mainly degraded via phospholipase A1, C or D in alveolar macrophages. The data described in the examples provided herein demonstrate that DPPC acts as a substrate of the LPLA2 enzyme, but is less favored as compared to DOPC (FIG. 2A) where the unsaturated form of PC, POPC, was significantly degraded by alveolar macrophages from lpla2$^{-/-}$ but not lpla2$^{+/+}$ mice. This was further confirmed with the use of radiolabeled POPC in which POPC incorporated into wild-type mouse alveolar macrophages was mainly degraded by phospholipase A1 and phospholipase A2 in the alveolar macrophages. The amount of product generated by lpla2 was 50% higher than that of phospholipase A1. The same study using lpla2$^{-/-}$ alveolar macrophages demonstrated that the product in the lpla2$^{-/-}$ mouse alveolar macrophages was less than 10% of that in wild type mouse cells. Thus, it is demonstrated that the catabolism of POPC in the lpla2$^{+/+}$ alveolar macrophages is mostly by lpla2 enzyme, i.e., more than half of the POPC in pulmonary surfactant taken up by alveolar macrophages may be degraded by lpla2.

Alveolar macrophages (AM) constantly ingest great amounts of exogenous phospholipid rich substances such as pulmonary surfactant in alveolar materials and have to metabolize them to keep the phospholipid levels normal.

Therefore, the impairment of phospholipid degradation pathway in the AM may easily induce unusual cellular phospholipid accumulation, resulting in phospholipidosis and foam cell formation, compared with other tissues and cells. It can be seen from FIG. 6 that there was an enlargement of lpla2$^{-/-}$ mouse AM caused by accumulation of lamellar membranous inclusion bodies. An excessive accumulation of phospholipid is thought to impair the macrophage function and the survival. LPLA2-deficient mice may have a disorder in phospholipid metabolism of pulmonary surfactant, although there has been no significant difference in the phospholipid content in bronchoalveolar lavage fluid between 3 month to 5.5 month-old lpla2$^{+/+}$ and lpla2$^{-/-}$ mice.

Lipid storage disorders or lipidoses are generally considered as disorders of the cellular lipid metabolism in lysosome. Phospholipidosis that is distinguished from Niemann-Pick's disease has not been well known, except for phospholipidosis induced by cationic amphiphilic drugs. Although phospholipidosis in humans has been reported, these disorders were not enzymologically- nor genetically-linked to phospholipase. The present application using LPLA2-deficient mice for the first time provides evidence that the block of the degradation pathway of phospholipid by the deficiency of LPLA2 induces selective accumulation of phospholipid and leads to the development of phospholipidosis. LPLA2 deficient mice showed that LPLA2 play an important role in cellular phospholipid homeostasis. The availability of lpla2$^{-/-}$ mice provides an efficient and effective model for investigating further biological functions of LPLA2 enzyme/protein and also for testing agents that affect the activity of this enzyme as well as agents that may be used to ameliorate phospholipidosis as well as to screen for agents that cause or exacerbate phospholipidosis. Methods and compositions for preparing the transgenic models of the present invention and the uses of the models as well as cells derived therefrom in the testing of agents discussed above are provided in further detail herein below.

Lysosomal Phospholipase A2

The present invention is directed to methods of treating a variety of disorders of surfactant metabolism by administering compositions comprising LPLA2, compositions that augment, increase or otherwise stimulate the activity of LPLA2, and compositions that increase or otherwise stimulate the expression of LPLA2. In addition, the methods of the invention are directed to identifying additional agents that may facilitate an increase in the activity and/or expression of LPLA2 activity, as well as use of LPLA2 in the diagnosis of disorders of surfactant metabolism. The present section provides a general description of LPLA2 proteins and their involvement in disorders of surfactant metabolism.

LPLA2, also known as 1-O-acylceramide synthase, is an enzyme that transacylates ceramide at the 1-hydroxyl position and was previously identified (Abe, et al., J Biol Chem 271, 14383-9, 1996). In the presence of ceramide, the enzyme catalyzes the formation of 1-O-acylceramide by transacylation of fatty acids from the sn-2 position of phosphatidylcholine or phosphatidylethanolamine. In the absence of ceramide or other alcohols as acceptors, the enzyme acts as a traditional phospholipase A2. However, the phospholipase, a single-chain glycoprotein having a molecular mass of about 40 kDa, has a pH optimum of 4.5, is mannose rich, and is calcium independent (Abe et al., J Biol Chem 273, 8467-74, 1998). The phospholipase is 50% identical to cholesterol lecithin acyltransferase (LCAT; Hiraoka et al., J Biol Chem 277, 10090-9, 2002; Bovine sequences: SEQ ID NO:1 & 2; human sequences SEQ ID NO:10 & 11; mouse sequences: SEQ ID NO:12 & 13;) and has a sequence of SEQ ID NO:2. The homology with LCAT is highest within the catalytic domain but absent in the lipoprotein binding region. The phospholipase colocalizes with other lysosomal proteins in cell fractionates. Upon the initial characterization of this enzyme, the functional role of this phospholipase A2 was not immediately apparent. The divalent cations $Ca^{2+}$ and $Mg^{2+}$ enhanced, but are not required for, transacylase activity. The enzyme was neither activated nor inhibited in the presence of ATP or thiol reagents such as dithiothreitol and NEM. Thus the enzyme differs from groups I, II, and III phospholipase A2s. The latter groups are highly sensitive to such reagents. The phospholipase A2 inhibitors bromoenollactone (BEL) and nonadecyltetraenyl trifluoromethyl ketone (AACOF3) did not inhibit the enzyme activity. Thus inhibitors of both the calcium dependent and calcium independent cytosolic phospholipase A2s of the higher molecular weights were inactive against the 1-O-acylceramide synthase.

LPLA2 fulfilled several criteria for being defined as a unique phospholipase A2. First, hydrolyzes fatty acids from the sn-2 position of both phosphatidylcholine and phosphatidylethanolamine. Second, the complete amino acid sequence has been defined. Third, like several other phospholipase A2s, LPLA2 contains a catalytically active serine. Mutagenesis of this site abolishes the phospholipase A2 activity. Fourth, it is phylogentically related to a larger family of lipases, including LCAT. Fifth, unlike other groups of phospholipase A2s, the new phospholipase A2 has an acidic pH optimum, is mannose rich, and is localized to lysosomes. Sixth, it has a unique activity profile and chromosomal location.

Previously, a role for an acidic phospholipase A2 activity has been suggested for the degradation of pulmonary surfactant phospholipids (Rao et al., Exp Lung Res 2, 9-15, 1981). Further a pulmonary acidic phospholipase A2 activity has also been postulated to be calcium independent and inhibited by a transition state analog of arachidonate, MJ33 (Fisher et al., Biochem J 288 (Pt 2), 407-11, 1992). In rats treated with MJ33 surfactant phospholipid catabolism was inhibited by approximately 40 to 50% suggesting that the drug-sensitive phospholipase A2 activity contributes significantly to total surfactant degradation (Fisher et al., Am J Physiol Lung Cell Mol Physiol 280, L748-54, 2001).

Despite the above general studies, prior to the disclosure of the present invention, the exact identity of LPLA2 in alveolar macrophages remained unelucidated. In the present application studies to elucidate the role of the specific protein of SEQ ID NO:2 in pulmonary surfactant catabolism are described. These studies, described and discussed in further detail in the Examples presented below, demonstrated the robust expression of an acidic lysosomal phospholipase A2 of SEQ ID NO:2 within the alveolar macrophage, the primary site of surfactant degradation. The low expression and activity of this phospholipase A2 in a model of pulmonary alveolar proteinosis demonstrated that this phospholipase likely mediates human disorders associated with abnormal surfactant metabolism. In addition, the Examples provided herein below, it is shown that the PDMP class of glucosylceramide synthase inhibitors block LPLA2 activity and induce phospholipidosis. The significance of this finding with respect to drug-induced phospholipidosis is further elucidated herein below.

The present invention for the first time describes that compositions comprising LPLA2 having a sequence of SEQ ID NO:2, or biologically active analogs, fragments or variants thereof, for use in the treatment of disorders of phospholipid catabolism.

As used herein the term "LPLA2" or "LPLA2-derived protein" is intended to encompass any protein that is derived from the sequence of SEQ ID NO:2, is a fragment of SEQ ID NO:2, or an analog or conservative variant of a protein of SEQ ID NO:2 that has any catabolic effect on phospholipids. In specific embodiments such an enzyme specifically catabolizes PC and/or PE. In certain aspects, the LPLA2 protein is derived from any natural source, e.g., a mammalian origin such as human, bovine, murine (e.g., of these sequences are depicted in Hiraoka et al., J Biol Chem 277, 10090-9, 2002), or alternatively it is produced through recombinant methods known to those of skill in the art. In one embodiment, a LPLA2-derived protein of SEQ ID NO:2 from a human source is provided. However, it should be understood that any variant, analog or fragment of SEQ ID NO:2 can be used in the methods of the present invention as long as such a variant, analog or fragment possesses some degree of enzyme activity associated with the protein of SEQ ID NO:2. An exemplary such protein cloned, isolated and characterized from a bovine source is found at GenBank Accession No. AY072914 and is particularly useful in the present invention. Those skilled in the art also are referred to Hiraoka et al., J Biol Chem 277, 10090-9, 2002, which shows the sequences of the human and mouse enzymes.

While certain embodiments provide an LPLA2 protein having the sequence of SEQ ID NO:2, it is also contemplated that conservative substitution of amino acid residues of this protein also are produced that nonetheless retain the functional activity of the protein of SEQ ID NO:2 and/or retain three-dimensional conformation structure of the protein of SEQ ID NO:2.

The term "conservative substitution" as used herein denotes the replacement of an amino acid residue by another, biologically similar residue with respect to hydrophobicity, hydrophilicity, cationic charge, anionic charge, shape, polarity and the like. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which are substituted for one another include asparagine, glutamine, serine and threonine. The term "conservative substitution" also includes the use of a substituted or modified amino acid in place of an unsubstituted parent amino acid provided that antibodies raised to the substituted polypeptide also immunoreact with the unsubstituted polypeptide. By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties. Exemplary conservative substitutions are set out in e.g., Alternatively, conservative amino acids are grouped as described in Lehninger, [*Biochemistry*, Second Edition; Worth Publishers, Inc. NY: N.Y. (1975), pp. 71-77]. Those of skill in the art are aware of numerous tables that indicate specific conservative substitutions. One exemplary such table is provided below:

Table of Exemplary Conservative Substitutions

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Any conservative variant of a protein of SEQ ID NO:2 that retains most or all of the catalytic domain of the LPLA2 of SEQ ID NO:2 is contemplated to be a particularly useful variant in the methods of the present invention. In this context, it was discovered that the LPLA2 of SEQ ID NO:2 has 50% homology to cholesterol lecithin acyltransferase (LCAT), and the majority of this homology is within the catalytic domain. Thus, it is contemplated that those of skill in the art may choose to produce variants of SEQ ID NO:2 in which the catalytic domain of SEQ ID NO:2 is replaced by the catalytic domain of an LCAT (Hiraoka et al., J Biol Chem 277, 10090-9, 2002), as long as such a variant retains its property of catalyzing phospholipid breakdown. Such activities are readily assessed as described herein below.

In addition to the basic amino acid structure of the proteins, it is contemplated that the LPLA2-based proteins will be modified to enhance their uptake, circulation, and/or other modifications to render the peptides more therapeutically effective. For example, it has been discovered herein that LPLA2 activity is required to promote the breakdown of pulmonary surfactant, thus any medium or modification that facilitates the greater uptake of LPLA2 compositions by lung tissue and in particular, alveolar macrophages in alveoli is particularly useful.

In addition, rational drug design is used to produce structural analogs or variants of the LPLA2 proteins and thus provide additional compositions for use in the methods contemplated herein. By creating such analogs, the skilled worker can fashion LPLA2-derived proteins which are more active or stable than the natural molecules which have different susceptibility to alteration or which may affect the function of various other molecules. In one approach, it is desirable to generate a three-dimensional structure for LPLA2-derived protein of interest or a fragment thereof e.g., this is accomplished by x-ray crystallography, computer modeling or by a combination of both approaches. An alternative approach, "alanine scan," involves the random replacement of residues throughout molecule with alanine, and the resulting affect on function determined.

The invention further provides LPLA2-specific antibodies, selected by a functional assay. Indeed a polyclonal antibody has been isolated as discussed in the Examples below. Those skilled in the art also will be able to produce monoclonal antibodies specific for LPLA2. Once such a monoclonal antibody is isolated, one then resolves its crystal structure. In principle, this approach yields a pharmacore upon which subsequent drug design is based. It is possible to bypass protein crystallography altogether by generating anti-idiotypic antibodies to a functional, pharmacologically active antibody. As a mirror image of a mirror image, the binding site of anti-idiotype is an analog of the original antigen. The anti-idiotype is then be used to identify and isolate peptides from banks of chemically- or biologically-produced peptides. Selected peptides then serve as the pharmacore. Anti-idiotypes are generated by producing antibodies specific for a given protein and then using such an antibody as the antigen.

Thus, one designs drugs which have improved LPLA2 protein activity or which act as stimulators, or agonists, of LPLA2. By virtue of the availability of cloned LPLA2 sequences, sufficient amounts of such protein are produced to perform crystallographic studies. In addition, knowledge of the polypeptide sequences provides computer employed predictions of structure-function relationships.

Furthermore, nonpeptide analogs of LPLA2-derived proteins that provide a stabilized structure or lessened biodegradation, are also contemplated. Peptide mimetic analogs are prepared based on a the underlying LPLA2 protein structure by replacing one or more amino acid residues of the protein of interest by nonpeptide moieties. In one aspect, the nonpeptide moieties permit the peptide to retain its natural confirmation, or stabilize a bioactive confirmation. One example of methods for preparation of nonpeptide mimetic analogs from peptides is described in Nachman et al., *Regul. Pept.* 57:359-370 (1995). Peptide as used herein embraces all of the foregoing.

In another aspect, the LPLA2 proteins used in the therapeutic methods of the present invention are modified in order to improve their therapeutic efficacy. Such modification of therapeutic compounds is used to decrease toxicity, increase circulatory time, or modify biodistribution. For example, the toxicity of potentially important therapeutic compounds is decreased significantly by combination with a variety of drug carrier vehicles that modify biodistribution. In certain embodiments described herein the LPLA2-derived proteins have their therapeutic effect by increasing phospholipid catabolism in alveolar macrophages. As such, any modification that allows the peptide to be taken up and have an effect in lung tissue is useful.

A strategy for improving drug viability is the utilization of water-soluble polymers. Various water-soluble polymers have been shown to modify biodistribution, improve the mode of cellular uptake, change the permeability through physiological barriers, and modify the rate of clearance from the body. (Greenwald et al., Crit Rev Therap Drug Carrier Syst. 2000;17:101-161; Kopecek et al., J Controlled Release., 74:147-158, 2001). To achieve either a targeting or sustained-release effect, water-soluble polymers have been synthesized that contain drug moieties as terminal groups, as part of the backbone, or as pendent groups on the polymer chain.

Polyethylene glycol (PEG), has been widely used as a drug carrier, given its high degree of biocompatibility and ease of modification. Harris et al., Clin Pharmacokinet. 2001; 40(7): 539-51 Attachment to various drugs, proteins, and liposomes has been shown to improve residence time and decrease toxicity. (Greenwald et al., Crit Rev Therap Drug Carrier Syst. 2000; 17:101-161; Zalipsky et al., Bioconjug Chem. 1997; 8:111-118). In one aspect, PEG is coupled to active agents through the hydroxyl groups at the ends of the chain and via other chemical methods; however, PEG itself is limited to at most two active agents per molecule. In a different approach, copolymers of PEG and amino acids were explored as biomaterials which retain the biocompatibility properties of PEG, but which have the added advantage of numerous attachment points per molecule (providing greater drug loading), and which could be synthetically designed to suit a variety of applications (Nathan et al., Macromolecules. 1992; 25:4476-4484; Nathan et al., Bioconj Chem. 1993; 4:54-62).

Those of skill in the art are aware of PEGylation techniques for the effective modification of drugs. For example, drug delivery polymers that consists of alternating polymers of PEG and tri-functional monomers such as lysine have been used by VectraMed (Plainsboro, N.J.). The PEG chains (typically 2000 daltons or less) are linked to the $\alpha$- and $\epsilon$-amino groups of lysine through stable urethane linkages. Such copolymers retain the desirable properties of PEG, while providing reactive pendent groups (the carboxylic acid groups of lysine) at strictly controlled and predetermined intervals along the polymer chain. In one aspect, the reactive pendent groups are used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate increases the circulatory half-life of the conjugate. Nevertheless, the conjugate must either be readily degradable or have a molecular weight below the threshold-limiting glomular filtration (e.g., less than 45 kDa). Thus, in one aspect, PEGylated LPLA2 proteins are in the range of between 20 and 35 kDa in molecular weight.

Methods of Making LPLA2 Proteins

The present invention provides LPLA2-related proteins or peptides for use the manufacture of medicaments for the treatment of disorders of surfactant metabolism. In one aspect, such proteins or peptides are produced by conventional automated peptide synthesis methods or by recombinant expression. General principles for designing and making proteins are well known to those of skill in the art.

A. Automated Solid-Phase Peptide Synthesis

In one aspect any protein of the invention is synthesized in solution or on a solid support in accordance with conventional techniques. Various automatic synthesizers are commercially available and is used in accordance with known protocols. See, for example, Stewart and Young, Solid Phase Peptide Synthesis, 2d. ed., Pierce Chemical Co., (1984); Tam et al., J. Am. Chem. Soc., 105:6442, (1983); Merrifield, Science, 232: 341-347, (1986); and Barany and Merrifield, The Peptides, Gross and Meienhofer, eds, Academic Press, New York, 1-284, (1979), each incorporated herein by reference. As such, LPLA2 proteins, fragments analogs and variants thereof is readily synthesized and then screened for a related activity e.g., aclyceramide synthase activity assays.

For example, the peptides are synthesized by solid-phase technology employing an exemplary peptide synthesizer such as a Model 433A from Applied Biosystems Inc. In such cases, the purity of any given peptide substrate, generated through automated peptide synthesis or through recombinant methods, is typically determined using reverse phase HPLC analysis. Chemical authenticity of each peptide is established by any method well known to those of skill in the art. In certain embodiments, the authenticity is established by mass spectrometry. Additionally, the peptides also are quantified using amino acid analysis in which microwave hydrolyses are conducted. In one aspect, such analyses use a microwave oven such as the CEM Corporation's MDS 2000 microwave oven. The peptide (approximately 2 µg protein) is contacted with e.g., 6 N HCl (Pierce Constant Boiling e.g., about 4 ml) with approximately 0.5% (volume to volume) phenol (Mallinckrodt). Prior to the hydrolysis, the samples are alternately evacuated and flushed with $N_2$. The protein hydrolysis is conducted using a two-stage process. During the first stage, the peptides are subjected to a reaction temperature of about 100° C. and held that temperature for 1 minute. Immediately after this step, the temperature is increased to 150° C. and held at that temperature for about 25 minutes. After cooling, the samples are dried and amino acid from the hydrolysed peptides samples are derivatized using 6-aminoquinolyl-N-hydroxysuccinimidyl carbamate to yield stable ureas that fluoresce at 395 nm (Waters AccQ Tag Chemistry Package). In certain aspects, the samples are analyzed by reverse phase HPLC and quantification is achieved using an enhanced integrator. Those of skill in the art are referred to Hiraoka et al., which describes details of methods of determining amino acid sequence of LPLA2 using a combination reverse phase HPLC and mass spectrometry. Such methods are well known to those of skill in the art and are readily adapted for the sequence analysis of any protein or peptide.

B. Recombinant Protein Production.

As an alternative to automated peptide synthesis, recombinant DNA technology is employed wherein a nucleotide sequence which encodes a peptide of the invention is inserted into an expression vector, transformed or transfected into an appropriate host cell and cultivated under conditions suitable for expression as described herein below. In one aspect, a nucleotide sequence that encodes a protein of SEQ ID NO:2 is provided in SEQ ID NO:1 but it is understood that any polynucleotide encoding SEQ ID NO:2 is contemplated. Recombinant methods are especially useful for producing longer polypeptides for use in the methods of the invention.

A variety of expression vector/host systems are utilized to contain and express the peptide or protein coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below.

Expression vectors for use in prokaryotic hosts generally comprise one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), pET vectors (Novagen) and pQE vectors (Qiagen).

The DNA sequence encoding the given protein or fusion polypeptide is amplified by PCR and cloned into such a vector, for example, pGEX-3X (Pharmacia, Piscataway, N.J.) designed to produce a fusion protein comprising glutathione-S-transferase (GST), encoded by the vector, and a protein encoded by a DNA fragment inserted into the vector's cloning site. Typically, the primers for the PCR are generated to include for example, an appropriate cleavage site. Treatment of the recombinant fusion protein with thrombin or factor Xa (Pharmacia, Piscataway, N.J.) cleaves the fusion protein, releasing the protein of interest from the GST portion. The pGEX-3x/LPLA2 peptide construct is transformed into E. coli XL-1 Blue cells (Stratagene, La Jolla Calif.), and individual transformants are isolated and grown. Plasmid DNA from individual transformants is purified and partially sequenced using an automated sequencer to confirm the presence of the desired peptide or polypeptide encoding nucleic acid insert in the proper orientation. If the GST/LPLA2 fusion protein is produced in bacteria as a soluble protein, it is then purified using the GST Purification Module (Pharmacia Biotech).

Alternatively, the DNA sequence encoding the LPLA2-containing fusion polypeptide is cloned into a plasmid containing a desired promoter and, optionally, a leader sequence (see, e.g., Better et al., Science, 240:1041-43, 1988). In exemplary aspects, the sequence of this construct is confirmed by automated sequencing, but other methods of confirming the sequence also are used. The plasmid is then transformed into E. coli using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will effect secretion of the mature LPLA2 substrate or fusion protein and be cleaved during secretion.

The secreted recombinant protein is purified from the bacterial culture media by conventional protein purification methods. Similar systems for the production of recombinant protein in yeast host cells are readily commercially available, e.g., the *Pichia* Expression System (Invitrogen, San Diego, Calif.), following the manufacturer's instructions. Another alternative recombinant production is achieved using an insect system. Insect systems for protein expression are well known to those of skill in the art. In one such system, *Autographa californica* nuclear polyhedrosis virus (AcNPV) is used as a vector to express foreign genes in *Spodoptera frugiperda* cells or in *Trichoplusia larvae*. The substrate coding sequence is cloned into a nonessential region of the virus, such as the polyhedrin gene, and placed under control of the polyhedrin promoter. Successful insertion of substrate will render the polyhedrin gene inactive and produce recombinant virus lacking coat protein coat. The recombinant viruses are then used to infect *S. frugiperda* cells or *Trichoplusia larvae* in which the substrate is expressed (Smith et al., J Virol 46: 584, 1983; Engelhard E K et al., Proc Nat Acad Sci 91: 3224-7, 1994).

Mammalian host systems for the expression of recombinant proteins also are well known to those of skill in the art. Host cell strains are typically chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, W138, and the like, have specific cellular machinery and characteristic mechanisms for such post-translational activities and are chosen to ensure the correct modification and processing of the introduced, foreign protein.

In one aspect, the transformed cells are used for long-term, high-yield protein production and as such stable expression is desirable. Once such cells are transformed with vectors that contain selectable markers along with the desired expression cassette, the cells are allowed to grow for 1-2 days in an enriched media before they are switched to selective media. The selectable marker is designed to confer resistance to selection and its presence allows growth and recovery of cells which successfully express the introduced sequences. Resistant clumps of stably transformed cells are proliferated using tissue culture techniques appropriate to the cell.

A number of selection systems are useful to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk−, hgprt− or aprt− cells, respectively. In other aspects, anti-metabolite resistance is used as the basis of selection for dhfr, which confers resistance to methotrexate; gpt, which confers resistance to mycophenolic acid; neo, which confers resistance to the aminoglycoside G418; als which confers resistance to chlorsulfuron; and hygro, which confers resistance to hygromycin. Additional selectable genes that are useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

C. Expression Constructs for Recombinant Protein Production

Recombinant production of the LPLA2 proteins of the invention employs vectors comprising polynucleotide molecules for encoding the LPLA2 proteins. Methods of preparing such vectors as well as producing host cells transformed with such vectors are well known to those skill in the art. In one aspect, the polynucleotide molecules used in such an endeavor (e.g., a polynucleotide sequence of SEQ ID NO:1 or a variant thereof) are joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect gene. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan. Methods for the construction of mammalian expression vectors are disclosed, for example, in Okayama and Berg (Mol. Cell. Biol. 3:280 (1983)); Cosman et al. (Mol. Immunol. 23:935 (1986)); Cosman et al. (Nature 312:768 (1984)); EP-A-0367566; and WO 91/18982.

In one aspect, expression construct comprises a selectable marker that allows for the detection of the expression of a peptide or polypeptide. Usually the inclusion of a drug selection marker aids in cloning and in the selection of transformants, for example, neomycin, puromycin, hygromycin, DHFR, zeocin and histidinol. Alternatively aspects employ enzymes such as herpes simplex virus thymidine kinase (tk) (eukaryotic), β-galactosidase, luciferase, or chloramphenicol acetyltransferase (CAT) (prokaryotic) as markers. Alternatively, immunologic markers also are employed. For example, epitope tags such as the FLAG system (IBI, New Haven, Conn.), HA and the 6×His system (Qiagen, Chatsworth, Calif.) are employed. Additionally, glutathione S-transferase (GST) system (Pharmacia, Piscataway, N.J.), or the maltose binding protein system (NEB, Beverley, Mass.) also are used. The selectable marker employed is not believed to be important, so long as it is capable of being expressed simultaneously with the nucleic acid encoding a gene product. Further examples of selectable markers are well known to one of skill in the art.

Expression requires that appropriate signals be provided in the vectors, such as enhancers/promoters from both viral and mammalian sources that are used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the peptide substrate or the fusion polypeptide. Thus, a promoter nucleotide sequence is operably linked to a given DNA sequence if the promoter nucleotide sequence directs the transcription of the sequence. Similarly, the phrase "under transcriptional control" means that the promoter is in the correct location and orientation in relation to the nucleic acid to control RNA polymerase initiation and expression of the gene.

Any promoter that will drive the expression of the nucleic acid is used. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. In one aspect, such a promoter includes either a human or viral promoter. Common promoters include, e.g., the human cytomegalovirus (CMV) immediate early gene promoter, the SV40 early promoter, the Rous sarcoma virus long terminal repeat, β-actin, rat insulin promoter, the phosphoglycerol kinase promoter and glyceraldehyde-3-phosphate dehydrogenase promoter, all of which are promoters well known and readily available to those of skill in the art and are used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well known properties, the level and pattern of expression of the protein of interest following transfection or transformation is optimized. Inducible promoters also are contemplated for use.

Another regulatory element that is used in protein expression is an enhancer. These are genetic elements that increase transcription from a promoter located at a distant position on the same molecule of DNA. Where an expression construct employs a cDNA insert, one will typically desire to include a polyadenylation signal sequence to effect proper polyadenylation of the gene transcript. Any polyadenylation signal sequence recognized by cells of the selected transgenic animal species is suitable for the practice of the invention, such as human or bovine growth hormone and SV40 polyadenylation signals.

Also contemplated as an element of the expression cassette is a terminator. These elements serve to enhance message levels and to minimize read through from the cassette into other sequences. The termination region is selected for convenience, since termination regions for the applications such as those contemplated by the present invention appear to be relatively interchangeable. In certain aspects, the termination region is native with the transcriptional initiation, in other embodiments, it is native to the DNA sequence of interest, or alternatively it is derived for another source.

It should be noted that while the above discussion of expression vectors is applicable to the use of such vectors in large scale protein production, as well as in vivo delivery of such an expression vector to effect the expression of the protein in vivo. In one aspect, the expression constructs are introduced into the cells targeted for treatment using any methods known to those of skill in the art. For example, the expression constructs form part of a viral delivery vector. In other embodiments, non-viral delivery is contemplated. Receptor-mediated delivery also is contemplated (Ridgeway, In: Rodriguez R L, Denhardt D T, ed. Vectors: A survey of molecular cloning vectors and their uses. Stoneham: Butterworth, 467 492, 1988; Nicolas and Rubenstein, In: Vectors: A survey of molecular cloning vectors and their uses, Rodriguez & Denhardt (eds.), Stoneham: Butterworth, 493 513, 1988; Baichwal and Sugden, In: Gene Transfer, Kucherlapati R, ed., New York, Plenum Press, 117 148, 1986; Temin, In: gene Transfer, Kucherlapati (ed.), New York: Plenum Press, 149 188, 1986).

It is now widely recognized that DNA is introduced into a cell using a variety of viral vectors. In various embodiments, expression constructs comprising viral vectors containing the genes of interest are adenoviral (see for example, U.S. Pat. Nos. 5,824,544; 5,707,618; 5,693,509; 5,670,488; 5,585,362; each incorporated herein by reference), retroviral (see for example, U.S. Pat. Nos. 5,888,502; 5,830,725; 5,770,414; 5,686,278; 4,861,719 each incorporated herein by reference), adenoassociated viral (see for example, U.S. Pat. Nos. 5,474,935; 5,139,941; 5,622,856; 5,658,776; 5,773,289; 5,789,390; 5,834,441; 5,863,541; 5,851,521; 5,252,479 each incorporated herein by reference), an adenoviral-adenoassociated viral hybrid (see for example, U.S. Pat. No. 5,856,152 incorporated herein by reference) or a vaccinia viral or a herpesviral (see for example, U.S. Pat. Nos. 5,879,934; 5,849,571; 5,830,727; 5,661,033; 5,328,688 each incorporated herein by reference) vector.

Non-viral gene transfer include calcium phosphate precipitation (Graham and Van Der Eb, Virology, 52:456-467, 1973; Chen and Okayama, Mol. Cell Biol., 7:2745-2752, 1987; Rippe et al., Mol. Cell Biol., 10:689-695, 1990) DEAE-dextran (Gopal, Mol. Cell Biol., 5:1188-1190, 1985), electroporation (Tur-Kaspa et al., Mol. Cell Biol., 6:716-718, 1986; Potter et al., Proc. Nat. Acad. Sci. USA, 81:7161-7165, 1984), direct microinjection (Harland and Weintraub, J. Cell Biol., 101:1094-1099, 1985.), DNA-loaded liposomes (Nicolau and Sene, Biochim. Biophys. Acta, 721:185-190, 1982; Fraley et al., Proc. Natl. Acad. Sci. USA, 76:3348-3352, 1979; Felgner, Sci Am. 276(6):102 6, 1997; Felgner, Hum Gene Ther. 7(15):1791 3, 1996), cell sonication (Fechheimer et al., Proc. Natl. Acad. Sci. USA, 84:8463-8467, 1987), gene bombardment using high velocity microprojectiles (Yang et al., Proc. Natl. Acad. Sci USA, 87:9568-9572, 1990), and receptor-mediated transfection (Wu and Wu, J. Biol. Chem., 262: 4429-4432, 1987; Wu and Wu, Biochemistry, 27:887-892, 1988; Wu and Wu, Adv. Drug Delivery Rev., 12:159-167, 1993).

Liposomal delivery also is contemplated (Radler et al., Science, 275(5301):810 4, 1997). Also contemplated in the present invention are various commercial approaches involving "lipofection" technology. Complexing the liposome with a hemagglutinating virus (HVJ) facilitates fusion with the cell membrane and promotes cell entry of liposome-encapsulated DNA (Kaneda et al., Science, 243:375-378, 1989). In other exemplary embodiments, the liposome is complexed or employed in conjunction with nuclear nonhistone chromosomal proteins (HMG-1) (Kato et al., J. Biol. Chem., 266: 3361-3364; 1991). In yet further embodiments, the liposome is complexed or employed in conjunction with both HVJ and HMG-1. In that such expression constructs have been successfully employed in transfer and expression of nucleic acid in vitro and in vivo, then they are applicable for the present invention.

Receptor-mediated gene targeting vehicles also are useful and generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987, supra) and transferrin (Wagner et al., Proc. Nat'l. Acad. Sci. USA, 87(9):3410-3414, 1990). Recently, a synthetic neoglycoprotein, which recognizes the same receptor as ASOR, has been used as a gene delivery vehicle (Ferkol et al., FASEB J., 7:1081-1091, 1993; Perales et al., Proc. Natl. Acad. Sci., USA 91:4086-4090, 1994) and epidermal growth factor (EGF) has also been used to deliver genes to squamous carcinoma cells (Myers, EPO 0273085).

In another embodiment of the invention, the expression construct simply consists of naked recombinant DNA or plasmids. Transfer of the construct is performed by any of the methods mentioned above which physically or chemically permeabilize the cell membrane. This is applicable particularly for transfer in vitro, however, it is also applied for in vivo use as well. Dubensky et al. (Proc. Nat. Acad. Sci. USA, 81:7529-7533, 1984; Benvenisty and Neshif (*Proc. Nat. Acad. Sci. USA,* 83:9551-9555, 1986). Naked DNA expression constructs also are transferred using particle bombardment (Klein et al., Nature, 327:70-73, 1987; Yang et al., Proc. Natl. Acad. Sci USA, 87:9568-9572, 1990).

D. Site-Specific Mutagenesis

Site-specific mutagenesis is another technique useful in the preparation of individual LPLA2 proteins used in the methods of the invention. This technique employs specific mutagenesis of the underlying DNA (that encodes the amino acid sequence that is targeted for modification). The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide-sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is useful, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids also are routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization (annealing) conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

Of course, the above described approach for site-directed mutagenesis is not the only method of generating potentially useful mutant LPLA2 protein species and as such is not meant to be limiting. The present invention also contemplates other methods of achieving mutagenesis such as for example, treating the recombinant vectors carrying the gene of interest mutagenic agents, such as hydroxylamine, to obtain sequence variants.

E. Protein Purification

It is desirable to purify the LPLA2 proteins of the invention, for example, for use in formulating medicaments for use in the therapeutic methods of the present invention. Protein purification techniques are well known to those of skill in the art. These techniques involve, at one level, the crude fractionation of the cellular milieu to polypeptide and non-polypeptide fractions. Having separated the LPLA2 proteins/polypeptides of the invention from other proteins, the LPLA2 polypeptides of interest are further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography (FPLC) or even high performance liquid chromatography (HPLC). Exemplary HPLC conditions include those exemplified in Hiraoka et al., J Biol Chem 277, 10090-9, 2002.

Certain aspects of the present invention concern the purification, and in particular embodiments, the substantial purification, of an encoded polypeptide, protein or peptide. The term "purified polypeptide, protein or peptide" as used herein, is intended to refer to a composition, isolated from other components, wherein the polypeptide, protein or peptide is purified to any degree relative to its naturally-obtainable state. A purified polypeptide, protein or peptide therefore also refers to a polypeptide, protein or peptide, free from the environment in which it may naturally occur.

Generally, "purified" will refer to a polypeptide, protein or peptide composition that has been subjected to fractionation to remove various other components, and which composition substantially retains its expressed biological activity. Where the term "substantially purified" is used, this designation refers to a composition in which the polypeptide, protein or peptide forms the major component of the composition, such as constituting about 50%, about 60%, about 70%, about 80%, about 90%, about 95% or more of the proteins in the composition.

Various techniques suitable for use in protein purification well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps is interchangeable, or that certain steps are omitted, and still result in a suitable method for the preparation of a substantially purified polypeptide, protein or peptide.

Methods of Determining Activity of LPLA2

As indicated herein above, the LPLA2 proteins of used herein have transacylase activity. Such an enzyme activity is readily determined using assays known to those of skill in the art. As the LPLA2 proteins is generally specific for PE and PC, the substrates in any transacylase enzyme assay comprise, for example, one or both of these phospholipids. In one aspect, in an exemplary general assay, liposomes comprising dioleoylphosphatidylcholine (60.5 mol %), PE (27.3 mol %) and dicetyl phosphate (12.3 mol %) are used as the acyl group donor for the enzyme being tested. In exemplary assays, such liposomes are formed by mixing constituent lipids in chloroform and drying the mixture under a stream of nitrogen. Fifty mM sodium citrate (pH 4.5) is added to the dried lipids at a volume of 1 ml/128 nmol of lipid phosphorus. The lipids are caused to disperse into the buffer for 8 min in an ice-water bath using a probe sonicator. This procedure creates donor liposomes for the enzyme assay. Those skilled in the art understand that similar liposome commercially available.

Donor liposomes containing e.g., 64 nmol of phospholipid are incubated with 10 mol of N-acetylsphingosine (NAS) or 5 nmol of [$^3$H]NAS (10,000 cpm), 5 µg of bovine serum albumin, and LPLA2 protein containing preparation at 37° C. in a total volume of 500 µl of 40 mM sodium citrate (pH 4.5). The reaction is terminated by adding 3 ml of chloroform/methanol (2:1) plus 0.3 ml of 0.9% (w/v) NaCl. After centrifugation for 5 min at 800×g, the lower layer is transferred into another glass tube and dried down under a stream of nitrogen gas. The lipid extract is then analyzed using e.g., high performance applied thin layer chromatography (HPTLC) to confirm the presence of 1-O-acyl-N-acetylsphingosine (1-O-acyl-NAS). In exemplary embodiments, the HPTLC plate and developed in a solvent system consisting of chloroform/acetic acid (9:1). Of course the lipid catabolism also is readily analyzed using other techniques, such as gas chromatography, HPLC and the like.

In an exemplary embodiment, an HPTLC assay is performed using nonradioactive NAS, the TLC plate is dried, sprayed with 8% (w/v) $CuSO_4$ pentahydrate in water/methanol/concentrated $H_3PO_4$ (60:32:8), and charred for 15 min at 150° C. An image of the plate is taken by a scanner (UMAX Astra Scanner 2200) connected to a computer and scanned by the NIH Image program (Version 1.62) to estimate the density of each band. Known amounts of ceramide are used to obtain a standard curve. In an exemplary assay using radioactive NAS, 1-O-acyl-NAS is detected under a UV light with primulin spray, scraped, and counted. Other assays for enzyme activity are known to those of skill in the art and are readily adapted to determine whether a given LPLA2 variant, fragment or analog possesses the requisite transacylase activity.

In addition to the above in vitro enzyme assays, those skilled in the art also test the activity of any of the LPLA2 protein compositions described herein using immunological assays known in the art. Such immunological assays include determining the presence of a given component of a surfactant prior to and after contacting the surfactant with the LPLA2 protein. In one aspect, surfactant in the test sample is quantified using immunoassays using monoclonal antibodies which recognize surfactant apoproteins. Other exemplary assays for determining the quantity of a pulmonary surfactant are described in e.g., U.S. Pat. Nos. 5,156,950; 5,856,196; 5,670,328; and 5,366,861

As indicated herein throughout, it has been shown that LPLA2 has a biological effect of increasing catabolism of pulmonary surfactant and increased quantities of pulmonary surfactant are present in the clinical condition PAP. Those of skill in the art are aware of a well-known animal model for PAP. This animal model consists of mice that have a targeted deletion of GM-CSF, providing a model of impaired surfactant catabolism. An exemplary such animal model is described e.g., in U.S. Pat. No. 6,019,965; Ikegami et al., Am. J. Physiol. Lung Cell. Mol. Physiol. 270: L650-L658, 1996; Reed et al., Am. J. Respir. Crit. Care Med. 159: A506, 1999). In one aspect, the LPLA2 proteins, fragments, analogs or variants, as well as expression vectors encoding such LPLA2 proteins, fragments, analogs or variants and of stimulators of LPLA2 proteins, fragments, analogs or variants identified as described herein are administered to such an animal model in order to assess whether such compositions have efficacy in treating disorders of surfactant metabolism. Example 1 provides an exemplary protocol for the administration of LPLA2 to such an animal model. Such an assay is readily adapted to test the therapeutic or other compositions of the present invention.

Another specific and novel phospholipidosis model that may be used herein is described in Example 4. More particularly, the model is an lpla2$^{-/-}$ mouse as described for example in Example 4 herein below that was generated by the systemic deletion of the lpla2 gene exon 5, which encodes the lipase motif essential for LPLA2 activity. This model has characteristic features of phospholipidosis including a significant accumulation of phospholipids such as PE and PC in cells such as alveolar macrophages, peritoneal macrophages, and spleen. This model may be used for the study of the phospholipidosis phenotype. In addition, the model will be particularly useful in screening for CAD agents to determine whether or not such agents can overcome the phospholipidosis phenotype or indeed whether or not such agents exacerbate phospholipidosis. The models may be prepared, e.g., as described herein below. The animal model may be treated with LPLA2 protein in combination with other agents to determine the effect administration of LPLA2 protein function in vivo on phospholipidosis.

Treatment of animals with test compounds will involve the administration of the compound, in an appropriate form, to the animal. Administration will be by any route that can be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Given that the alveolar macrophages are a significant site of phospholipids accumulation, delivery of the test agents to lung material is contemplated to be a particularly useful route of administration. Other routes specifically contemplated include systemic intravenous injection, regional administration via blood, cerebrospinal fluid (CSF) or lymph supply and intratumoral injection.

Determining the effectiveness of a compound in vivo may involve a variety of different criteria. Such criteria include, but are not limited to, survival, feeding, activity, and grooming behaviors, inhibition or prevention of inflammatory response, increased enzyme activity level, improvement in immune effector function and improved food intake.

Any of the above assays described above also are used to screen for agonists of LPLA2 activity as described below. The term "agonist" is used throughout this application to indicate any agent that increases the LPLA2 enzyme activity.

Methods of Treating Surfactant Metabolism Disorders

As described herein throughout, it has been discovered that LPLA2 proteins are used to enhance, stimulate, promote or otherwise increase the catabolism of surfactant. As such, the invention provides any LPLA2 that has an activity that is similar to the activity of a protein of SEQ ID NO:2 for use in the treatment of any disorder of surfactant metabolism. In certain aspects, the methods of the invention are useful in the treatment of lung disease. More particularly, the methods of the invention are useful in the treatment of pulmonary alveolar proteinosis. However, it should be understood that in one aspect, the methods of the invention are useful in the treatment of any and all disorders that manifest in an overproduction of phospholipids, and in particular, the phospholipids PC and PE. Further, it the methods of the invention also are useful in the catabolism of other phospholipids including e.g., phosphatidylserine (PS), phosphatidylinositol (PI), phosphatidylglycerol (PG), cardiolipin (CL), a sphingolipid, sphingomyelin (SM), and phosphatidic acid (PA). As described in further detail below, a particular disorder of phospholipid accumulation is phospholipidosis, particularly, for example, drug induced phospholipidosis.

Phospholipidosis is a generalized condition observed in both animals and humans that is characterized by the appearance of concentric lamellar bodies within cells and the intracellular accumulation of phospholipids. Phospholipidosis most commonly occurs in the setting of exposure to certain drugs. These drugs are termed cationic amphiphilic drugs (CADs) and have the following generic characteristics: CADs contain a hydrophilic domain with one or more primary or substituted nitrogen groups that are positively charged at physiological pH (pKa 8.5-10.5), and a hydrophobic moiety consisting of an aromatic or aliphatic ring structure.

There exist four primary features of CAD-induced phospholipidosis. These features include: the excessive accumulation of phospholipids in cells, the presence of lamellar membranous inclusions by unltrastructural analysis, the accumulation of the drug in concert with the increased phospholipids, and the reversibility of the phospholipid accumulation after cessation of drug treatment. There are over 50 clinically relevant CADs that have been reported to induce phospholipidosis [Reasor and Kacew, Exp. Biol. Med., 226: 825-830, 2001]. They include many commonly used therapeutic agents including chloroquine, amiodarone, fluoxetine, imipramine, gentamicin, azithromycin, quinidine, procaine, erythromycin, citalopram, and maprotiline, and tamoxifen. In most cases these effects have been demonstrated in experimental animals. However, amiodarone, fluoxetine, gentamicin, azithromycin, and perhexiline induce clinically significant phospholipidosis in humans.

The induction of phospholipidosis by CADs is dose dependent, and the accumulating phospholipids may be of extracellular or intracellular origin. Phospholipidosis may be present in any tissue, although the liver and lungs are the most common organs involved. CADs accumulate primarily in lysosomes where they inhibit lysosomal phospholipase activity. The lysosomal phospholipase activity is poorly characterized as is the mechanism for CAD induced phospholipase inhibition. Two classes of phospholipids are reported to accumulate in the lungs of amiodarone treated rats. These are phosphatidylcholine (16:0-20:4, 18:1-18:2, and 18:0-20:4 subclasses) and a lysosome specific phospholipid, lysobisphosphatidic acid [Mortuza et al., Biochim. Biophys. Acta, 1631:136-146, 2003]

Two theories have been proposed for the mechanism of phospholipase inhibition. The first theory states that CADs bind directly to phospholipids forming indigestible complexes [van Bembeke et al., Eur. J. Pharmacol., 314:203-214, 1996; Montenez et al., Eur. J. Pharmacol., 314:215-227, 1996]. This theory is supported by the general observation that phospholipidogenic drugs display a greater affinity for interactions with immobilized artificial membranes [Valko et. al., J. Pharm. Sci., 89:1085-1096, 200]. The second theory postulates that CADs inhibit lysosomal phospholipases directly [Carlier et al., Arch. Toxicol. Supp. 7:282-285, 1984]. The first theory is difficult to reconcile with the ubiquitous nature of membrane phospholipids and the specificity of the lysosome as the site of accumulation of undegraded phospholipids. The second hypothesis is difficult to demonstrate in the absence of a specific candidate phospholipase that may serve as the target for CADs.

The functional consequences of phospholipidosis have been documented in a limited number of studies, and are best studied in association with amiodarone induced pulmonary toxicity. For example, the administration of amiodarone to rats and humans is associated with a dose dependent development of phospholipid accumulation and fibrosis [Reasor et al., Toxicol. Appl. Pharmacol., 97:124-133, 1989]. Alveolar macrophages from amiodarone treated rats demonstrate an enhanced formation of interleukin-6 and TNF-oc in response to lipopolysaccharide [Reasor et al., Proc. Soc. Exp. Biol. Med. 211:346-352, 1996]. The inhibition of alveolar macrophages from amiodarone treated rats is associated with impaired phagocytosis to either zymosan or *Candida albicans*. The relationship between the phospholipid accumulation in the lung, liver, kidney, or other tissues seen with CADs, inflammation, and the eventual development of fibrosis in these organs, has been difficult to document. CAD-induced phospholipidosis may be an acquired variant of other forms of phospholipid storage disease. Alveolar proteinosis observed in the setting of GM-CSF deficiency or following exposure to silica or heavy metals may present with a similar clinical phentoype [deMellp Pediatr. Pathol. Mol. Med. 20:413-432, 2001]. In the present invention it is shown that the inhibition of LPLA2 by cationic amphiphilic drugs is the basis for drug-induced phospholipidosis. A further aspect of the present invention is the treatment of such phospholipidosis by overcoming the CAD-induced inhibition of LPLA2. Such treatment may be in the form of administering LPLA2-based protein compositions and/or LPLA2 related gene therapy compositions. Such therapeutic intervention may be introduced in combination with the CAD (the LPLA2-based treatment may be administered before, after or concurrently with the administration of the CAD), in order that the detrimental effects of the CAD treatment (i.e., the phospholipidosis) are diminished, reduced or abrogated whilst the beneficial still providing being able to administer the CAD therapeutic agent to take advantage of the beneficial properties of the CAD. Additional aspects of the invention also include using the discovery that LPLA2 is inhibited by existing CADs thereby leading to phospholipidosis to advantageous screen for and design new CADs that do not have this harmful inhibitory property. Such new screening aspects, as well as transgenic mice and cells for use in such screening are described elsewhere in this specification.

Thus, the invention contemplates methods of treatment that involve administration of LPLA2-based protein compositions and/or LPLA2 gene therapy. Administration of the protein compositions alone are contemplated to be particularly useful. The protein has an acidic pH optimum, is mannose rich, and is localized to lysosomes. The presence of the mannose residues on the protein make it particularly amenable to uptake through mannose-6-phosphate receptors on cells. Thus the compositions of the invention will be useful for the treatment of tissues that possess cells having, or engineered to have mannose-6-phosphate receptors.

In addition, it is contemplated that the peptide/protein-based compositions of the present invention are used in combination with any present treatments for disorders associated with an abnormal presence of surfactant. For example, in certain embodiments, it is contemplated that the methods of the invention are useful in combination with bronchioalveolar lavage (BAL) therapy. Compositions comprising any and all LPLA2 compositions are administered before, after or during such BAL therapy. Protocols for BAL are provides below in the section entitled PATIENT SELECTION AND MONITORING. Thus, in certain aspects, the protein/peptide-based therapeutics of the present invention are used in the treatment of pulmonary alveolar proteinosis. Such exemplary therapeutics are useful in the treatment of any disorder in which treatment benefits from the treatment produces an increase in catabolism of phospholipids. The patient being treated is of any age. Typically, the patient is between the ages of 20-50 years, however, a particularly aggressive form of PAP is known to be fatal in neonates and as such, the compositions and methods of the present invention are contemplated to be particularly useful in the treatment of neonatal disorders of surfactant metabolism.

In one aspect, protocols for the administration of the proteins or compositions encoding the proteins or agonists thereof are similar to the protocols for the administration of any other agent typically administered for a lung disorder. As a general guideline, protocols developed for the administration of any agent for the treatment of lung disease form a starting point for the administration of the proteins of the invention as both proteins are used to stimulate the catabolism of pulmonary surfactants. Thus, the protein-based compositions (e.g., a protein of amino acid sequence of SEQ ID NO:2) are administered via an inhalant or any other mechanism by which a disorder such as asthma is treated. In one aspect, the dosages are determined using an animal model, such as the GM-CSF models known to those of skill in the art, and modified and adapted to use in higher mammals.

Additional Compositions/Procedures to be Administered with LPLA-2-Based Compositions The appropriate management of PAP depends on the age at presentation, severity of symptoms, and anticipated disease course. In certain aspects, any predisposing conditions (e.g., malignancy, infection) are treated because resolution of the primary condition may lead to remission of PAP. Reports exist of spontaneous remission of primary PAP without medical intervention. Treatment of CAP is notoriously difficult. To date no medical therapy has been shown to be of benefit. Therefore, it is contemplated that therapeutic intervention using LPLA2-based compositions alone are in some aspects sufficient to alleviate the symptoms of disorders of surfactant catabolism, and in other aspects the invention provides the administration of the LPLA2 proteins, analogs, variants, fragments and the like may with other agents/therapeutic interventions to produce catabolism of surfactant phospholipids.

In one aspect, the LPLA2 compositions are, for example, administered along with other agents such as e.g., phospholipases, sargramostim (leukine). This is a commercially available preparation of GM-CSF composition, an agent known to have a therapeutic effect on PAP). Typically in adults, 5-20 mcg/kg/d is administered subcutaneously. Additional agents in combination therapy include bronchodilators, particularly if the patient manifests evidence of airway reactivity is present. In other aspects, mucolytic agents, such as acetylcysteine, trypsin, and ambroxol, also are administered.

In other aspects, the therapies of the invention are combined with surgical intervention such as whole-lung lavage by means of bronchoscopy. The mechanism of improvement is unknown but is presumed to be due to removing surfactant buildup or, alternatively, to minimizing the effect of macrophage dysfunction. Lung lavage reduces both symptoms and the risk of opportunistic infections. Other surgical options include the use of extracorporeal membrane oxygenation (ECMO) and lung transplantation. Lung transplantation is an important consideration due to the fact that to date lung transplantation has been the most effective way of alleviating this disease, and the fact that children suffering from CAP have a 100% mortality rate in the absence of such surgical intervention. The combination of the methods of the present invention with surgical intervention is useful in the treatment of neonatal PAP in order to prevent remission of the disorder.

Methods of performing lung lavage also are useful in the combined therapies contemplated herein. Such methods are well known to those of skill in the art. In brief, the procedure involves single-lung ventilation while the contralateral lung is lavaged with saline. A double-lumen endotracheal tube (ETT) is used in older children, which allows simultaneous single lung ventilation and lavage of the contralateral lung under general anesthesia. The degree of improvement associated with this procedure apparently is dependent on the volume of lavage achieved. Sequential lobar lavage with a flexible fiber optic bronchoscope has also been described. This technique is, in one aspect, performed without the use of general anesthesia. Isotonic sodium chloride solution (with or without the addition of heparin) is generally the fluid instilled into the lungs. The patient is ventilated with 100% oxygen, and the dependent lung is filled with 3-5 mL/kg of fluid. This step is performed to determine whether the fluid leaks into the ventilated side with potentially deleterious effects on ventilation and oxygenation. Lavage is repeated until no more sediment material is obtained.

Generally, variable amounts of fluid are retained within the lungs. Usually, only one lung is ravaged in the course of the procedure. Chest percussion has been reported to improve the yield of material when used with lavage. In general, the patient is intermittently suctioned through the ETT after the procedure in an attempt to remove any residual fluid. In one aspect, serum electrolytes is monitored because fluid fluxes may cause electrolyte imbalances. The use of whole-lung lavage is less well established in young infants and newborns, primarily because of the technical difficulties associated with the passage of a necessarily large ETT through a small glottis, as well as a bronchoscope with which to perform the lavage. However, the successful use of this procedure has been described in infants as small as 5 kg. In smaller infants, whole-lung lavage performed while the infant is on cardiopulmonary bypass (CPB) or ECMO is used. Lung lavage with the use of hyperbaric oxygen has also been described. ECMO provides a bridge to lung transplant or allows a more definitive lung lavage in those who are either too critically ill or too small to undergo bronchoscopic lavage.

The combined therapies contemplated herein, i.e., combinations of LPLA2-based compositions with surgery, and/or BAL and/or other medicament, are in one aspect, administered in a combined amount effective to produce an increase in catabolism of surfactant phospholipids. Such a combined administration in some aspects alleviates one or more symptoms that are associated with an abnormally elevated surfactant content. For example, in PAP the symptoms are described below in the PATIENT SELECTION AND MONITORING section. The therapeutic compositions and methods of the present invention alleviate one or more of these symptoms.

To achieve the appropriate therapeutic outcome, either by administration of the LPLA2-related compositions alone or in combination with other therapeutic modalities, one generally administers to the subject the therapeutic protein composition in an amount effective to produce the desired therapeutic outcome, i.e., an alleviation of one or more of the symptoms of the disease.

Patient Selection and Monitoring

In one aspect the patients that receive the treatments of the invention are neonates, as well as adult males and females. In neonates, in the absence of treatment, there is virtually a 100% mortality rate with conventional therapy and lung transplantation appears to be only chance of survival in such children. The peak incidence of PAP occurs in adults aged 20-50 years, although the disorder may occur at any age.

Throughout the treatment regimens of the present invention, the patient is assessed either prior to and/or, during, and/or after, the therapy to monitor for the signs of the disorder being treated, e.g., respiratory distress. Pathophysiologically, in PAP the alveolar airspaces are filled with a dense proteinaceous-lipid fluid mix, this condition is visualized on light microscopy as PAS-positive-staining fluid within the alveoli. This heavy fluid, allied with the loss of alveolar surface tension, leads to increased work of breathing, a diminished surface area for gas diffusion, and ultimately respiratory failure. Typically, both the pulmonary interstitium and airways are relatively spared. Usually, no airway reactivity occurs. Secondary iatrogenic lung damage may occur in the neonatal form as a consequence of the required high levels of ventilator support and high-inspired oxygen concentrations. Surfactant protein B (SP-B) deficient mouse models have been shown to be very sensitive to elevated inhaled oxygen concentrations. The condition may be complicated further by the development of superinfection, which is thought to occur relatively commonly in this condition as a consequence of pulmonary macrophage dysfunction. The patient is monitored for the development or progression of such symptoms.

Congenital alveolar proteinosis (CAP) is a specific and severe form of alveolar proteinosis in which the predominant symptoms, which occur shortly after birth include neonatal respiratory distress, dyspnea, tachypnea, diminished exercise tolerance, feeding difficulty, failure to thrive, and loss of weight. In neonatal respiratory distress, the patient with CAP presents with progressive respiratory failure and marked hypoxemia shortly after birth. The condition initially is indistinguishable from other causes of neonatal respiratory distress, including infant respiratory distress syndrome, congenital pneumonia, sepsis, and some forms of congenital heart disease. Typically, the pregnancy has been uneventful and no early clues indicate the diagnosis, which often is delayed; prolonged ventilator dependence is ascribed to slow resolution of the initial illness, persisting atelectasis, or pneumonia. In both children and young adults the most consistent diagnostic parameter is a shortness of breath on exertion. Various case series show the prevalence of dyspnea in adults with PAP to be from 50-80%. Dyspnea manifests in the initial stages of illness as diminished exercise tolerance. In addition, PAP is associated with a mild cough, occasionally producing thick sputum or solid material. Up to 80% of adults report a cough. Patients with this disorder also manifest a failure to thrive. Although this parameter is most readily observed in younger children and infants, histories of poor weight gain, poor appetite, and malaise is elicited from older children as well. Often, a decreased level of activity and difficulty feeding is observed. In approximately 20% of cases, chest pain is observed in PAP.

In a general physical examination, the patient will manifest failure to thrive or weight loss, other findings may include evidence of a predisposing disease process (e.g., malignancy, infection, immunodeficiency). Another symptom of this disorder is chronic hypoxemic. Examination of the respiratory system may reveal cyanosis and tachypnea. In neonatal alveolar proteinosis respiratory failure will rapidly lead to death.

In infants, CAP also is diagnosed by performing mutation analysis of the SP-B gene, which has been described as being responsible for CAP. The child's parents also is similarly analyzed because CAP is known as an autosomal recessive congenital disorder. Other determinants include low levels of surfactant B in BAL fluid and elevated levels of surfactant proteins A and D (SP-A, SP-D) have been observed in patients with PAP. Elevated levels of lactate dehydrogenase also is evident, usually in the order of 25% greater than the reference range. In complete blood analysis, polycythemia is found as a consequence of chronic hypoxia.

Other diagnoses involve chest radiography. In neonatal-onset form, radiographic appearances are indistinguishable from those of infantile respiratory distress syndrome; both conditions are characterized by a diffuse ground glass appearance and air bronchograms. However, in later-onset PAP, chest radiography typically shows a diffuse infiltrative pattern, which may be concentrated in the perihilar regions or lung bases. A butterfly or batwing appearance similar to pulmonary edema is often present, although cardiomegaly, Kerley B lines, pleural effusions, and other signs of left-sided heart failure are absent. Chest CT scans reveal scattered air space filling. High-resolution chest tomography (HRCT) shows a patchy distribution of air space disease sharply demarcated from normal alveoli, which is said to have a ground glass appearance, consistent with the proteinaceous material present in the alveoli. These images also show interlobular and intralobular septae are thickened and arranged in an irregular manner that has been termed "crazy paving." In some circumstances, reticular interstitial opacities may also be noted. HRCT appearances are said to be characteristic enough as to strongly suggest the diagnosis in the appropriate clinical setting.

Other tests for determining whether a patient is exhibiting the symptoms of PAP include a pulmonary function test, which may show a mildly restrictive pattern of lung disease with slightly diminished functional lung volumes (forced vital capacity [FVC] 31-79% of predicted values) and a diminished carbon monoxide (CO) diffusing capacity (47-62% of predicted).

The procedures for performing the above diagnostic tests are well known to those of skill in the art. For example, frequently, diagnosis and treatment will often involve performing BAL. Diagnostic BAL reveals a milky or opalescent aspirate. In addition, elevated levels of inflammatory cells may suggest infection, as either a primary or a secondary process. In such analyses, the aspirated material stains very strongly positive for PAS, as expected. SP-A and SP-D levels are elevated in BAL fluid from PAP, as compared to healthy volunteers. In addition, markers such as carcinoembryonic antigen (CEA) and CA-19-9 also may be elevated in PAP.

In certain aspects, open lung biopsy, transbronchial biopsies or thoracoscopic procedures are used to assess the presence of PAP. The literature suggests that diagnosis is made reliably by use of transbronchial biopsy, thus obviating the requirement for an open lung biopsy. The classic pathological finding associated with PAP is of eosinophilic fluid-filled alveolar spaces, which stain strongly on PAS staining. Cholesterol crystals are sometimes observed. Alveolar structure generally is well preserved, as are intralobular septae, with some thickening of interlobular septae. No airway involvement occurs. Immunohistochemistry may provide useful information in cases of CAP. Staining for surfactant proteins A, B, C, and D is possible. Levels of SP-B are reduced in CAP, whereas those of SP-A and SP-D are generally elevated. Electron microscopy (EM) may demonstrate lamellar bodies and tubular myelin within the alveolar space in PAP. The EM appearances in CAP differ in that usually no tubular myelin is present.

As the present invention has shown that LPLA2 is specifically expressed in terminally differentiate alveolar macrophages, and that this enzyme is deficient in animals with PAP, this finding will be useful in diagnostic methods. For example, it is contemplated that pulmonary alveolar proteinosis is diagnosed in a test mammal suspected of having said disorder comprising by determining the presence of LPLA2 activity and/or expression in the alveolar macrophages of the mammal. If there is a deficiency noted in this activity or expression as compared to a reference mammal that is known not to have such a disorder, such a deficiency will be diagnostic of PAP. This may involve assaying for expression of the LPLA2. This is performed directly (via, e.g., a PCR and related nucleic acid based assays for LPLA2 sequences), or indirectly, via assaying for LPLA2 enzyme activity in a sample. A diminished LPLA2 expression or activity will be diagnostic of the disorder. Methods of diagnosing a disorder by determining protein activity and/or expression are well known to those of skill in the art and are used in the diagnostic context of the present invention.

In addition to the above patients, it is contemplated that patients undergoing long-term therapy with CADs also may be selected for treatment with the LPLA2-based therapeutics of the present invention.

Methods of Screening for Modulators of LPLA2 and/or Surfactant Catabolism

The present invention also contemplates screening of compounds for their ability to modulate surfactant catabolism. The present invention shows that LPLA2 is responsible for the catabolism of surfactant phospholipids. This activity can, therefore, be used in the treatment of any disorder in which it is desirable to increase phospholipid catabolism. This realization affords those of skill in the art ability to test various compounds for therapeutic activity that increases the activity of LPLA2. In one aspect, selected compounds will be those useful in increasing pulmonary surfactant catabolism. The present section describes screening assays for identifying such compounds. In the screening assays of the present invention, the candidate substance may first be screened for basic biochemical activity—e.g., in vitro stimulation of LPLA2 activity, and then tested for its ability to increase pulmonary surfactant catabolism, at the cellular, tissue or whole animal level. To this effect, animal models of pulmonary surfactant catabolism disorders are known, e.g., model mice that have a mutation in GM-CSF that exhibit symptoms of PAP, as well as SCID mice which may exhibit similar symptoms.

a. Modulators and Assay Formats

The present invention provides methods of screening for modulators of LPLA2 activity. It is contemplated that such screening techniques will prove useful in the identification of compounds that will augment, stimulate or otherwise increase the surfactant catabolism properties of LPLA2 and thus will be useful in the treatment of surfactant catabolism disorders. In these embodiment, the present invention is directed to a method for determining the ability of a candidate substance to modulate phospholipid catabolism, generally including the steps of:

i) contacting a LPLA2 of SEQ ID NO:2 with a candidate modulator;

ii) monitoring the activity of said LPLA2; and iii) comparing the activity of LPLA2 in the presence and absence of said candidate substance; wherein an alteration in the activity of said LPLA2 activity indicates that the substance is a modulator of alveolar phospholipid catabolism. Assays for determining LPLA2 activity are discussed above in the section entitled METHODS OF DETERMINING ACTIVITY OF LPLA2.

In certain aspects, the LPLA2 is an isolated fraction. In certain embodiments, the LPLA2 is expressed in a cell. More particularly, the LPLA2 is recombinantly expressed in the cell.

To identify a candidate substance as being capable of modulating phospholipid catabolism in the assay above, one measures or determines the presence of free surfactant-derived phospholipids, surfactant protein and the like in the absence of the added candidate substance. One then adds the candidate substance to the cell and determine the response in the presence of the candidate substance. A candidate substance which modulates any of these characteristics is indicative of a candidate substance having modulatory activity. In the in vivo screening assays of the present invention, the compound is administered to a model animal, over period of time and in various dosages, and an alleviation of the symptoms associated with pulmonary phospholipid catabolism are monitored. Any improvement in one or more of these symptoms will be indicative of the candidate substance being a useful modulator. It is contemplated that in some aspects the modulator is an inhibitor of the catabolism but more common aspects, the modulator is a stimulator of such catabolism.

As discussed elsewhere in the present specification, there many commonly used therapeutic agents that induce clinically significant phospholipidosis in humans and in other animals [Reasor and Kacew, Exp. Biol. Med., 226:825-830, 2001]. The present invention shows that CADs inhibit LPLA2 activity and that this inhibition leads to the phospholipidosis. The screening assays of the present invention will therefore be particularly useful in identifying whether a given CAD agent will cause phosholipidosis. Such screening assays may be performed on a specific individual before, during and after administration of the CAD in order to determine whether that specific individual will contract phospholipidosis. Additionally, the screening assays will be particularly useful in assisting in the screening and design of new CAD agents that do not have LPLA2 inhibiting activity. Such screening assays may be modified to be performed as high throughput screens in the identification of new drugs.

As used herein the term "candidate substance" refers to any molecule that may potentially act as a modulator of the LPLA2 of the present invention. In certain aspects, the candidate substance is a protein or fragment thereof, a small molecule inhibitor, or even a nucleic acid molecule. Alternatively, useful pharmacological compounds will be compounds that are structurally related to other known modulators of surfactant catabolism. Rational drug design includes not only comparisons with known modulators of phospholipases, but predictions relating to the structure of target molecules.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds molded of active, but otherwise undesirable compounds.

Candidate compounds may include fragments or parts of naturally-occurring compounds or are found as active combinations of known compounds which are otherwise inactive. It is proposed that compounds isolated from natural sources, such as animals, bacteria, fungi, plant sources, including leaves and bark, and marine samples are assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention is a polypeptide, apolynucleotide, a small molecule inhibitor or any other compound that is designed through rational drug design starting from a known activator of a phospholipase A2 activity.

"Effective amounts" in certain circumstances are those amounts effective to reproducibly an alteration in the enzyme activity of LPLA2 and/or alter the expression of LPLA2 in comparison to their normal levels. Compounds that achieve significant appropriate changes in activity and/or expression of LPLA2 will be used.

Significant changes in activity and/or expression will be those that are represented by alterations in activity of at least about 30%-40%, and in some aspects, by changes of at least about 50%, with higher values of course being possible.

In additional assays, the candidate substance is a mutant of LPLA2 activity prepared as described above. Such a mutant is readily tested using an assay for LPLA2 activity, e.g., determining the products of enzyme action.

b. In Vitro Assays

A quick, inexpensive and easy assay to run is a binding assay. Binding of a molecule to a target may, in and of itself, be stimulatory, due to steric, allosteric or charge-charge interactions. In some aspects, this is performed in solution, in other aspects it is performed on a solid phase and is utilized as a first round screen to rapidly eliminate certain compounds before moving into more sophisticated screening assays. In one embodiment of this kind, the screening of compounds that bind to the LPLA2 or fragment thereof is provided.

The target is either free in solution, fixed to support, expressed in or on the surface of a cell. Either the target or the compound is labeled, thereby permitting determining of binding. In another embodiment, the assay may measure the inhibition of binding of a natural substrate of LPLA2 to LPLA2. Competitive binding assays are performed in which one of the agents, e.g., the substrate or the candidate substance is labeled. Usually, the target will be the labeled species, decreasing the chance that the labeling will interfere with the binding moiety's function. One may measure the amount of free label versus bound label to determine binding or inhibition of binding.

A technique for high throughput screening of compounds is described in WO 94/03564. Large numbers of small peptide test compounds are synthesized on a solid substrate, such as plastic pins or some other surface. The peptide test compounds are reacted with, for example, LPLA2 and washed. Bound polypeptide is detected by various methods.

Purified target, such as LPLA2, are coated directly onto plates for use in the aforementioned drug screening techniques. However, non-neutralizing antibodies to the polypeptide are used to immobilize the polypeptide to a solid phase. Also, fusion proteins containing a reactive region (such as, for example, a terminal region) are used to link an active region to a solid phase.

C. In Cyto Assays

Various cell lines that express LPLA2 are utilized for screening of candidate substances to study various functional attributes of candidate compounds. In such assays, the compound is formulated appropriately, given its biochemical nature, and contacted with a target cell.

Depending on the assay, in certain embodiments, cell culture is required. As discussed above, the cell may then be examined by virtue of a number of different physiologic assays (growth, size, morphology etc). Alternatively, molecular analysis is performed in which the function or expression of LPLA2 is explored in the presence and absence of the candidate substance. This involves assays such as those for protein expression, enzyme function, substrate utilization, mRNA expression (including differential display of whole cell or polyA RNA) and others.

For cell-based assays, an exemplary cell that is used in the screening assays of the present invention is an aleveolar cell that has been transformed with LPLA2. In an exemplary assay, a multi-well format assay is set up to determine the phospholipid catabolism properties of such a cell line to identify compounds that alter phospholipid catabolism. Assays to monitor such catabolic activity are described e.g., in Example 1 below.

For cell-free assays, LPLA2 activity is assessed by using a cellular extract containing the LPLA2 protein.

d. In Vivo Assays

The present invention particularly contemplates the use of various animal models. As discussed above, there is a well-characterized transgenic mouse model of PAP and in exemplary embodiments, it is used for screening assays in a whole animal system. This animal model is, therefore, used not only screen for modulators of LPLA2 enzyme activity, but also to track the therapeutic effects of the candidate substance in the treatment of a disorder of surfactant catabolism.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration is by intratracheal instillation, bronchial instillation, intradermal, subcutaneous, intramuscular, intraperitoneal or intravenous injection. Specifically contemplated are bronchial instillation, inhalants and other mechanisms for delivery of the candidate substance locally to the lung tissue.

Determining the effectiveness of a compound in vivo may involve a variety of different criteria. Such criteria include, but are not limited to, survival, reduction of protein excretion, and improvement of general physical state including activity. It also is possible to perform histologic studies on tissues from these mice, or to examine the molecular and morphological state of the cells, which includes cell size, other morphological indicators or alteration in the expression of genes involved in surfactant disorders. The transgenic mouse models described herein will be particularly useful for in vivo screening.

Methods and Compositions for Generating Trangenic Models of Phospholipidosis

In one embodiment of the invention, transgenic animals are produced which have disrupted lpla2 gene. More particularly, the invention provides lpla2$^{-/-}$ mice that generated by the systemic deletion of the lpla2 gene exon 5, which encodes the lipase motif essential for LPLA2 activity. These mice were healthy at birth and fertile, they showed no lysosomal phospholipase A2 activity systemically and, at an early age, showed an accumulation of PE and PC in alveolar macrophages, peritoneal macrophages, and spleen that is characteristic of phospholipidosis. Transgenic animals, recombinant cell lines derived from such animals and transgenic embryos and offspring of these animals may be useful in methods for screening for and identifying agents that induce or repress function of LPLA2 protein. Transgenic animals of the present invention also can be used as models for studying indications of abnormal LPLA2 protein expression.

The transgenic knock-out animal is produced by the integration of the an exogenous gene into the genome in a manner that permits the expression of the ablation, deletion or other silencing of the lpla2 gene exon 5. This deletion results in the deletion of the gene that encodes LPLA2. Methods for producing transgenic animals are generally described by Wagner and Hoppe (U.S. Pat. No. 4,873,191; which is incorporated herein by reference), Brinster et al. Proc Natl Acad Sci USA. 82(13):4438 42, 1985; Hammer et al., Nature. 20 26;315 (6021):680 3, 1985; Palmiter and Brinster, Cell, 41(2): 343 5, 1985 (which are incorporated herein by reference) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

In specific preferred embodiments, it will be desirable to use homologous recombination to create a knock-out vector. To create the specific LPLA2 null mice of the present invention, a targeting vector was designed and constructed containing two loxP sites and two FRT sites with a PGK-neo cassette placed between the FRT sites for modification by use of Cre/loxP and Flp/FRT recombination systems. The vector is then introduced into embryonic cells and the correctly targeted vector is then transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which are characterized by the absence or deletion of the lpla2 gene. These "knock-out" mice permits the study of the effects therapeutic intervention of that phospholipidosis on a cell in vivo. These animals simulate phospholipidosis, a significant abnormality that is shown herein to result from the inhibition of LPLA2 activity. The present invention teaches the production of such a knock-out animal.

The production of the mice and their phenotype is discussed in further detail in the Example 3. Briefly, LPLA2 null mice were created using a targeting vector that contained two loxP sites and two FRT sites with a PGK-neo cassette placed between the FRT sites for modification by use of Cre/loxP and Flp/FRT recombination systems. Exon 5 of lpla2, which encodes for the lipase motif essential for LPLA2 activity, was floxed with two loxP sites, and then inserted into the vector. CJ7 ES cells were electroporated with the linearized targeting vector. Homologous recombinant clones were obtained from G418-resistant colonies screened at a frequency of 20%. A correctly targeted clone was injected into C57BL/6 blastocysts. The chimeric mice were mated with C57BL/6 to obtain heterozygous mice carrying the targeted allele.

The "conditional allele" in which the neo cassette was deleted by using Flp/FRT recombination system. The LPLA2 enzyme activity in the homozygous mice carrying the conditional allele was found to be the same as wild-type mice. EIIa Cre transgenic mice express Cre recombinase in the one-cell zygote stage of embryo under the control of the adenovirus EIIa promoter. Heterozygous mice carrying the conditional allele were mated with EIIa Cre transgenic mice to excise the region containing exon 5. The resultant heterozygous mice carrying the null allele were mated together to generate lpla2$^{-/-}$, lpla2$^{+/-}$, and lpla2$^{+/+}$ littermates. Homologous recombination at the null allele was screened by PCR as described in Example 4.

As noted above, transgenic animals and cell lines derived from such animals may find use in certain testing experiments. In this regard, transgenic animals and cell lines that lack the lpla2 gene (e.g., animals and cells that are lpla2$^{-/-}$ or lpla2$^{+/-}$, may be exposed to test substances. These test substances can be screened for the ability to enhance, replace or upregulate the wild-type LPLA2 protein expression and/or function.

a. Methods of Making Recombinant Cells and Transgenic Animals

As noted above, a particular embodiment of the present invention provides transgenic animals in which the LPLA2 protein has been deleted to create a lpla2 knockouts. The knockout mice have no LPLA2 activity. The genotype distribution lpla2$^{+/-}$ breeding is consistent with the observation that all null mice are viable at birth and survive at least one month post-natally. Mice that are heterozygous for lpla have one-half the phospholipase activity observed in their wild type littermates. Lpla2 null mice display a robust pulmonary phenotype at one month of age with intralysosomal lipid inclusions and a cellular infiltrate in the alveolar septae.

The inventors have demonstrated that the AXSXG sequence within exon 5 of lpla2 is required for enzymatic activity. As such, this exon was targeted with the placement of loxP sites flanking this region. PGKneo was used as a selectable marker. With the recognition that placement of such a marker within intronic sequences of a gene can influence the expression of neighboring genes and the generation of a phenotype that does not reflect the gene of interest, the newly described Flp/FRP system was used for subsequent excision of this marker. The excision was confirmed by the absence of lpla2 activity in the brains of the homozygous null mice. The genotypes of the mice are consistent with the production of viable lpla2 null mice consistent with the interpretation that the absence of lpla2 activity is not associated with embryonic lethality. The mice have been back-crossed four times and preliminary histology has been performed on one month old lpla2$^{-/-}$ mice and their wild type litter mates. A marked mononuclear cell infiltration is observed in the lungs and, to a lesser extent, livers of the null mice.

The transgenic animals of the invention, recombinant cell lines derived from such animals and transgenic embryos may be useful in methods for screening for and identifying agents that repress the phospholipidosis. Additionally, the models and cells may be used in further studying phospholipidosis.

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; which is incorporated herein by reference), Brinster et al. Brinster et al. Proc Natl Acad Sci USA. 82(13):4438 42, 1985; which is incorporated herein by reference in its entirety) and in "Manipulating the Mouse Embryo; A Laboratory Manual" 2nd edition (eds. Hogan, Beddington, Costantimi and Long, Cold Spring Harbor Laboratory Press, 1994; which is incorporated herein by reference in its entirety).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which express a gene of interest.

DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm is a UV spectrophotometer. For microinjection, DNA concentrations are adjusted to 3 µg/ml in 5 mM Tris, pH 7.4 and 0.1 mM EDTA.

Other methods for purification of DNA for microinjection are described in Hogan et al. Manipulating the Mouse Embryo (Cold Spring Harbor Laboratory, Cold Spring Harbor, N.Y., 1986), in Palmiter et al. Nature 300:611 (1982); the Qiagenologist, Application Protocols, 3rd edition, published by Qiagen, Inc., Chatsworth, Calif.; and in Sambrook et al. Molecular Cloning: A Laboratory Manual (Cold Spring Harbor Laboratory, Cold Spring Harbor, N.Y., 1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG;Sigma). Females are placed with males immediately after hCG injection. Twenty-one hours after hCG injection, the mated females are sacrificed by $CO_2$.asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% $CO_2$ 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmaker's forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

In a preferred embodiment, the transgenic mouse models of the invention are created by the technique described in Example 4. Briefly, the genome genome sequence containing the lpla2 gene was obtained. It has now been submitted to GenBank under accession number AY179884. A SmaI-SacI fragment of approximately 8,450 bp of the lpla2 gene was subcloned into the pUC vector. To create the conditional null allele, the SpeI-DraI region containing exon 5 was floxed with two lox P sites, and then inserted into the vector. The PGK neo cassette flanked with two FRT sites was inserted at SpeI site in the intron between exon 4 and 5 in reverse orientation. The targeting vector was linearized and electroporated into CJ7 ES cells. Homologous recombinant clones were then obtained from G418-resistant colonies. The correctly targeted clone was injected into C57BL/6 blastocysts. The chimeric mice were mated with C57BL/6 to obtain heterozygous mice carrying the targeted allele. Mice carrying the targeted allele were mated with flp1 mice (The Jackson Laboratory, stock #3800) to delete the neo cassette. The conditional heterozygous mice were then mated with EIIa Cre mice of C57BL/6 background (The Jackson Laboratory, stock #3724) to excise the region containing exon 5. The heterozygous mice carrying the null allele were mated to generate homozygous (−/−), heterozygous (+/−), and wild-type (+/+) littermates of the lpla2 null allele. Homologous recombination at null allele was screened by PCR as described in Example 4.

b. Monitoring Transgene Expression

In order to determine whether the transgene has been successful incorporated into the genome of the transgenic animal, a variety of different assays may be performed. Transgenic animals can be identified by analyzing their DNA. For this purpose, when the transgenic animal is a rodent, tail samples (1 to 2 cm) can be removed from three week old animals. DNA from these or other samples can then be prepared and analyzed by Southern blot, PCR, or slot blot to detect transgenic founder (F0) animals and their progeny (F1 and F2).

The various F0, F1 and F2 animals that carry a transgene can be analyzed by any of a variety of techniques, including immunohistology, electron microscopy, and making determinations of total and regional area weights. Immunohistological analysis for the expression of a transgene by using an antibody of appropriate specificity can be performed using known methods. Morphometric analyses to determine regional weights, B and/or T cell counts, and cognitive tests to determine dementia characteristics can be performed using known methods.

In immuno-based analyses, it may be necessary to rely on Sax2 protein-binding antibodies. A general review of antibody production techniques is provided elsewhere in the specification.

Transgene expression may be analysed by measuring mRNA levels in a given cell. Messenger RNA can be isolated by any method known in the art, including, but not limited to, the acid guanidinium thiocyanate-phenol:chloroform extraction method, from cell lines and tissues of transgenic animals to determine expression levels by Northern blots, RNAse and nuclease protection assays.

Additionally, transgene expression in a given cell also may be determined through a measurement of protein levels of the cell. Protein levels can be measured by any means known in the art, including, but not limited to, western blot analysis, ELISA and radioimmunoassay, using one or more antibodies specific for the protein encoded by the transgene.

For Western blot analysis, protein fractions can be isolated from tissue homogenates and cell lysates and subjected to Western blot analysis as described by, for example, Harlow et al., Antibodies: A Laboratory Manual, (Cold Spring Harbor, N.Y. 1988).

For example, the protein fractions can be denatured in Laemmli sample buffer and electrophoresed on SDS-Polyacrylamide gels. The proteins are then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of the transgene-encoded proteins.

ELISAs are preferably used in conjunction with the invention. For example, an ELISA assay may be performed where Sax2 protein from a sample is immobilized onto a selected surface, preferably a surface exhibiting a protein affinity such as the wells of a polystyrene microtiter plate. The plate is washed to remove incompletely adsorbed material and the plate is coated with a non-specific protein that is known to be antigenically neutral with regard to the test antibody, such as bovine serum albumin (BSA), casein or solutions of powdered milk. This allows for blocking of nonspecific adsorption sites on the immobilizing surface and thus reduces the background caused by nonspecific binding of antisera onto the surface.

Next, the protein-specific antibody is added to the plate in a manner conducive to immune complex (antigen/antibody) formation. Such conditions preferably include diluting the antisera/antibody with diluents such as BSA bovine gamma globulin (BGG) and phosphate buffered saline (PBS)/Tween®. These added agents also tend to assist in the reduction of nonspecific background the plate is then allowed to incubate for from about 2 to about 4 hr, at temperatures preferably on the order of about 25° to about 27° C. Following incubation, the plate is washed so as to remove non-immunocomplexed material. A preferred washing procedure includes washing with a solution such as PBS/Tween®, or borate buffer.

Following formation of specific immunocomplexes between the sample and antibody, and subsequent washing, the occurrence and amount of immunocomplex formation may be determined by subjecting the plate to a second antibody probe, the second antibody having specificity for the first (usually the Fc portion of the first is the target). To provide a detecting means, the second antibody will preferably have an associated enzyme that will generate a color development upon incubating with an appropriate chromogenic substrate. Thus, for example, one will desire to contact and incubate the antibody-bound surface with a urease or peroxidase-conjugated anti-human IgG for a period of time and under conditions which factor the development of immunocomplex formation (e.g., incubation for 2 hr at room temperature in a PBS-containing solution such as PBS/Tween®.

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and H2O2 in the case of peroxidase as the enzyme label. Quantitation is then achieved by measuring the degree of color generation, e.g., using a visible spectrum spectrophotometer. Variations on this assay, as well as completely different assays (radioimmunprecipitation, immunoaffinity chromatograph, Western blot) also are contemplated as part of the present invention.

Other immunoassays encompassed by the present invention include, but are not limited to those described in U.S. Pat. No. 4,367,110 (double monoclonal antibody sandwich assay) and U.S. Pat. No. 4,452,901 (Western blot). Other assays include immunoprecipitation of labeled ligands and immunocytochemistry, both in vitro and in vivo.

C. Methods of Using Recombinant Cells and Transgenic Animals

The transgenic animals of the present invention include those which have a substantially increased probability of spontaneously developing phospholipidosis when compared with non-transgenic littermates. A "substantially increased" probability of spontaneously developing a particular phenotype means that, a statistically significant increase of measurable symptoms of that phenotype is observed when comparing the transgenic animal with non-transgenic littermates. For example, the tissues of the knock-out mice described herein were analysed and revealed differences in accumulation of phospholipids PC and PE as compared to like animals that do not have an abrograted/deleted or otherwise non-functional lpla2 gene. Other phospholipids discussed herein also may be accumulated by these animals. Exemplary phenotypes of these models may be seen in the electron micrographs depicted in FIG. 2 and in FIG. 6.

It is contemplated that the knockout mice may form one of a battery of screens for manifestations of phospholipidosis and for serving as a screen for identifying agents that improve the phospholipidosis phenotype. For example, the transgenic mice of the invention may be used in combination with for example, the transgenic mice that are models of PAP discussed above.

Coding regions for use in constructing the transgenic mice include the coding region for LPLA2 protein. Additionally, it is contemplated that transgenic mice also may be constructed using coding regions which encode a complete polypeptide, or a fragment thereof, as long as the desired function of the polypeptide is retained. The coding regions for use in constructing the transgenes of the present invention further include those containing mutations, including silent mutations, mutations resulting in a more active protein, mutations that result in a constitutively active protein, and mutations resulting in a protein with reduced activity.

The transgenic mice of the present invention have a variety of different uses. First, by creating an animal model in which the lpla2 is deleted, the present inventors have provided a living "vessel" in which the function of LPLA2 protein replacement may be further dissected. Additionally, the animals provide a vehicle for testing non-LPLA2 protein related drugs that may ameliorate phospholipidosis. These animals further provide a model of the disease itself, such that the mice will be suitable for more detailed studies on the pathology and pathophysiology of drug induced phospholipidosis. Such a model is valuable because it may allow one to understand the mechanisms that link phospholipid accumulation to inflammation and fibrosis. Thus, the transgenic mouse provides a novel model for the study of phospholipidosis as well as LPLA2-associated disorders. This model could be exploited by treating the animal with compounds that potentially enhance or upregulate the in vivo action of LPLA2 protein and treat lipidosis and related disorders.

In the context of CAD-induced phospholipidosis, the association between long-term treatment with CADs and the development of pulmonary inflammation and fibrosis has been long recognized. However, until the present invention, no mechanism has been demonstrated that explains the pathogenesis of the inflammation. The mice of the present invention can now be employed to perform mouse cytokine gene array analysis and ELISAs to ascertain the cytokine and chemokine profile in wild type and lpla2 null mice. Various methods can be used for obtaining material for cytokine analyses. These methods include bronchoalveolar lavage (1 ml fluid with 0.5 ml recovery on average), in vitro cultures of alveolar macrophages (96 well cultures), and aqueous extraction of lung tissue (normalized for total protein). These methods enable the skilled person to ascertain the cytokine profile over time and the relative contributions of the macrophages compared to other inflammatory cells. The mice will be used to assess whether the alveolar macrophages from the lpla2$^{-/-}$ mice demonstrate increased EL6 and TNFa.

Additionally, the susceptibility of lpla2$^{+/+}$, lpla2$^{+/-}$, and lpla2$^{-/-}$ mice to CADs can be determined based on their different levels of alveolar macrophage lpla2 activity. In certain exemplary embodiments, mice that vary in their endogenous activity of lpla2 are treated with a CAD and sensitivity to the drug is monitored to determine whether sensitivity to the drug corresponded to the endogenous activity.

In addition, the mice will be treated with as CADs mediate their toxicity through inhibition of LPLA2 activity, administration of lysosomal phospholipase A2 will reverse the pulmonary phospholipidotic phenotype. Macrophage associated lysosomal enzymes are targeted in many storage disorders including Gaucher and Fabry disease. The presence of mannose groups on the lysosomal enzymes and mannose receptors on the macrophages allows for the cellular uptake and trafficking to lysosomes, often with beneficial effects. The ability to redirect lpla2 to the alveolar macrophages of null mice and to prevent or reverse the pulmonary phenotype can be used to corroborate that LPLA2 mediates the effects of phospholipidosis. This can be performed by two exemplary methods, in the first, bone marrow transplantation can be used in which wild-type mouse bone marrow will be compared to that from lpla2$^{-/-}$ mice. Only the wild-type marrow will rescue the affected mice. Additionally, bone marrow transplants of wild-type mice with the marrow from lpla2$^{-/-}$ results in the development of phospholipidosis as well. These experiments establish that LPLA2 activity is sufficient for preventing the development of phospholipidosis in the setting of CAD therapy.

In the second method, the role of LPLA2 in surfactant homeostasis can be further discerned by directing the synthesis of the lysosomal phospholipase A2 in the respiratory epithelium of lpla2$^{-/-}$ mice with a chimeric gene under the control of the promoter from the human surfactant protein-C (SP-C). Bi-transgenic mice bearing the SP-C-LPLA2 construct can be created on a background of lpla$^{2-/-}$ to determine whether expression of the phospholipase A2 corrects the alveolar proteinosis/phospholipidosis.

Pharmaceutical Compositions

Pharmaceutical compositions for administration according to the present invention can comprise at least one LPLA2-derived protein (e.g., a protein of SEQ ID NO:2, a variant or analog thereof or any other LPLA2-derived protein that stimulates the breakdown of one or more phospholipids). The pharmaceutical compositions also include another agent that is used for the treatment of a disorders of surfactant metabolism, e.g., bronchodilators, particularly if the patient manifests evidence of airway reactivity is present as well as, mucolytic agents such as acetylcysteine, trypsin, and ambroxol, and/or GM-CSF. Each of these preparations is in some aspects provided in a pharmaceutically acceptable form optionally combined with a pharmaceutically acceptable carrier. These compositions are administered by any methods that achieve their intended purposes. Individualized amounts and regimens for the administration of the compositions for the stimulation, augmentation, or other increase in the catabolism of pulmonary surfactant using the methods of the present invention are determined readily by those with ordinary skill in the art using assays that are used for the diagnosis of the disorder and determining the level of effect a given therapeutic intervention produces.

Any of the protocols, formulations, routes of administration and the like that have previously been used in the treatment of lung disorders may readily be modified for use in the present invention. In some cases, mechanical ventilation is appropriate, especially in children with CAP. Such ventilation may include high-frequency oscillatory ventilation (HFOV) or other unconventional forms of mechanical ventilation. Theoretically, partial liquid ventilation (PLV) offers the advantage of lung lavage combined with ventilator support.

Compositions within the scope of this invention include all compositions comprising at least one LPLA2-derived protein according to the present invention in an amount effective to achieve its intended purpose of promoting, stimulating, increasing or otherwise inducing catabolism of pulmonary surfactant. In some aspects, such treatment will result in an alleviation of one or more symptoms of PAP discussed above. In other aspects, the LPLA-2 derived protein compositions used in the present invention are administered using an inhalant or orally.

It is understood that the suitable dose of a composition according to the present invention will depend upon the age, health and weight of the recipient, kind of concurrent treatment, if any, frequency of treatment, and the nature of the effect desired. However, the dosage is tailored to the individual subject, as is understood and determinable by one of skill in the art, without undue experimentation. This typically involves adjustment of a standard dose, e.g., reduction of the dose if the patient has a low body weight.

The total dose of therapeutic agent is administered in multiple doses or in a single dose. In certain embodiments, the compositions are administered alone, in other embodiments the compositions are administered in conjunction with other therapeutics directed to the disease or directed to other symptoms thereof.

In some aspects, the compositions of the invention are formulated into suitable pharmaceutical compositions, i.e., in a form appropriate for in vivo applications in the therapeutic intervention of surfactant metabolism disorders. Generally, this will entail preparing compositions that are essentially free of pyrogens, as well as other impurities that could be harmful to humans or animals. In some aspects, the compositions are prepared for administration directly to the lung. These formulations are for oral administration via an inhalant, however, other routes of administration are contemplated (e.g. injection and the like). The finding that LPLA2 is selectively and highly expressed in alveolar macrophages but not in peritoneal macrophages, peripheral blood monocytes, or other tissues leads to a conclusion that a main site of LPLA-2 action is specific to the alveolar macrophage. As such, it is contemplated that formulations and routes of administration that facilitate the peptide/protein compositions to readily be administered to lung tissue will be particularly useful. Receptor-mediated uptake into lung tissue are especially useful.

One will generally desire to employ appropriate salts and buffers to render the compositions stable and allow for uptake of the compositions at the target site. Generally the protein compositions of the invention are provided in lyophilized form to be reconstituted prior to administration. Alternatively, the LPLA-2 derived protein compositions are likely formulated into tablet form. Buffers and solutions for the reconstitution of the therapeutic agents may be provided along with the pharmaceutical formulation to produce aqueous compositions of the present invention for administration. Such aqueous compositions will comprise an effective amount of each of the therapeutic agents being used, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the therapeutic compositions, its use in therapeutic compositions is contemplated. Supplementary active ingredients also are incorporated into the compositions.

Methods of formulating proteins and peptides for therapeutic administration also are known to those of skill in the art. Administration of these compositions according to the present invention will be via any common route so long as the target tissue is available via that route. Most commonly, these compositions are formulated for oral administration, such as by an inhalant. However, other conventional routes of administration, e.g., by subcutaneous, intravenous, intradermal, intramusclar, intramammary, intraperitoneal, intrathecal, intraocular, retrobulbar, intrapulmonary (e.g., term release), aerosol, sublingual, nasal, anal, vaginal, or transdermal delivery, or by surgical implantation at a particular site also is used particularly when oral administration is problematic. The treatment may consist of a single dose or a plurality of doses over a period of time.

In certain embodiments, the active compounds are prepared for administration as solutions of free base or pharmacologically acceptable salts in water suitably mixed with a surfactant, such as hydroxypropylcellulose. Dispersions also are prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. In some aspects, the carrier is a solvent or dispersion medium containing, for example, water, ethanol, polyol (for example, glycerol, propylene glycol, and liquid polyethylene glycol, and the like), suitable mixtures thereof, and vegetable oils. The proper fluidity is maintained, for example, by the use of a coating, such as lecithin, by the maintenance of the required particle size in the case of dispersion and by the use of surfactants. The prevention of the action of microorganisms is brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions is brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also are incorporated into the compositions.

In some aspects, the compositions of the present invention are formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also are derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered if necessary and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. In certain embodiment, parenteral administration of the therapeutic compounds is carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. Such formulations may influence the physical state, stability, rate of in vivo release and rate of in vivo clearance of the administered agents. Depending on the route of administration, a suitable dose is calculated according to body weight, body surface areas or organ size. The availability of animal models is particularly useful in facilitating a determination of appropriate dosages of a given therapeutic. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Typically, appropriate dosages are ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

It will be appreciated that the pharmaceutical compositions and treatment methods of the invention are useful in fields of human medicine and veterinary medicine. Thus the subject to be treated is a mammal, such as a human or other mammalian animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese.

The present invention also contemplated kits for use in the treatment of disorders of surfactant metabolism. Such kits include at least a first composition comprising the proteins/peptides described above in a pharmaceutically acceptable carrier. Another component is a second therapeutic agent for the treatment of the disorder along with suitable container and vehicles for administrations of the therapeutic compositions. The kits may additionally comprise solutions or buffers for effecting the delivery of the first and second compositions. The kits may further comprise additional compositions which contain further stimulators of phospholipid catabolism e.g., additional other phospholipase proteins, mucolytic agents, hematopoeitic factors and the like. The kits may further comprise catheters, syringes or other delivering devices for the delivery of one or more of the compositions used in the methods of the invention. The kits may further comprise instructions containing administration protocols for the therapeutic regimens.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus are considered to constitute certain aspects for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

The following Example provides exemplary materials and methods employed to determine the expression and function of LPLA2.

Reagents

Phosphatidylethanolamine (PE), 1,2-dioleoyl-sn-glycero-3-phosphorylcholine (DOPC) and 1,2-dipalmitoyl-sn-glycero-3-phosphorylcholine (DPPC) were obtained from Avanti Polar Lipids (Alabaster, Ala.). Dicetyl phosphate and monoclonal anti-c-myc clone 9E10 mouse ascites fluid were purchased from Sigma (St. Louis, Mo.); MJ33 was from Calbiochem (San Diego, Calif.); N-Acetyl-D-erythro-sphingosine (NAS) was from Matreya (Pleasant Gap, Pa.). BCA protein assay reagent was obtained from Pierce (Rockford, Ill.).

Isolation of Rat Cells and Tissues

Respiratory disease-free female Wistar rats (125-150 g) were obtained from Charles River Laboratories, Inc. (Portage, Mich.) and housed under specific pathogen-free conditions. For isolation of alveolar macrophages by broncheoalveolar lavage, lavage buffer consisting of 0.15 M NaCl, 2.7 mM EDTA, 20 mM Hepes (pH 7.4), 5.5 mM dextrose, 1× antibiotic-antimycotic sol. (Invitrogen, Calif.) was used. Following anesthesia with subcutaneous sodium pentobarbital, lungs were surgically excised and lavaged as reported. Peritoneal macrophages were obtained by lavage of peritoneal spaces with RPMI 1640 medium containing 1× antibiotic-antimycotic. Contaminated erythrocytes were removed by hypotonic lysis. Peripheral blood monocytes were isolated by centrifugation with Histopaque-1077 (Sigma, Mo.).

Cells were suspended in RPMI 1640 medium containing 1× antibiotic-antimycotic after counting number and plated in 100 mm culture dishes followed by incubation at 37° C. in a humidified atmosphere of 5% $CO_2$ in air. After 1 h, non-adherent cells were removed by washing with phosphate buffered saline. Ninety-five percent of alveolar lavaged cells and 81% of peritoneal lavaged cells in the resultant adherent cell population were macrophages (Coffey et al., J Biol Chem 267, 570-6, 1992). Greater than 90% of adherent peripheral blood mononuclear cells were monocytes Coffey et al., J. Immunol 165, 3592-8, 2000).

Isolation of Mouse Cells and Tissues

Wild-type C57BL/6 mice were obtained from Jackson Laboratory (Bar Harbor, Me.). GM-CSF(−/−) was generated by Dranoff et al. (Science, 264, 713-6, 1994). Bitransgenic mice were generated from GM-CSF(−/−) mice by transgenic expression of a chimeric gene containing GM-CSF under the surfactant protein C(SP-C) promoter (SP-C-GM mice) (Huffman et al. J Clin Invest 97, 649-55 1996). The specificity of the SP-C promoter results in targeted expression of GM-CSF by type II alveolar epithelial cells. Founder GM-CSF(−/−) and SP-C-GM mice were kindly provided by Dr. J. Whitsett (Children's Hospital, Cincinnati, Ohio). After anesthesia with intraperitoneal sodium pentobarbital, the trachea was cannulated and the lung was lavaged with phosphate buffered saline containing 0.5 mM EDTA as previously described (Paine, 3rd et al., J Immunol 164, 2602-9, 2000). The lavage fluid of each group was pooled, and the cell pellet was collected by centrifugation. All mice were housed in specific pathogen-free conditions. Mice were used at 3-5 months of age. All experiments were approved by the University of Michigan Committee on the Use and Care of Animals.

RNA Extraction and cDNA Synthesis

Total RNA was extracted from each rat organ using TRIzol reagent (Invitrogen) followed by purification using RNeasy kit (Qiagen). For isolated cells, total RNA was extracted using RNeasy kit. Total RNA was used to synthesize cDNA with oligo(dT)$_{12-18}$ primers using Super Script First Stand synthesis system (Invitrogen).

Primers and Standard Plasmid for Real Time PCR

Primers were designed from the LPLA2 (GenBank accession #AY490816), Prdx6 (#NM053576), and iPLA2 (XM346803) gene sequences respectively. The rat iPLA2 gene sequence was deduced from its amino acid sequence (#P97570). Primers sequences were matched to both rat and mouse sequences. The primer sets were as follows: LPLA2 forward (5'-ACATGCTCTACTTTCTGCAGCGG-3' SEQ ID NO:3) and reverse (5'-AGAAGCACACGTTTCAGATA-3' SEQ ID NO:4), Prdx6 forward (5'-CAGTGTGCACCA-CAGAACTTG-3' SEQ ID NO:5) and reverse (5'-AGCTCTTTGGTGAAGACTCCT-3' SEQ ID NO:6), iPLA2 forward (5'-ACTACATCTGGCCTGCCGCAA-3' SEQ ID NO:7) and reverse (5'-AGAAGCATTCGGGCCATCTC-3' SEQ ID NO:8).

Standard plasmids were generated with respective the PCR products of LPLA2, Prdx6, and iPLA2 ligated into the pCR4-TOPO vector (Invitrogen) and followed by cloning, purification, quantification, and sequencing.

Quantitative Analysis of the LPLA2, Prdx 6, and iPLA2 mRNA Expression by Real Time PCR A standard curve for each primer set was generated by a serial dilution of a TOPO vector containing each partial gene sequence. One μl of synthesized cDNA mixture was used for a real-time PCR. The Expand High Fidelity PCR system (Roche) containing SYBR Green (Molecular Probes) was used for PCR reaction mixture. The PCR amplifications employed 40 cycles with steps at 94° C. for 30 sec, 60° C. for 30 sec, and 72° C. for 1 min. The iCycler instrument (BioRad laboratories, CA) was used to perform PCR and analyze data. The quality and quantity of each RNA were determined by Agilent Bioanalyzer (Agilent Technologies). The mRNA concentrations were corrected with total RNA.

Preparation of the Soluble Fraction from Rat Alveolar and Peritoneal Macrophages, Peripheral Blood Mononuclear Cells and Tissues.

In preparation of the soluble fractions of alveolar macrophages, peritoneal macrophages, and peripheral blood monocytes, the adherent cells on the culture dishes were washed three times with 8 ml of cold phosphate buffered saline, scraped with a small volume of phosphate buffered saline and transferred into a 15 ml plastic tube. The cells were collected by centrifuge at 800 g for 10 min at 4° C., re-suspended with 0.4-1.0 ml of cold 0.25 M sucrose, 10 mM Hepes (pH 7.4), 1 mM EDTA and disrupted by a probe type sonicator for 10 sec×5 at 0° C. The suspension was centrifuged for 1 h at 100,000 g at 4° C. The resultant supernatant was passed through a 0.2 μm filter and used as a soluble fraction.

In preparation of rat tissue soluble fraction, each tissue was washed with cold PBS, weighed and homogenized by a Potter Elvehjem-type homogenizer with cold 0.25 M sucrose, 10 mM Hepes (pH 7.4), 1 mM EDTA to obtain 10% homogenate. The homogenate was centrifuged for 10 min at 600 g at 4° C. The resultant supernatant was sonicated by a probe type sonicator for 10 sec×5 at 0° C. and centrifuged for 1 h at 100,000 g at 4° C. The supernatant was passed through 0.2 µm filter and used as a soluble fraction.

In preparation of the soluble fraction of mouse alveolar macrophages, the macrophages were collected from wild-type (C57BL/6), GM-CSF (−/−), and SP-C-GM mice by whole lung lavage and were pooled as describe above. The cell pellets were washed 3 times with cold phosphate buffered saline and resuspended in cold 0.25 M sucrose, 10 mM Hepes (pH 7.4), 1 mM EDTA. The suspension was disrupted by a probe type sonicator and followed the same procedure as described above.

Enzyme Assay (Transacylase Activity).

Phospholipids, DOPC and PE, and N-acetylsphingosine (NAS) were used in the assay system as a donor and an acceptor, respectively, of an acyl group. The transacylase activity was determined by analysis of 1-O-acyl-N-acetyl-sphingosine formation rate. The reaction mixture consisted of 45 mM sodium citrate (pH 4.5), 10 µg/ml bovine serum albumin, 40 µM NAS incorporated into phospholipid liposomes (DOPC/PE/dicetyl phosphate/NAS (5:2:1:2 in molar ratio)) and soluble fraction (0.7-10 µg) in a total volume of 500 µl. The reaction was initiated by adding the soluble fraction, kept for 5-60 min at 37° C. and terminated by adding 3 ml of chloroform/methanol (2:1) plus 0.3 ml of 0.9% (w/v) NaCl. The mixture was centrifuged for 5 min at room temperature. The resultant lower layer was transferred into another glass tube and dried down under a stream of nitrogen gas. The dried lipid dissolved in 40 µl of chloroform/methanol (2:1) was applied on an HPTLC plate and developed in a solvent system consisting of chloroform/acetic acid (9:1). The plated was dried down and soaked in 8% (w/v) $CuSO_4$, $5H_2O$, 6.8% (v/v) $H_3PO_4$, 32% (v/v) methanol. The uniformly wet plate was briefly dried down by a hair dryer and charred for 15 min in a 150° C. oven. The plate was scanned and the amount of the reaction products was estimated by NIH-image 1.62.

Immunoblotting

The soluble fraction was precipitated by the method of Bensadoun and Weinstein (Anal Biochem 70, 241-50, 1976). The resultant pellet was dissolved with 30 µl of loading buffer plus 1.5 µl of 2 M Tris for SDS polyacrylamide gel electrophoresis. Proteins were separated using a 12% acrylamide gel and transferred to a PVDF membrane using the transfer buffer (20 mM Tris, 150 mM glycine in 20% methanol) at constant voltage 100 volts for 3 h at 4° C. The membrane was incubated with an anti-mouse LPLA2 peptide ($^{100}$RTSRATQFPD; SEQ ID NO:9) rabbit serum and monoclonal anti-c-myc mouse ascites fluid. The antigen-antibody complex on the membrane was visualized with an anti-rabbit IgG HRP-conjugated goat antibody or an anti-mouse IgG HRP-conjugated goat antibody using diaminobenzidene and hydrogen peroxide.

In addition, it has been confirmed that anti-mouse LPLA2 peptide ($^{100}$RTSRATQFPD; SEQ ID NO:9) rabbit serum is able to recognize human and bovine LPLA2s as well as mouse LPLA2 in immunoblotting in spite of the fact that there are some replacement amino acid residues between LPLA2 species. The alanine residue in mouse LPLA2 peptide, $^{100}$RTSRATQFPD (SEQ ID NO:9), is replaced by threonine in rat and bovine LPLA2s.

Example 2

LPLA2 is Responsible for Pulmonary Surfactant Catabolism

The following Example provides studies which show the robust expression of an acidic lysosomal phospholipase A2 within the alveolar macrophage, the primary site of surfactant degradation. The low expression and activity of this phospholipase A2 in a model of pulmonary alveolar proteinosis demonstrated that this phospholipase likely mediates human disorders associated with abnormal surfactant metabolism.

A series of tissues from the Wistar rat were isolated and assayed for lysosomal phospholipase A2 activity. To assess the distribution of LPLA2 transacylase activity in rat tissues and macrophages, the soluble fraction obtained from each tissue (20 µg of protein/ml) and alveolar macrophages (AM), peritoneal macrophages (PM), or peripheral blood monocytes (PBM) (2 µg of protein/ml) were assayed in citrate buffer, pH 4.5, with 40 µM N-acetyl-sphingosine (NAS) and the enzyme activity was measured as the formation of 1-O-acyl-NAS as described in the Example 1. For lung, the tissue was processed after the macrophages were obtained by broncheoalveolar lavage. Because the lysosomal phospholipase A2 can transacylate ceramide in the 1-hydroxyl position, the transacylase activity was determined as the formation of 1-O-acyl-N-acetylsphingosine (1-O-acyl-NAS). The enzyme activity was comparable in a wide range of tissues including brain, kidney, spleen, thymus, and lung. Of the tissues assayed, the specific activity was highest in thymus and spleen, suggestive that hematopoetic cells might be a source of higher enzyme activity. Pulmonary alveolar macrophages were next studied. When pulmonary alveolar macrophages were isolated by broncheoalveolar lavage and assayed for phospholipase A2 activity, a greater than 40-fold higher activity of the lipase was observed. This difference was not present in either peritoneal macrophages or peripheral blood monocytes.

A comparison of the enzyme activity between peritoneal macrophages, peripheral blood monocytes, and alveolar macrophages was made. The higher LPLA2 activity in alveolar macrophages compared to peritoneal macrophages and monocytes was evidenced by the formation of 1-O-acyl-N-acetylsphingosine and free fatty acid. Transacylase and phospholipase A2 activities in the soluble fraction obtained from rat alveolar macrophages (AM), peritoneal macrophages (PM) and peripheral blood monocytes (PBM) were determined by assaying the soluble cell fractions obtained from AM (1.8 µg protein/ml), PM (6.0 µg protein/ml), and PBM (18 µg protein/ml) in citrate buffer, pH 4.5, with 40 µM N-acetyl-sphingosine (NAS). The formation of 1-O-acyl-NAS and free fatty acid was determined following extraction and separation by thin layer chromatography as described in Example 1.

Time-dependent formation of 1-O-acyl-N-acetylsphingosine in rat macrophages and monocytes also was assessed. Because the initial velocity of the reaction in the alveolar macrophage was significantly greater than that observed in other cells and tissues, the reaction time was shortened to 5 minutes from 30 minutes and the assay protein lowered to 0.9 µg from 10 µg. Under these conditions, the phospholipase A2 activity was linear. The enzyme activities in the peritoneal macrophages and monocytes were slightly higher but comparable to those observed in the other tissues and significantly less than that measured in the alveolar macrophages. These data suggest that elevated lysosomal phospholipase A2 is a marker of the terminally differentiated alveolar macrophage.

The mRNA expression of LPLA2 in the tissues and macrophages also was evaluated using real time PCR. mRNA levels of lysosomal phospholipase A2, peroxiredoxin 6 and cytosolic calcium-independent phospholipase A2 in rat tissue was determined using real time PCR to measure the mRNA of LPLA2, peroxiredoxin 6 (Prdx6), and iPLA2 in each tissue or cell type as described in Example 1. A good correspondence was observed in the mRNA levels normalized to total RNA and the transacylase/phospholipase A2 activity. A comparison was also made between LPLA2 and another reported acidic phospholipase A2. This phospholipase, termed aiPLA2, was identified as the same protein as 1-cys-peroxiredoxin (PRDX6), a non-selenium glutathione peroxidase (Kim et al., Am J Physiol 274, L750-61, May, 1998; Chen et al. *J Biol Chem* 275, 28421-7, 2000). The mRNA levels of PRDX6 were not significantly greater in the alveolar macrophage compared to other tissues. Another macrophage associated phospholipase A2 is the calcium independent group VIA enzyme termed iPLA2 (Winstead et al., Biochim Biophys Acta 1488, 28-39, 2000). mRNA levels of iPLA2 were also not significantly greater in the alveolar macrophage compared to other tissues.

Further studies were performed to demonstrate that the high transacylase/phospholipase A2 activity present in the alveolar macrophage was in fact LPLA2. A polyclonal antibody was raised to a peptide corresponding to the sequence $^{100}$RTSRATQFPD (SEQ ID NO:9) of the mouse LPLA2 protein. An immunoblot of the soluble protein fractions of rat peritoneal and alveolar macrophages was compared to that of c-myc-tagged mouse LPLA2 expressed in COS-7 cells. Immunoblot analysis of the soluble fraction of AM and PM was performed by separating the soluble cell fraction (20 µg of total protein) obtained from AM, PM, and c-myc-tagged mouse LPLA2 over-expressed COS7 cells by SDS polyacrylamide gel electrophoresis and subjected to immunoblotting with a rabbit polyclonal antibody raised to mouse LPLA2 peptide ($^{100}$RTSRATQFPD; SEQ ID NO:9) and a monoclonal antibody to c-myc. LPLA2 and c-myc-tagged LPLA2 were detected as described in Example 1. mLPLA2 denotes c-myc-tagged mouse LPLA2 expressed in COS7 cells. The immunoblot identified a major band in the alveolar macrophage protein fraction of the predicted molecular weight. No corresponding band was detected in the peritoneal macrophage fraction. The antibody recognized the c-myc-tagged protein as well. The identity of the c-myc-LPLA2 was confirmed with an anti-c-myc antibody. Densitometric measurements of the AM and mLPLA2 lanes from the immunoblot analyses was assessed demonstrated a ratio of 1:0.57 between the alveolar macrophage LPLA2 and the mouse LPLA2.

A comparison of reaction velocities was also made between the endogenous enzyme and the expressed LPLA2. The transacylase activity of the soluble fraction of AM was compared with that of mLPLA2 and showed that the ratio of the initial velocity of 1-O-acyl-NAS formation in the AM soluble fraction to that of mLPLA2 soluble fraction was 1:0.58. These data suggest that the transacylase/phospholipase A2 activity measured in the alveolar macrophage was due to LPLA2.

The transacylase and phospholipase A2 activities in the alveolar macrophage were further evaluated for their calcium dependence and pH optima. The effect of pH and calcium on the transacylase activity in rat AM was assessed by assaying the soluble fraction (1.50 µg of protein/ml) of rat AM in 47 mM sodium citrate (pH 4.5) or in 150 mM NaCl, 10 mM Tris-HCl (pH 7.4) with 40 µM NAS at 37° C. for specific time periods. Under the neutral conditions, the reaction mixture containing 1 mM EDTA or 1 mM $CaCl_2$ was used for the assay. The reaction products were separated by thin layer chromatography as described in Example 1. No phospholipase A2 or transacylase activities were observed at pH 7.4 in the presence or absence of calcium. The absence of activity persisted even when the reaction was followed for up to 60 minutes. At pH 4.5 both the formation of 1-O-acyl-N-acetylsphingosine and free fatty acid were observed. The majority of pulmonary surfactant phospholipid is in the form of dipalmitoylphosphatidylcholine. Thus it is demonstrable that this disaturated lipid is a suitable substrate for LPLA2. Dipalmitoylphosphatidylcholine has a phase transition temperature of 41° C. Therefore, liposomes containing dioleoylphosphatidylcholine, dipalmitoylphosphatidylcholine and dicetyl phosphate were used. Degradation of dipalmitoylphosphatydylcholine by rat alveolar macrophages was assessed by incubating the soluble fraction (3.14 µg of protein/mg) of rat AM in citrate buffer, pH 4.5, with 130 µM phospholipid in liposomes consisting of DOPC: DPPC: dicetyl phosphate (the molar ratio of 3.07:3.07:1) at 37° C. for varying time periods. The released free fatty acids in the reaction were separated by a silver nitrate impregnated HPTLC plate that was developed a solvent system consisting of chloroform/acetic acid (95:5). The free fatty acid released by the soluble fraction was corrected by subtracting the fatty acid released in the absence of the soluble fraction at each time point and plotted against incubation time. Under these conditions and in the absence of N-acetylsphingosine as an acceptor, the release of both palmitic acid and oleic acid was observed.

In initial characterizations, LPLA2 was noted as being insensitive to the phospholipase A2 inhibitors bromoenol lactone and nonadecyltetraenyl trifluoromethyl ketone. However, MJ33, an inhibitor demonstrated to block surfactant phosphatidylcholine catabolism in vivo, was not evaluated. In the studies the effect of MJ33 on LPLA2 transacylation activity in rat alveolar macrophages and c-myc-tagged mouse LPLA2 transfected COS 7 cells was also determined. The soluble fraction (2.42 µg of protein/ml) prepared from rat AM and that (2.26 µg of protein/ml) from the LPLA2 transfected cells were assayed in citrate buffer, pH 4.5, with 40 µM NAS in liposomal form with different concentrations of MJ33. The enzyme activity was determined as described in the Example 1. The enzyme activity in the absence of MJ33 was used as the control. A concentration dependent inhibition of the transacylase activity was observed in the presence of this compound. A comparable response was noted for the expressed c-myc-tagged mouse LPLA2.

Pulmonary alveolar proteinosis is a disorder of impaired catabolism of surfactant phospholipids and proteins. The GM-CSF null mouse was discovered to exhibit a phenotype consistent with the human disease. These mice display excess surfactant accumulation in the lungs associated with the engorgement of lipids within alveolar macrophages. LPLA2 activity was measured in the alveolar macrophages of C57BL/6 mice, GM-CSF null mice, and bi-transgenic mice that express GM-CSF under the control of the surfactant protein C promoter. The specific activities of LPLA2 from C57BL/6, GM-CSF (−/−) and SP-C-GM mouse macrophages were 9.50±0.055, 1.58±0.081 and 19.4±1.40 µg/min/mg of protein, respectively. LPLA2 activity, as measured by the time dependent increase in 1-O-acyl-N-acetylsphingosine, was readily apparent in the wild-type mouse macrophages. However, this activity was undetectable in macrophages from the null mice. The GM-CSF transgenic mouse macrophages demonstrated somewhat higher LPLA2 activity. An immunoblot of the proteins as also obtained. The soluble fraction proteins (18.7 µg) were separated by SDS-polyacrylamide gel electrophoresis and subjected to immunoblotting. For the mLPLA2 lane, the soluble fraction was prepared from c-myc-tagged mouse LPLA2 expressed in COS7 cells. The LPLA2 densitometric ratios of the C57BL/6 band to that of the SP-C-GM band was 1:1.96, thereby showing that isolated alveolar macrophages of the respective mice displayed parallel changes to those seen in specific activity. No LPLA2 was detected in the GM-CSF−/− mice.

The acidic lysosomal transacylase is a novel type of phospholipase A2 that is structurally homologous to lecithin cholesterol acyltransferase (LCAT). The chromosomal location of the lysosomal phospholipase A2 gene on 16q22 close to LCAT suggests that the lipase arose as a gene duplication product of LCAT. Because the lysosomal phospholipase A2 lacks the lipoprotein binding domain present on LCAT and demonstrated no activity toward cholesterol as an acceptor, the functional significance of this enzyme was not immediately apparent at the time it was first identified. The markedly increased expression and activity of the phospholipase A2 observed in alveolar macrophages suggests that the primary function of this enzyme is likely to be the degradation of glycerophospholipids present in pulmonary surfactant. Several observations support this view.

First, the enzyme expression, levels, and activity are markedly higher in alveolar macrophages than in monocytes or peritoneal macrophages. Second, the specific activity of the phospholipase A2 is considerably higher than that reported for other candidate enzymes, particularly the Prdx6/aiPLA2. Third, the enzyme is inhibited by MJ33, an inhibitor previously demonstrated to block the majority of dipalmitoyl-phosphatidylcholine degradation in murine lung. Fourth, recent gene targeting studies of Prdx6/aiPLA2 do not report a pulmonary phenotype (Mo et al., FEBS Lett 555, 192-8, 2003; Wang et al., J Biol Chem 278, 25179-90, 2003). Fifth, the lysosomal PLA2 is not detected in alveolar macrophages from GM-CSF−/− mice and expressed with higher activity from transgenic mice that overexpress GM-CSF. Proof positive of the role for this enzyme in surfactant degradation will require the elimination of the gene product by gene targeting studies.

Example 3

CADs Induce Phospholipidosis by Inhibiting LPLA2

The D-threo-1phenyl-2-decanoylamino-3-morphilino-propanol family of agents are a family of amino ceramide-like compounds that have been shown to be useful in the treatment of glycosphingolipidoses (see e.g., U.S. Pat. Nos. 6,569,889; 6,518,259; 6,255,336; 6,098,631; 6,051,598; 6,040,332; 6,030,995; 5,952,370; 5,945,442; 5,916,911 for description of such compounds and methods of making and using the same). It was thought that the LPLA2 of the present invention may also be a target site for the therapeutic activity of these this family of agents. The addition of PDMP to the LPLA2 assay showed that these compounds potently inhibited the transacylase and phospholipase A2 activities of the enzyme in the mid-micromolar range (FIG. 1A-1D). It had previously been reported that the incubation of CHO cells with PDMP induced lysosomal lamellar inclusions consistent with the development of phospholipidosis [Rosenwald and Pagano, J. Lipid. Res., 35:1232-1240, 1994]. PDMP and its related homologs contain a hydrophilic domain with a substituted nitrogen and a hydrophobic aromatic group, functional groups that are typical of CADs in general. The present inventors have now demonstrated that the phospholipidosis caused by PDMP and other CADs is a result of the inhibitory activity of these agents against LPLA2.

Figure 1A:
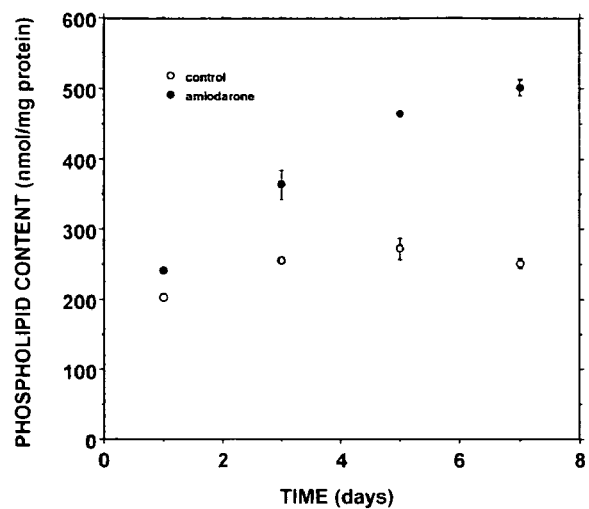
FIG. 1A-1D. Effect of two cationic amphipathic drugs on LPLA2 activity and phospholipids content of MDCK cells. Effect of two cationic amphipathic drugs on LPLA2 activity and phospholipid content in MDCK cells.
Figure 1B:
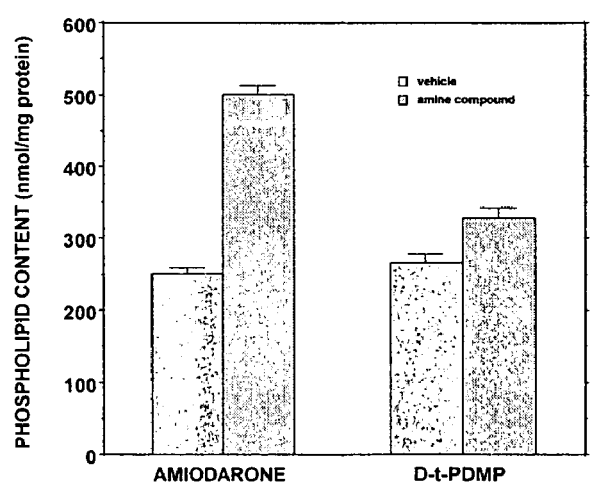
Figure 1C:
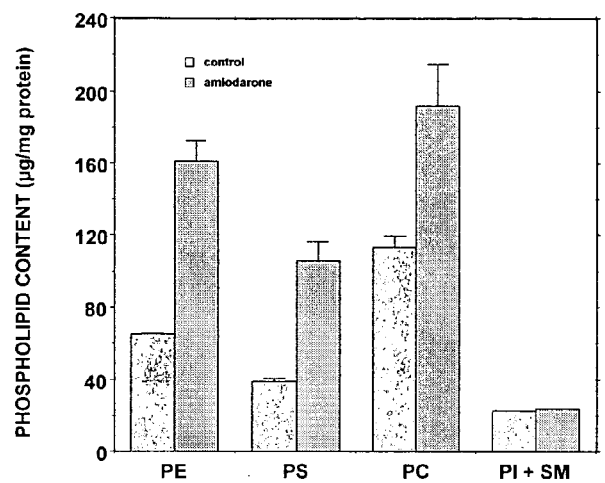
Figure 1D:
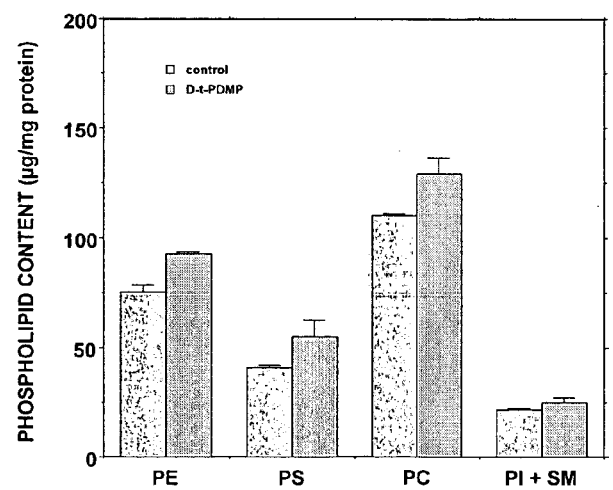

In FIG. 1A, it can be see that amiodarone in the enzyme assay for LPLA2 activity reveals an inhibitory profile that was comparable to but greater than PDMP (FIG. 1A). Fluoxetine also inhibited LPLA2 but with lesser potency, but tetracycline was without effect. Amiodarone demonstrated a greater inhibitory activity against the LPLA2 ($IC_{50}$ of 15 versus 30 µM). To further ascertain whether PDMP was indeed a CAD, MDCK cells were incubated for up to 7 days with the glucosylceramide synthase inhibitor (15 µM). Modest, but significant increases in total phospholipid content were observed (FIG. 1B). Amiodarone, by contrast resulted in comparable but greater increases in phospholipid content consistent with its greater inhibitory activity against LPLA2. The time-dependent changes in the content of specific phospholipid species were evaluated in MDCK cells treated with amiodarone. The content of phosphatidylethanolamine and phosphatidylcholine, major substrates for LPLA2, increased following exposure to both amiodarone and PDMP.

Figure 2:
FIG. 2 shows ultrastructural evaluation of amiodarone on MDCK cells. Cells were grown for 7 days in the absence or presence of the individual CAD at the concentrations indicated. Arrowheads denote phospholipid inclusions.
Figure 2:
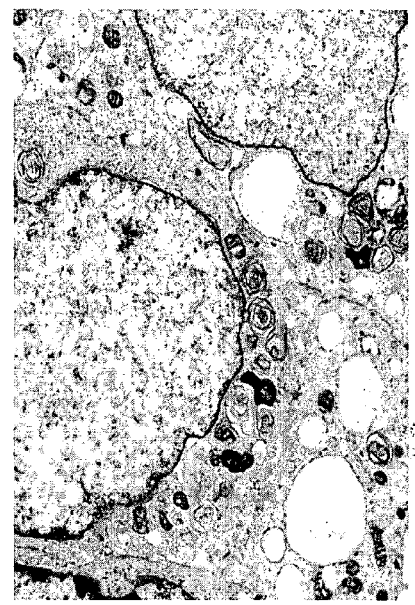

To further confirm that both PDMP and amiodarone were causing lysosomal phospholipid accumulation, electron microscopy was performed on cells treat with either PDMP or amiodarone. Treatment of cells with these CADs at their $IC_{50}$s for transacylase inhibition was associated with obvious lysosomal phospholipid inclusions (FIG. 2). From these data, the inventors concluded that CADs induce phospholipid accumulation in MDCK cells. These drugs also induce lysosomal lamellar body formation. The phospholipid accumulation caused by these drugs occurs in a concentration dependent manner. The half maximal inhibition of LPLA2 activity for amiodarone (15 µM) and PDMP (50 µM) parallels the concentrations over which phospholipid accumulation is observed.

The lungs were particularly susceptible to phospholipidosis by the CADs because as shown in Example 2, the LPLA2 is highly expressed in alveolar macrophages. Briefly reiterating the Example 2 findings, initial determinations of the LPLA2 activity in a variety of rat tissues failed to reveal significant differences in the transacylase and phospholipase A2 activities between organs, including lung. The activity appeared to be present in every tissue assayed. However, when alveolar macrophages were isolated by bronchoalveolar lavage, a greater than 40-fold increase in activity was observed compared to other tissues. This remarkable increased activity was not seen in peritoneal macrophages or peripheral blood monocytes. Real time PCR revealed a pattern of mRNA expression that paralleled the enzyme activity measurements, consistent with the tissue specific transcriptional regulation of LPLA2.

In order to ascertain that the activity measured in the alveolar macrophage was truly LPLA2, a polyclonal antibody was raised to a peptide sequence shared between mouse, rat, and human LPLA2. The polyclonal antibody used in the immunoblotting experiment was used to evaluate the histological localization of LPLA2 in rat lung. Intense and specific staining of alveolar macrophages was observed. Other cell types, including type II epithelial cells, were not stained with the anti-LPLA2 antibody. By immunoblotting, a single band was observed with the predicted molecular weight. Mouse myc-tagged LPLA2 was similarly recognized. A comparison of the densitometric profiles and specific activities of the alveolar and mouse LPLA2 demonstrated comparable ratios. These data showed that the alveolar LPLA2 is the same enzyme or minimally retains the same properties as the expressed mLPLA2. Moreover, the addition of the myc tag has no effect on the measured enzyme activity.

From the above studies the importance of LPLA2 in phospholipidosis was shown. The inventors proceeded to prepare an animal model for the study of this disorder. The model and its preparation are described further in Example 4.

Example 4

A Murine Model for Phospholipidosis

The studies provided in Example 2 showed that LPLA2 is highly expressed in alveolar macrophages and showed that LPLA2 plays a role in pulmonary surfactant phospholipid catabolism. The following Example provides additional data to corroborate those findings. The present Example is directed to a teaching of a murine model of phospholipidosis in which it is demonstrated that a deficiency of lysosomal phospholipase A2 results in phospholipidosis in young mice. Briefly, double conditional gene targeting was employed to further corroborate the biological function of LPLA2. LPLA2 deficient mice (lpla2$^{-/-}$) were generated by the systemic deletion of exon 5 of the lpla2 gene, which encodes the lipase motif essential for the phospholipase A2 activity. The survival of the lpla2$^{-/-}$ mice was normal. lpla2$^{-/-}$ mouse mating pairs yielded normal litter sizes, indicating that the gene deficiency did not grossly impair fertility or fecundity. Alveolar macrophages from wild-type but not lpla2$^{-/-}$ mice readily degraded radiolabeled phosphatidylcholine. A marked accumulation of phospholipid, in particular phosphatidylethanolamine and phosphatidylcholine, was found in the alveolar macrophages, the peritoneal macrophages, and the spleens of 3 month-old lpla2 mice. Electron microscopy of lpla2–/– mouse alveolar and peritoneal macrophages revealed the appearance of foam cells with lamellar inclusion bodies, a hallmark of cellular phospholipidosis. These studies are described in further detail below.

Materials & Methods

Reagents. Phosphatidylethanolamine (PE), 1,2-dioleloyl-sn-glycero-3-phosphorylcholine (DOPC) and 1-palmitoyl-2-oleoyl-sn-3-glycero-phosphorylcholine (POPC) were obtained from Avanti Polar Lipids (Alabaster, Ala.). Dicetyl phosphate was purchased from Sigma (St. Louis, Mo.); 1-palmitoyl-2-[$^{14}$C]-oleoyl-sn-3-glycero-phosphorylcholine (25 µCi/ml) was from Amersham Biosciences (Piscataway, N.J.); N-Acetyl-D-erythro-sphingosine (NAS) was from Matreya (Pleasant Gap, Pa.). Bicinchoninic acid protein assay reagent was obtained from Pierce Chemical (Rockford, Ill.).

Figure 3A:
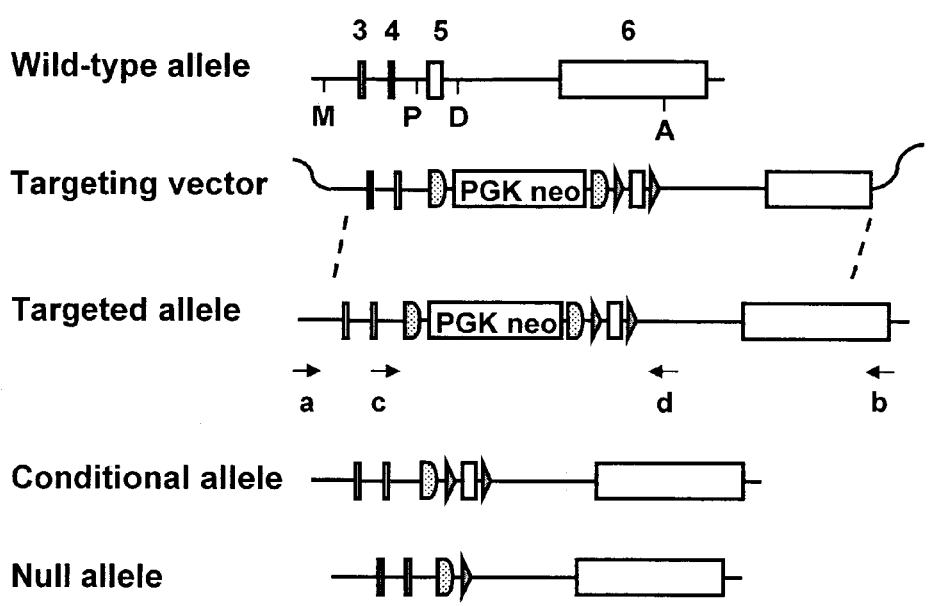
FIG. 3A. Strategy for producing allelic series of mutations at the lpla2 locus. Partial map of the murine lpla2 locus (Top). Horizontal lines and open boxes with numbers represent introns and lpla2 exons, respectively. Vertical lines represent restriction sites, M, SmaI; P, SpeI; D, DraI; A, SacI. The LPLA2 double conditional targeting vector was designed (Top Middle). Shaded triangles represent lox P sites flanking the lpla2 gene exon 5, and shaded half-circles represent FRT sites flanking the neomycin resistance cassette (PGK neo). The targeted allele was generated by homologous recombination (Middle). The primers used for PCR are shown as horizontal arrows with alphabet. The conditional allele was generated by Flp-mediatied excision (Bottom Middle). The heterozygous mice carrying targeted allele were mated with FLP1 transgenic mice to delete neo cassette. The null allele was generated by Cre-mediated excision (Bottom). The heterozygous mice carrying conditional allele were mated with EIIa Cre transgenic mice to delete exon 5.

Generation of lpla2 double conditional targeted mice. The genome sequence containing the lpla2 gene was obtained from screening the Resgen CJ7 ES cell line BAC clone library (Invitrogen, Carlsbad, Calif.). This sequence has been submitted to GenBank under accession number AY179884. A SmaI-SacI fragment of approximately 8,450 bp of the lpla2 gene was subcloned into the pUC vector. In a previous report it was shown that the lipase motif, located within exon 5, is essential for LPLA2 enzyme activity. Therefore, to create the conditional null allele, the SpeI-DraI region containing exon 5 was floxed with two lox P sites, and then inserted into the vector (FIG. 3A). The PGK neo cassette flanked with two FRT sites was inserted at SpeI site in the intron between exon 4 and 5 in reverse orientation. The targeting vector was sequenced to ensure that no mutation had been introduced and then linearized by NdeI digestion and electroporated into CJ7 ES cells. Homologous recombinant clones were obtained from G418-resistant colonies screened at a frequency of 20%. The G418 resistant clones were screened by PCR using primers inside and outside the targeting construct.

Figure 3B:
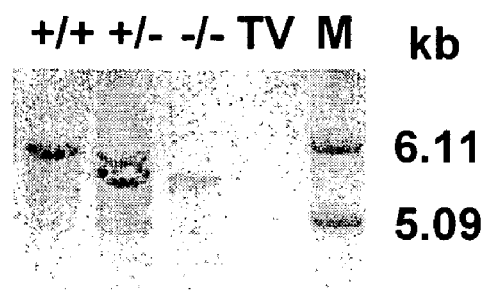
FIG. 3B. Genotype analysis by PCR. Genomic DNA was extracted from mouse tail and performed PCR to evaluate homologous recombination. The primers, a and d, and b and c, were used for upper panel and lower panel assays, respectively. TV indicates targeting vector. M indicates molecular marker.
Figure 3B:
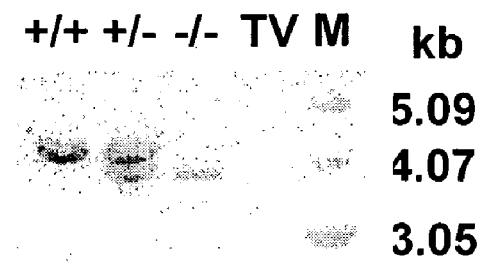

A correctly targeted clone was injected into C57BL/6 blastocysts. The chimeric mice were mated with C57BL/6 to obtain heterozygous mice carrying the targeted allele. Mice carrying the targeted allele were mated with flp1 mice (The Jackson Laboratory, stock #3800) to delete the neo cassette. The conditional heterozygous mice were then mated with EIIa Cre mice of C57BL/6 background (The Jackson Laboratory, stock #3724) to excise the region containing exon 5. The heterozygous mice carrying the null allele were mated to generate homozygous (–/–), heterozygous (+/–), and wild-type (+/+) littermates of the lpla2 null allele. Homologous recombination at null allele was screened by PCR (FIG. 3B). Genomic DNA was extracted from the tails of the mice. The PCR primers were as follows: a, 5'-CAGGGTAGCTCA-CAACTCTTTG-3' (SEQ ID NO:14); b, 5'-CAAAGCTCTG-GACTGTTTTCCTGC-3'(SEQ ID NO:15); c, 5'-GAATTC-CTAGACCCCAGCAAGAAGAATGTG-3'(SEQ ID NO:16); d, 5'-CCCTCCCCAGAGATGGATATTT-3'(SEQ ID NO:17). Primers a and d generated 5.8 kb and 5.5 kb products from wild-type allele and null allele by PCR, respectively. Primers b and c generated 4.1 kb and 3.8 kb products from wild-type allele and null allele by PCR, respectively. The PCR amplification employed 35 cycles with steps at 94° C. for 30 sec, 60° C. for 30 sec, and 72° C. for 3 min, which was extended 20 sec every cycle for the last 25 cycles using ExTaq DNA polymerase (Takara Bio, Shiga, Japan). The PCR products were followed by electrophoresis, purification and sequencing. To confirm wild-type, conditional, and null allele, the PCR with primers c and d using rTaq polymerase (Takara Bio) employed 35 cycles with steps at 94° C. for 30 sec, 60° C. for 30 sec, and 72° C. for 1 min. The product sizes were 1,212, 1,444, and 894 bp for the wild-type, conditional, and null alleles, respectively.

RT-PCR analysis. Total RNA was isolated from each mouse organ using TRIzol reagent (Invitrogen) followed by purification using an RNeasy kit (Qiagen, Valencia, Calif.). The total RNA was used to synthesize cDNA with oligo(dT)$_{12-18}$ primers in the SuperScript First-Strand synthesis system (Invitrogen). Primers used for PCR were as follows: 5'-ATGGATCGCCATCTC-3'(forward; SEQ ID NO:18), and 5'-TCAAGGTTCCAGAAGCACACGTTT-3' (reverse; SEQ ID NO:19). PCR was performed using rtaq polymerase with the same condition as described above. PCR products were purified and sequenced.

Isolation of mouse macrophages and tissues. All mice were housed in specific pathogen-free conditions and used at 2-5 months of age. After anesthesia with $CO_2$ inhalation, the organs were isolated. For isolation of alveolar macrophages, the trachea were cannulated and the lungs were lavaged with phosphate-buffered saline (PBS) containing 0.5 mM EDTA. Peritoneal macrophages were obtained by lavage of the peritoneal spaces with PBS containing 0.5 mM EDTA. After counting, cells were suspended in RPMI 1640 medium containing 1× antibiotic-antimycotic solution (Invitrogen) and plated in culture dishes followed by incubation at 37° C. in humidified atmosphere of 5% $CO_2$ in air. Non-adherent cells were removed by washing with PBS. The University of Michigan Committee on the Use and Care of Animals approved all experiments.

Electron microscopy. Fresh tissue was minced into 1-mm cubes, and alveolar and peritoneal lavage cells were collected, and then fixed by immersion in 4% glutaraldehyde, 0.1 M sodium cacodylate buffer (pH 7.3). The sample was post-fixed with osmium tetroxide before embedding in Epon. Onemicron sections, stained with toluidine blue, were screened by light microscopy to select cross sections for ultrastructural study. Thin sections were stained with uranyl acetate and lead citrate before examination with a Philips 400T transmission electron microscope. Representative photomicrographs were selected.

Preparation of cell homogenate and soluble fraction from mouse alveolar and peritoneal macrophages and tissues. For the preparation of the soluble fractions of alveolar macrophages and peritoneal macrophages, the adherent cells on the culture dishes (35-mm dish) were washed three times with 2 ml of cold PBS, scraped with a small volume of PBS and transferred into 15 ml plastic tubes. The cells were collected by centrifugation at 800 g for 10 min at 4° C., re-suspended with 0.4-1.0 ml of cold 0.25 M sucrose, 10 mM Hepes (pH 7.4), 1 mM EDTA. The cell suspension was disrupted by a probe type sonicator for 10 sec×5 at 0° C. to obtain the cell homogenate. The homogenate was centrifuged for 1 h at 100,000 g at 4° C. The resultant supernatant was passed through a 0.2 μm filter and used as a soluble fraction.

For the preparation of soluble fractions of mouse tissues, each organ was washed with cold PBS, weighed and homogenized by a Potter Elvehjem-type homogenizer with cold 0.25 M sucrose, 10 mM Hepes (pH 7.4), 1 mM EDTA. The homogenate was centrifuged for 10 min at 600 g at 4° C. The resultant supernatant was sonicated with a probe type sonicator for 10 sec×5 at 0° C. and centrifuged for 1 h at 100,000 g at 4° C. The supernatant was passed through a 0.2 μm filter and used as a soluble fraction.

Enzyme phospholipase A2/transacylase assay. Phospholipids, DOPC and PE, and N-acetylsphingosine were used in the assay system as donor and an acceptor, respectively, of an acyl group. The transacylase activity by LPLA2 was determined by analysis of 1-O-acyl-N-acetylsphingosine formation rate. The reaction mixture consisted of 45 mM sodium citrate (pH 4.5), 10 μg/ml BSA, 40 μM N-acetylsphingosine incorporated into phospholipid liposomes (DOPC/PE/dicetyl phosphate/N-acetylsphingosine (5:2:1:2 in molar ratio)) and soluble fraction (0.7-10 μg) in a total volume of 500 μl. The reaction was initiated by adding the soluble fraction, kept for 5-60 min at 37° C. and terminated by adding 3 ml of chloroform/methanol (2:1) plus 0.3 ml of 0.9% (w/v) NaCl. The mixture was centrifuged for 5 min at room temperature. The resultant lower layer was transferred into another glass tube and dried down under a stream of nitrogen gas. The dried lipid dissolved in 40 μl of chloroform/methanol (2:1) was applied on an HPTLC plate and developed in a solvent system consisting of chloroform/acetic acid (9:1). The plate was dried down and soaked in 8% (W/V) $CuSO_4$, $5H_2O$, 6.8% (v/v) $H_3PO_4$, 32% (v/v) methanol. The wet plate was briefly dried down with a hair dryer and charred for 15 min in a 150° C. oven. The plate was scanned and the reaction products were quantified by NIH-image 1.62.

Lipid analysis. Lipids were extracted from tissues, alveolar macrophages, peritoneal macrophages and bronchoalveolar lavage fluid of 3 month-old mice by the partially modified method of Bligh and Dyer (Can J Biochem Physiol, 37, 911, 1959). The phospholipid content was measured by the method of Ames (Methods Enzymol 8: 115-118, 1966). Individual phospholipids were separated by high performance thin-layer chromatography and quantified as described above.

Degradation of 1-palmitoyl-2-[$^{14}$C]-oleoyl-sn-3-glycerophosphorylcholine (POPC) by alveolar macrophages. Alveolar macrophages ($1.3 \times 10^6$ cells) obtained from 3-5 month-old lpla2$^{+/+}$ and lpla2$^{-/-}$ mice were seeded into a 35-mm dish containing 2 ml of RPMI 1640 medium (Invitrogen) containing 1× antibiotic-antimycotic and followed by incubation at 37° C. in a humidified atmosphere of 5% $CO_2$ in air. After 90 min, non-adherent cells were removed by washing with PBS. The adherent cells were incubated with 2.1 ml of RPMI 1640 medium containing 320 μM (0.25 μCi/ml) [$^{14}$C]-labeled POPC in liposomes consisting of POPC/dicetyl phosphate (10:1 in molar ratio) for 4 hours at 37° C. After the incubation, the cells were washed 3 times with 2 ml of cold PBS and fixed with 1 ml of cold methanol. The fixed cells were scraped and transferred into a glass tube. An additional one ml of methanol was used to recover the remaining cells in the dish. The cell suspension was mixed with 1 ml chloroform plus 0.8 ml of 0.9% NaCl and sonicated in a water bath sonicator briefly, and kept for 1 hour at room temperature. The mixture was centrifuged for 30 min at 2,000 g at room temperature and the supernatant was transferred into a long glass tube. The supernatant was mixed and vortexed with 3 ml of chloroform plus 0.8 ml of 0.9%. NaCl, and centrifuged for 5 min at 800 g. The lower layer was washed with 2 ml of methanol plus 1.6 ml of 0.9% NaCl, centrifuged 5 min at 800 g and washed again with 2 ml of methanol plus 1.6 ml of water. The resultant lower layer was transferred into another glass tube and dried down under a stream of nitrogen gas. The dried lipid was dissolved in 100 μl of chloroform/methanol (2:1). Half of the lipid extract was applied to an HPTLC and developed in a solvent system consisting of chloroform/acetic acid (9:1) or chloroform/methanol/water (60:35:8). After development, the plate was dried down, sprayed with ENHANCE and exposed on X-ray film at −80° C. for 4 days.

Results

Using the above exemplary techniques, the inventors generated the following results which show the generation of LPLA2 deficient mice which serve as a model for phospholipidosis. The result are now described in further detail.

Generation of LPLA2 deficient mice. To create LPLA2 null mice, a targeting vector was designed and constructed containing two loxP sites and two FRT sites with a PGK-neo cassette placed between the FRT sites for modification by use of Cre/loxP and Flp/FRT recombination systems (FIG. 3A). Exon 5, which encodes for the lipase motif essential for LPLA2 activity, was floxed with two loxP sites, and then inserted into the vector. CJ7 ES cells were electroporated with the linearized targeting vector. Homologous recombinant clones were obtained from G418-resistant colonies screened at a frequency of 20%. A correctly targeted clone was injected into C57BL/6 blastocysts. The chimeric mice were mated with C57BL/6 to obtain heterozygous mice carrying the targeted allele.

Figure 3C:
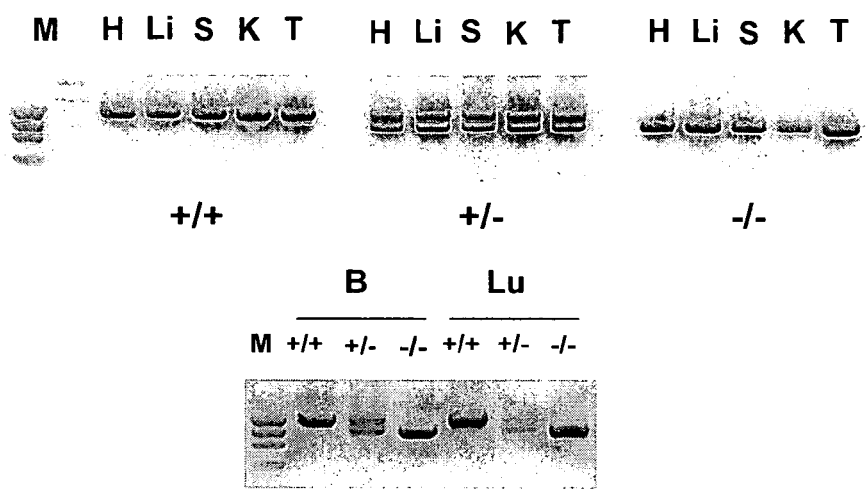
FIG. 3C. RT-PCR assay. Total RNAs were isolated from various mouse organs and synthesized cDNA. PCR was performed using primers, which are able to cover LPLA2 coding region. M, Molecular marker φX174 RF DNA/HaeIII; H, heart; Li, liver; S, spleen; K, kidney; T, thymus; B, brain; Lu, lung.
Figure 3D:
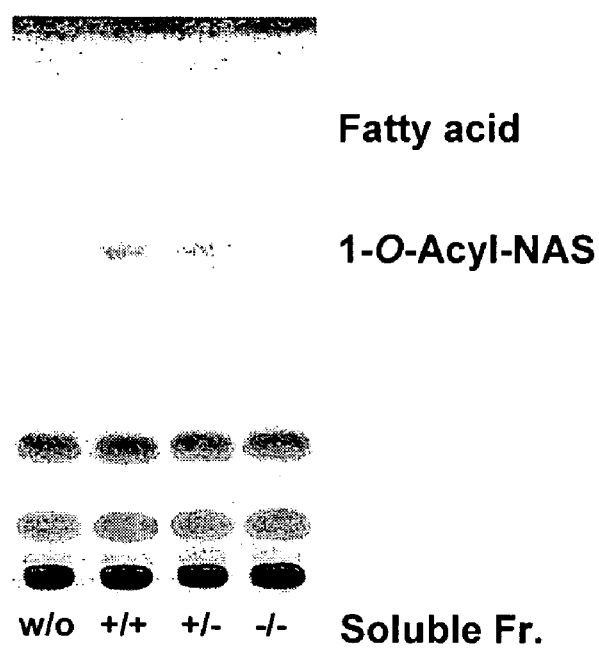
FIG. 3D. Transacylase activity in the soluble fraction of AM obtained from lpla2$^{+/+}$, lpla2$^{+/-}$ and lpla2$^{-/-}$ mice. Each soluble fraction (3 µg of protein) obtained from 3 month-old lpla2$^{+/+}$, lpla2$^{+/-}$ and lpla2$^{-/-}$ mouse AM was incubated for 30 min at 37° C. in citrate buffer, pH 4.5, with 40 µM NAS in liposomal form and formation of 1-O-acyl-NAS was determined as described in Example 4.

Mice carrying the targeted allele were found to be normal and fertile. However, homozygous offspring from heterozygous pairs showed a modest reduction of LPLA2 activity in the soluble fraction of brain. This finding suggested that the neo cassette inclusion affected LPLA2 expression. Flp1 transgenic mice express FLP recombinase in the early embryo under the control of the human β-actin promoter. Mice with the targeted allele were mated with Flp1 transgenic mice to delete the neo cassette. The allele in which the neo cassette was deleted by using Flp/FRT recombination system is termed the "conditional allele". Mice carrying the conditional allele were normal in appearance and fertile. The LPLA2 enzyme activity in the homozygous mice carrying the conditional allele was found to be the same as wild-type mice. EIIa Cre transgenic mice express Cre recombinase in the one-cell zygote stage of embryo under the control of the adenovirus EIIa promoter. Heterozygous mice carrying the conditional allele were mated with EIIa Cre transgenic mice to excise the region containing exon 5. The resultant heterozygous mice carrying the null allele were mated together to generate lpla2$^{-/-}$, lpla2$^{+/-}$, and lpla2$^{+/+}$ littermates. Homologous recombination at the null allele was screened by PCR (FIG. 3B). The predicted product from the deletion of the loxP site flanking region was detected in both lpla2$^{-/-}$, lpla2$^{+/-}$, but not in the lpla2$^{+/+}$ mice.

lpla2$^{+/-}$ mice were viable and fertile. They produced approximately 8.7 pups per litter with a normal Mendelian frequency, indicating no selective fetal or neonatal loss of homozygous pups. Survival of the lpla2$^{-/-}$ mice was normal. lpla2$^{-/-}$ mating pairs gave normal litter sizes (8.5 pups per litter), indicating that the gene deficiency did not grossly impair fertility or fecundity. Screening of lpla2 mRNA expression in seven organs from lpla2$^{-/-}$ mice demonstrated the deletion of exon 5 in each organ (FIG. 3C), indicating that the deletion was systemic. The LPLA2 enzyme activity was compared among each genotype. The transacylase activity as measured by the formation of 1-O-acyl-N-acetylsphingosine, was absent in lpla2$^{-/-}$ mouse alveolar macrophages. The transacylase activity from lpla2$^{+/-}$ mouse alveolar macrophages was approximately 50% of that of the lpla2$^{+/+}$ mouse alveolar macrophages. The deficiency of the enzyme activity in the soluble fraction of the lpla2$^{-/-}$ mouse was also observed in other cells and tissues, including peritoneal macrophages, heart, lung, liver, spleen, kidney, thymus and brain.

There was no significant difference in body and organ weights between the lpla2 genotypes at 4 months of age. A routine histological survey of their organs, including the hearts, livers, kidneys, brains and spleen, by hematoxylin and eosin staining showed no difference between wild type and homozygous mice.

Phospholipid degradation in alveolar macrophages. Many classes of phospholipase A2 exist. Thus, on the one hand, the absence of ceramide transacylase activity in alveolar macrophages did not necessarily mean that cellular phospholipase A2 activity would be impaired as well. On the other hand, lpla2 is very highly expressed in alveolar macrophages and might represent the major phospholipase A2 activity. Therefore, the degradation of phosphatidylcholine was more extensively evaluated in the mouse alveolar macrophages. A choice of substrate was required. When previously studied, lpla2 was observed to recognize 1,2-dipalmitoyl-sn-3-glycero-phosphorylcholine (DPPC), a major component of pulmonary surfactant lipid, when presented as a substrate in DOPC/DPPC liposomes. However, lpla2 preferred DOPC to DPPC. Furthermore, DPPC led to a reduction of the enzyme activity on DOPC in DOPC/DPPC liposomes. These results suggested that unsaturated phospholipids are better substrates than saturated phospholipids and may provide a preferable environment in the LPLA2 reaction.

The transfer of oleic acid to N-acetyl-sphingosine and the release of oleic acid from POPC by the soluble fraction obtained from lpla2$^{+/+}$ mouse alveolar macrophages were observed when POPC/dicetyl phosphate/N-acetyl-sphingosine liposomes were used (FIG. 4A). The transacylase activity in the POPC liposomes system was comparable to that observed with the DOPC/dicetyl phosphate/N-acetyl-sphingosine liposome system, encouraging the further use of alveolar macrophages and radiolabeled POPC.

The radioactive oleic acid released from POPC was readily detected in the lipid extract obtained from the lpla2$^{+/+}$ mouse alveolar macrophages treated with 1-palmitoyl-2-[$^{14}$C]-oleoyl-sn-3-glycero-phosphorylcholine/dicethyl phosphate liposomes (FIG. 4B). On the contrary, there virtually no radioactive oleic acid detected in the lipid extract obtained from the lpla2$^{-/-}$ mouse alveolar macrophages treated with [$^{14}$C]-labeled POPC liposomes (FIG. 4B). The total radioactivity found in the lipid extract obtained from the lpla2$^{-/-}$ mouse alveolar macrophages was about half the amount of that from the lpla2$^{+/+}$ mouse macrophages. The radioactivity of oleic acid recovered from the TLC plate was 260 cpm and 50 cpm for lpla2$^{+/+}$ and lpla2$^{-/-}$ mouse macrophages respectively (FIG. 4B). Additionally, the released radioactive oleic acid was comparably low (40 cpm on the TLC plate) when the [$^{14}$C]-labeled POPC liposomes were incubated with the cultured medium without alveolar macrophages. Thus the radioactive oleic acid released from the lpla2$^{-/-}$ mouse alveolar macrophages was at least 10 times lower than that released from the lpla2$^{+/+}$ mouse macrophages. Therefore, most of oleic acid released from POPC in the lpla2$^{+/+}$ mouse alveolar macrophages was a result of LPLA2 activity.

Interestingly, the radioactive lyso-PC was detected in both lpla2$^{+/+}$ and lpla2$^{-/-}$ alveolar macrophages. This metabolite, labeled in the sn-2 position, is produced by phospholipase A1. The radioactivity of lyso-PC was 150 cpm and 100 cpm respectively for lpla2$^{+/+}$ and lpla2$^{-/-}$ mouse alveolar macrophages. These results indicate that the degradation of phospholipid in lpla2$^{-/-}$ mouse alveolar macrophages is greatly impaired due to a lack of phospholipase A2 activity.

Phospholipid accumulation in the lpla2$^{-/-}$ mouse. The phospholipid content and profile in alveolar and peritoneal macrophages and other tissues of 3 month-old lpla2$^{+/+}$ and lpla2$^{-/-}$ mice were next examined. The total phospholipid content of the lpla2$^{-/-}$ mouse alveolar macrophages (593 nmol of phospholipid/mg of protein) was more than two times higher than that of the lpla2$^{+/+}$ mouse alveolar macrophages (256 nmol of phospholipid/mg of protein). Thin layer chromatography of the lipid extract of the alveolar macrophages showed a marked accumulation of both PE and PC in the lpl2$^{-/-}$ mouse (FIG. 5A, left panel). PE and PC levels were 4 times and 2 times higher, respectively, in the lpla2$^{-/-}$ versus lpla2$^{+/+}$ mouse cells. Phosphatidylserine, phosphatidylinositol, and sphingomyelin levels were no different consistent with the known specificity of lpla2 for PC and PE. The total phospholipid content in the lpla2$^{-/-}$ peritoneal macrophages (305 nmol of phospholipid/mg of protein) was 40% higher than that of the lpla2$^{+/+}$ peritoneal macroophages (223 mmol of phospholipid/mg of protein). A similar change in phospholipid profile was observed in the lpla2$^{-/-}$ peritoneal macrophages (FIG. 5A, right panel).

The total phospholipid content of the spleens of the lpla2$^{+/+}$, lpla2$^{+/-}$ and lpla2$^{-/-}$ mice were 109±2.49, 112±4.60 and 143±8.09 nmol of phospholipid/mg of protein, respectively. FIG. 5B shows the phospholipid profile of the spleen of the LPLA2$^{+/+}$, LPLA2$^{+/-}$ and LPLA2$^{-/-}$ mice. PE and PC levels in the lpla2$^{-/-}$ mouse spleens were 100% and 30%, respectively, higher than those of the lpla2$^{+/+}$ mouse spleens (FIG. 5B). Also, a similar increase for PE and PC levels, but smaller difference, was observed in whole liver and lung. The distribution pattern of LPLA2 activity in tissues and macrophages in mouse was mostly the same as that in rat, suggesting that there is an inverse relationship between PC and PE accumulation and lpla2 activity in lpla2$^{-/-}$ and lpla2$^{+/+}$ mice. These findings indicate that the deficiency of lpla2 induces PE and PC accumulation in mice. Thus the absence of lpla2 may cause systemic phospholipidosis in mice.

Figures 6A, 6B, 6C, 6D:
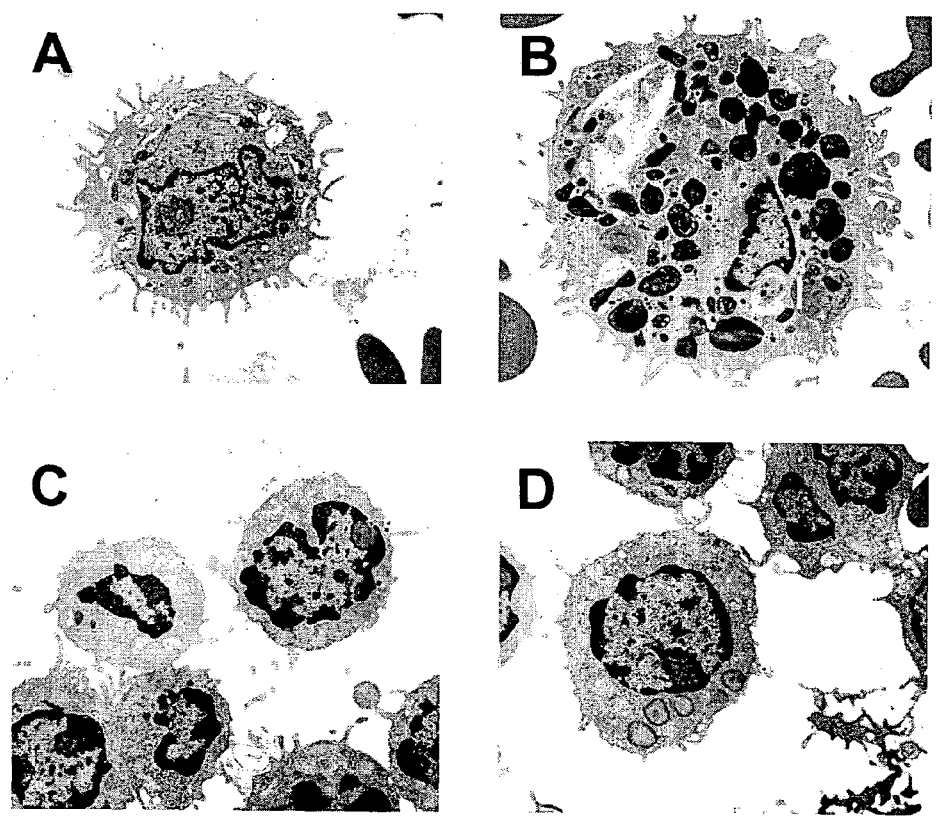

Ultrastructural analysis of alveolar and peritoneal macrophages. Electron microscopy was performed on AM and PM obtained from 3 month-old lpla2$^{-/-}$ and lpla2$^{+/+}$ mice to confirm the presence of phospholipidosis. The alveolar macrophages from the lpla2$^{-/-}$ alveolar macrophages were markedly larger compared to those from the lpla2$^{+/+}$ mice. Numerous lamellar inclusion bodies, indicative of cellular phospholipidosis, were observed in the lpla2$^{-/-}$ mouse alveolar macrophages (FIG. 6B). However, such lamellar inclusion bodies were only rarely present in the lpla2$^{+/+}$ cells (FIG. 6A). A similar, but less robust change was also observed in the peritoneal macrophages (FIGS. 6C and 6D). The increase in phospholipid accumulation corresponds to the presence of lamellar inclusions and cellular phospholipidosis.

The data presented above show that lpla2$^{-/-}$ mice generated by the systemic deletion of the lpla2 gene exon 5, which encodes the lipase motif essential for LPLA2 activity, were healthy at birth and fertile. The mice were used to provide evidence that the block of the degradation pathway of phospholipid by the deficiency of LPLA2 induces selective accumulation of phospholipid and leads to phospholipidosis. LPLA2 deficient mice showed that LPLA2 play an important role in cellular phospholipid homeostasis. The availability of LPLA2$^{-/-}$ mice provides an efficient and effective model for investigating further biological functions of LPLA2 and also for testing agents that affect the activity of this enzyme as well as agents that may be used to ameliorate phospholipidosis as well as to screen for agents that cause or exacerbate phospholipidosis.

Thus, the present invention is directed to methods and compositions for improving pulmonary surfactant catabolism by using a lysosomal phospholipase A2 in methods for the diagnosis, and treatment of disorders of phospholipid catabolism such as pulmonary alveolar proteinosis. The following paragraphs defines certain preferred aspects of the present invention:

Paragraph 1. A method of increasing degradation of glycerophospholipids in pulmonary surfactant comprising contacting a sample containing pulmonary surfactant with a composition comprising a lysosomal phospholipase A2 (LPLA2) protein having an amino acid sequence of SEQ ID NO:2, or a biologically active fragment or variant of a protein having an amino acid sequence of SEQ ID NO:2.

Paragraph 2. The method of paragraph 1, wherein said pulmonary surfactant is a component of an alveolar macrophage.

Paragraph 3. The method of paragraph 2, wherein said alveolar macrophage is located in vitro.

Paragraph 4. The method of paragraph 3, wherein said alveolar macrophage is located in vivo.

Paragraph 5. The method of paragraph 4, wherein said pulmonary surfactant has accumulated as a result of cationic amphiphilic drug (CAD) administration.

Paragraph 6. The method of paragraph 4, wherein said contacting comprises administering a composition comprising said lysosomal phospholipase A2 protein in combination with a pharmaceutically acceptable carrier.

Paragraph 7. The method of paragraph 6, wherein said composition is formulated as an inhalant.

Paragraph 8. A method of increasing the in vivo breakdown of pulmonary surfactant in a mammal comprising administering to said mammal a composition comprising a LPLA2 protein having an amino acid sequence of SEQ ID NO:2, or a biologically active fragment or variant of a protein derived from the amino acid sequence of SEQ ID NO:2.

Paragraph 9. The method of paragraph 8, wherein said breakdown of pulmonary surfactant comprises increasing the degradation of the phospholipid component of said pulmonary surfactant.

Paragraph 10. The method of paragraph 8, wherein said phospholipid component is selected from the group consisting of phosphatidylcholine (PC), phosphatidylethanolamine (PE), phosphatidylserine (PS), phosphatidylinositol (PI), phosphatidylglycerol (PG), cardiolipin (CL), a sphingolipid, sphingomyelin (SM), and phosphatidic acid (PA).

Paragraph 11. The method of paragraph 8, wherein said phospholipid component is dipalmitoyl PC.

Paragraph 12. The method of paragraph 10, wherein said phospholipid component is PE.

Paragraph 13. The method of paragraph 8, wherein said mammal has been or will be undergoing therapy with a CAD.

Paragraph 14. The method of paragraph 8, wherein said LPLA2 composition is administered locally.

Paragraph 15. The method of paragraph 14, wherein said locally administered LPLA2 composition is administered in the form of an inhalant.

Paragraph 16. The method of paragraph 8, wherein said mammal is suffering from pulmonary alveolar proteinosis and said administration of said LPLA2 alleviates one or more of the symptoms of pulmonary alveolar proteinosis.

Paragraph 17. A method of treating pulmonary alveolar proteinosis, and conditions associated therewith, in a mammal comprising increasing LPLA2 activity in the alveolar macrophages of said mammal.

Paragraph 18. The method of paragraph 17, wherein said increasing LPLA2 activity comprises administering to said mammal a first composition comprising LPLA2 in a pharmaceutically acceptable carrier in an amount effective to increase phospholipid catabolism in the alveolar macrophages of said mammal.

Paragraph 19. The method of paragraph 18, wherein said first composition comprising said LPLA2 comprises a LPLA2 protein composition.

Paragraph 20. The method of paragraph 17, said increasing LPLA2 activity comprises administering to said mammal a composition comprising a stimulator of LPLA2 activity of a protein of SEQ ID NO:2.

Paragraph 21. The method of paragraph 17, wherein increasing the activity of LPLA2 comprises increasing the expression of LPLA2 in the alveolar macrophages of said mammal.

Paragraph 22. The method of paragraph 21, wherein said increasing expression of LPLA2 in the alveolar macrophages of said mammal comprises contacting said macrophages with an expression construct comprising an isolated polynucleotide encoding a LPLA2 operably linked to a promoter that promotes the expression of said LPLA2 in said alveolar macrophages.

Paragraph 23. The method of paragraph 22, wherein said isolated polynucleotide encoding said LPLA2 comprises a polynucleotide encoding a protein of SEQ ID NO: 2 or a polynucleotide encoding an active fragment of a protein of SEQ ID NO:2.

Paragraph 24. The method of paragraph 17, wherein said mammal manifests a symptom of pulmonary alveolar proteinosis selected from the group consisting of respiratory insufficiency, dry cough, polycysthemia, hypergammaglobulinemia, hypoxemia, and chest X-ray showing butterfly pattern opacity and said treating alleviates one or more of said symptoms.

Paragraph 25. The method of paragraph 17, further comprising administering a second composition comprising a potassium iodide, a proteolytic enzyme, a corticosteroid, a cytokine.

Paragraph 26. A method of inhibiting the accumulation of phospholipid in animal tissue comprising contacting said tissue with a composition comprising LPLA2 in an amount effective to increase the catabolism of phospholipids in said tissue.

Paragraph 27. The method of paragraph 26, wherein said tissue is located in vivo and the accumulation of phospholipid in said tissue has been induced by the administration of a CAD.

Paragraph 28. The method of paragraph 27, wherein said tissue is lung tissue.

Paragraph 29. The method of paragraph 28, wherein said lung tissue is an alveolar macrophage.

Paragraph 30. The method of paragraph 27, wherein said CAD is selected from the group consisting of chloroquine, amiodarone, fluoxetine, imipramine, gentamicin, azithromycin, tamoxifen and perhexiline.

Paragraph 31. A method of inhibiting the accumulation of phospholipid in alveolar macrophage tissue comprising contacting said alveolar macrophage tissue with a composition comprising LPLA2 in an amount effective to increase the catabolism of pulmonary surfactant.

Paragraph 32. The method of paragraph 31, wherein said accumulation of phospholipid in said alveolar macrophage tissue was induced by the administration of a CAD.

Paragraph 33. A method of diagnosing pulmonary alveolar proteinosis in a test mammal suspected of having said disorder comprising
comparing LPLA2 activity and/or expression in said test mammal to the LPLA2 activity and/or expression of a reference mammal known not have such a disorder, wherein a decreased LPLA2 activity and/or expression in said test mammal compared to said reference mammal indicates pulmonary alveolar proteinosis in said test mammal.

Paragraph 34. A method of diagnosing pulmonary alveolar proteinosis in a test mammal suspected of having said disorder comprising
a. determining the presence of LPLA2 activity and/or expression in the alveolar macrophages of said test mammal;
b. comparing said LPLA2 activity and/or expression to the LPLA2 activity and/or expression of a reference mammal that does not have such a disorder and
c. diagnosing pulmonary alveolar proteinosis in said test mammal if said test mammal has a decreased LPLA2 activity and/or expression as compared to said reference mammal.

Paragraph 35. A method of screening for a modulator of alveolar phospholipid catabolism comprising:
comparing activity of LPLA2 in the presence and absence of a candidate substance, wherein an alteration in the activity of said LPLA2 activity in the presence of the candidate substance indicates that the substance is a modulator of alveolar phospholipid catabolism.

Paragraph 36. A method of screening for a modulator of alveolar phospholipid catabolism comprising:
a) contacting a LPLA2 of SEQ ID NO:2 with a candidate modulator;
ii) monitoring the activity of said LPLA2; and
iii) comparing the activity of LPLA2 in the presence and absence of said candidate substance;
wherein an alteration in the activity of said LPLA2 activity indicates that the substance is a modulator of alveolar phospholipid catabolism.

Paragraph 37. The method of paragraph 35 or 36, wherein said modulator is a stimulator of said phospholipid catabolism and an activator of said LPLA2 activity.

Paragraph 38. The method of paragraph 35 or 36, wherein said candidate substance is selected from the group consisting of a small molecule from a small molecule library, an antibody, and a proteolytic enzyme.

Paragraph 39. The method of paragraph 35 or 36, wherein said modulator is a modulator of phospholipidosis.

Paragraph 40. A method of treating alveolar proteinosis and conditions associated therewith in a human patient, the method comprising introducing into the lung tissue of said patient an effective amount of functionally active LPLA2 thereby increasing the LPLA2 activity of said alveolar macrophages and producing an increase in catabolism of the phospholipid components of the pulmonary surfactant of said patient.

Paragraph 41. A method of treating alveolar proteinosis in a human patient, the method comprising the steps of:
(a) introducing into lung tissue of said patient an effective amount of a polynucleotide that encodes a functionally active LPLA2; and
(b) expressing said LPLA2 in the alveolar macrophages of said patient thereby increasing the LPLA2 activity of said alveolar macrophages and producing an increase in catabolism of the phospholipid components of the pulmonary surfactant of said patient.

Paragraph 42. A composition comprising a LPLA2 protein for use in the treatment of a disorder caused by decreased phospholipid catabolism.

Paragraph 43. The composition of paragraph 42, for use in the treatment of pulmonary alveolar proteinosis and conditions associated therewith.

Paragraph 44. A composition comprising an expression construct that encodes a biologically active LPLA2 protein operably linked to a promoter functional in alveolar macrophages for use in the treatment of a disorder caused by decreased phospholipid catabolism.

Paragraph 45. The composition of paragraph 44, for use in the treatment of pulmonary alveolar proteinosis and conditions associated therewith.

Paragraph 46. A transgenic mouse comprising a disrupted lpla2 gene, wherein said transgenic mouse is homozygous for said disrupted lpla2 gene, and wherein said transgenic mouse exhibits a phospholipidosis phenotype as compared to non-transgenic animals of the same lineage.

Paragraph 47. The transgenic mouse of paragraph 46, wherein said mouse lacks lysosomal phospholipase A2 activity.

Paragraph 48. The transgenic mouse of paragraph 46, wherein said mouse has an increased accumulation of one or more phospholipids in its cells as compared to non-transgenic animals of the same lineage.

Paragraph 49. The transgenic mouse of paragraph 46 wherein said mouse has an increased accumulation of PC and/or PE in its cells as compared to non-transgenic animals of the same lineage.

Paragraph 50. The transgenic mouse of paragraph 48 wherein said increased accumulation of phospholipids is observed in one or more of the cells selected from the group consisting of alveolar macrophages, peritoneal macrophages, and spleen.

Paragraph 51. The transgenic mouse of paragraph 48 wherein said mouse is characterized by the presence of increased lamellar inclusions in the cells of said mouse as compared to cells in a non-transgenic animals of the same lineage.

Paragraph 52. A method of making a transgenic mouse having a disrupted lpla2 gene, comprising:
(a) providing a murine embryonic stem cell comprising an intact lpla2 gene that contains exon 5 of lpa2 gene sequence;
(b) providing a targeting vector capable of disrupting said lpla2 gene upon homologous recombination;
(c) introducing said targeting vector into said murine embryonic stem cell under conditions where said targeting vector will undergo homologous recombination with the lpla2 gene of said murine embryonic stem cell to produce a disrupted gene;

(d) introducing said murine embryonic stem cell into a blastocyst;

(e) implanting said blastocyst into a pseudopregnant female mouse; and (f) delivering a first transgenic mouse comprising a disrupted lpla2 gene from said pseudopregnant female (g) repeating steps (a) through (f) to obtain a second transgenic mouse comprising a disrupted lpla2 gene; and (h) breeding said first transgenic mouse comprising a disrupted lpla2 gene to said second transgenic mouse comprising a disrupted lpla2 gene to obtain one or more mice homozygous for a disrupted lpla2 gene.

Paragraph 53. A murine cell line comprising a disrupted lpla2 gene, wherein substantially all cells of said cell line have both copies of said lpla2 gene disrupted.

All of the compositions and/or methods disclosed and claimed herein can be made and executed without undue experimentation in light of the present disclosure. While the compositions and methods of this invention have been described in terms of specific embodiments, it will be apparent to those of skill in the art that variations of the compositions and/or methods and in the steps or in the sequence of steps of the method described herein can be made without departing from the concept, spirit and scope of the invention. More specifically, it will be apparent that certain agents which are both chemically and physiologically related may be substituted for the agents described herein while the same or similar results are achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. A method of increasing degradation of glycerophospholipids in pulmonary surfactant comprising contacting a sample containing pulmonary surfactant with a composition comprising a lysosomal phospholipase A2 (LPLA2) protein having the amino acid sequence of SEQ ID NO:2, or an enzymatically active fragment of the protein having the amino acid sequence of SEQ ID NO:2.

2. The method of claim 1, wherein said pulmonary surfactant is a component of an alveolar macrophage.

3. The method of claim 1, wherein said pulmonary surfactant has accumulated as a result of cationic amphiphilic drug (CAD) administration.

* * * * *

SEQUENCE LISTING

```
<160> NUMBER OF SEQ ID NOS: 19

<210> SEQ ID NO 1
<211> LENGTH: 1224
<212> TYPE: DNA
<213> ORGANISM: Bos taurus

<400> SEQUENCE: 1
atgggttgcc tctgcctcta ccgctccacc ctgctcacgg gtggcctctt gttcctcctg      60
atgctcgcag atccggcgtt cccggctgga agtcggccac cggtggtgct ggtgcccggt     120
gacatgggca accagctgga ggcaaagctg acaagccgt ccgtcgtgca ctacgtctgc      180
tccaagagga cggatcacta cttcacactg tggctgaacc tggagctgct gctgcccgtc     240
atcattgact gttggatcga caatgtccgg ctgatctaca atcaaacgtc ccacaccacc     300
cagtttcccg aaggtgtgga tgtgcgtgtc cctggctttg gggacacctt ctcaatggag     360
ttcctggacc ccagcaaaag cagcgtgggt tcctatttac ataccatggt ggaaagcctt     420
gtgagctggg gctacgaacg aggcaaggat gtccgggggg cccctacga ctggcgccga      480 gctccaaatg aaaacgggcc ctacttcctg gccctccgca agatgattga ggagatgtac     540
cagctgtacg ggggccctgt ggtgctggtg gcccacagta tgggcaacat gtacatgctc     600
tactttctgc agcatcagcc acaggactgg aaggacaagt acatccgtgc tttcgtagca     660
ctgggtccgc cctgggggg cgtgcccaag accctgcgtg tcctggcctc aggagacaac     720
aaccggatcc cggtcatcag gtccctgaag atccgggcac agcagcggtc tgccgtctcc     780
accacttggc tgctgcccta cagctatacc tggtcaccgc agaaagtctt cgtgcgcaca     840
cctaaggcca actacacgct gcaggactac cgccagttct tccaggacat cggcttcaaa     900
gacggctggt ccatgcggca ggacacggag gggctggttg aggccacagt gccgcctggc     960
gtgcgactgc actgcctcta tggcacgggg gtccccacgc cagagtcctt tgactacgag    1020
agcttcccag accgtgaccc aaaaatccac tatggcaccg gtgatggcac tgtgaacttg    1080
cagagtgccc tgcactgcca tacctggcgt ggcctccaga agcaagaagt gtcattgcag    1140
gcgcttccag gcaatgagca catcgctatg ctggccaaca ccactaccct ggcctacctg    1200
aaacgtgtgc ttcttggacc ctga                                          1224
```

<210> SEQ ID NO 2
<211> LENGTH: 407
<212> TYPE: PRT
<213> ORGANISM: Bos taurus

<400> SEQUENCE: 2

Met Gly Cys Leu Cys Leu Tyr Arg Ser Thr Leu Leu Thr Gly Gly Leu
1               5                   10                  15

Leu Phe Leu Leu Met Leu Ala Asp Pro Ala Phe Pro Ala Gly Ser Arg
            20                  25                  30

Pro Pro Val Val Leu Val Pro Gly Asp Met Gly Asn Gln Leu Glu Ala
        35                  40                  45

Lys Leu Asp Lys Pro Ser Val Val His Tyr Val Cys Ser Lys Arg Thr
    50                  55                  60

Asp His Tyr Phe Thr Leu Trp Leu Asn Leu Glu Leu Leu Pro Val
65                  70                  75                  80

Ile Ile Asp Cys Trp Ile Asp Asn Val Arg Leu Ile Tyr Asn Gln Thr
                85                  90                  95

Ser His Thr Thr Gln Phe Pro Glu Gly Val Asp Val Arg Val Pro Gly
            100                 105                 110

Phe Gly Asp Thr Phe Ser Met Glu Phe Leu Asp Pro Ser Lys Ser Ser
        115                 120                 125

Val Gly Ser Tyr Leu His Thr Met Val Glu Ser Leu Val Ser Trp Gly
    130                 135                 140

Tyr Glu Arg Gly Lys Asp Val Arg Gly Ala Pro Tyr Asp Trp Arg Arg
145                 150                 155                 160

Ala Pro Asn Glu Asn Gly Pro Tyr Phe Leu Ala Leu Arg Lys Met Ile
                165                 170                 175

Glu Glu Met Tyr Gln Leu Tyr Gly Gly Pro Val Val Leu Val Ala His
            180                 185                 190

Ser Met Gly Asn Met Tyr Met Leu Tyr Phe Leu Gln His Gln Pro Gln
        195                 200                 205

Asp Trp Lys Asp Lys Tyr Ile Arg Ala Phe Val Ala Leu Gly Pro Pro
    210                 215                 220

Trp Gly Gly Val Pro Lys Thr Leu Arg Val Leu Ala Ser Gly Asp Asn
225                 230                 235                 240

Asn Arg Ile Pro Val Ile Arg Ser Leu Lys Ile Arg Ala Gln Gln Arg
                245                 250                 255

Ser Ala Val Ser Thr Thr Trp Leu Leu Pro Tyr Ser Tyr Thr Trp Ser
            260                 265                 270

Pro Gln Lys Val Phe Val Arg Thr Pro Lys Ala Asn Tyr Thr Leu Gln
        275                 280                 285

Asp Tyr Arg Gln Phe Phe Gln Asp Ile Gly Phe Lys Asp Gly Trp Ser
    290                 295                 300

Met Arg Gln Asp Thr Glu Gly Leu Val Glu Ala Thr Val Pro Pro Gly
305                 310                 315                 320

Val Arg Leu His Cys Leu Tyr Gly Thr Gly Val Pro Thr Pro Glu Ser
                325                 330                 335

Phe Asp Tyr Glu Ser Phe Pro Asp Arg Asp Pro Lys Ile His Tyr Gly
            340                 345                 350

Thr Gly Asp Gly Thr Val Asn Leu Gln Ser Ala Leu His Cys His Thr
        355                 360                 365

Trp Arg Gly Leu Gln Lys Gln Glu Val Ser Leu Gln Ala Leu Pro Gly

```
                   370                 375                 380
Asn Glu His Ile Ala Met Leu Ala Asn Thr Thr Thr Leu Ala Tyr Leu
385                 390                 395                 400

Lys Arg Val Leu Leu Gly Pro
            405
```

<210> SEQ ID NO 3
<211> LENGTH: 23
<212> TYPE: DNA
<213> ORGANISM: Artificial sequence
<220> FEATURE:
<223> OTHER INFORMATION: Synthetic primer

<400> SEQUENCE: 3
acatgctcta ctttctgcag cgg                                         23

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
agaagcacac gtttcagata                                             20

<210> SEQ ID NO 5
<211> LENGTH: 21
<212> TYPE: DNA
<213> ORGANISM: Artificial sequence
<220> FEATURE:
<223> OTHER INFORMATION: Synthetic primer

<400> SEQUENCE: 5
cagtgtgcac cacagaactt g                                           21

<210> SEQ ID NO 6
<211> LENGTH: 21
<212> TYPE: DNA
<213> ORGANISM: Artificial sequence
<220> FEATURE:
<223> OTHER INFORMATION: Synthetic primer

<400> SEQUENCE: 6
agctctttgg tgaagactcc t                                           21

<210> SEQ ID NO 7
<211> LENGTH: 21
<212> TYPE: DNA
<213> ORGANISM: Artificial sequence
<220> FEATURE:
<223> OTHER INFORMATION: Synthetic primer

<400> SEQUENCE: 7
actacatctg gcctgccgca a                                           21

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
agaagcattc gggccatctc                                             20

<210> SEQ ID NO 9
<211> LENGTH: 10
<212> TYPE: PRT
<213> ORGANISM: Artificial sequence
<220> FEATURE:
<223> OTHER INFORMATION: Synthetic peptide

<400> SEQUENCE: 9

Arg Thr Ser Arg Ala Thr Gln Phe Pro Asp
1               5                   10

<210> SEQ ID NO 10
<211> LENGTH: 1400
<212> TYPE: DNA
<213> ORGANISM: Homo sapiens

<400> SEQUENCE: 10

| | | | | | |
|---|---|---|---|---|---|
| gcatcccgga | cctgcggcga | ccgtcgtaca | ccatgggcct | ccacctccgc | ccctaccgtg | 60 |
| tggggctgct | cccggatggc | ctcctgttcc | tcttgctgct | gctaatgctg | ctcgcggacc | 120 |
| cagcgctccc | ggccggacgt | caccccccag | tggtgctggt | ccctggtgat | ttgggtaacc | 180 |
| aactggaagc | caagctggac | aagccgacag | tggtgcacta | cctctgctcc | aagaagaccg | 240 |
| aaagctactt | cacaatctgg | ctgaacctgg | aactgctgct | gcctgtcatc | attgactgct | 300 |
| ggattgacaa | tatcaggctg | gtttacaaca | aaacatccag | ggccacccag | tttcctgatg | 360 |
| gtgtggatgt | acgtgtccct | ggctttggga | agaccttctc | actggagttc | ctgaccccca | 420 |
| gcaaaagcag | cgtgggttcc | tatttccaca | ccatggtgga | gagccttgtg | ggctggggct | 480 |
| acacacgggg | tgaggatgtc | cgaggggctc | cctatgactg | cgccgagcc | ccaaatgaaa | 540 |
| acgggcccta | cttcctggcc | ctccgcgaga | tgatcgagga | gatgtaccag | ctgtatgggg | 600 |
| ccccgtggt | gctggttgcc | cacagtatgg | caacatgta | cacgctctac | tttctgcagc | 660 |
| ggcagccgca | ggcctggaag | acaagtata | tccgggcctt | cgtgtcactg | ggtgcgccct | 720 |
| gggggggcgt | ggccaagacc | ctgcgcgtcc | tggcttcagg | agacaacaac | cggatcccag | 780 |
| tcatcgggcc | cctgaagatc | cgggagcagc | agcggtcagc | tgtctccacc | agctggctgc | 840 |
| tgccctacaa | ctacacatgg | tcacctgaga | aggtgttcgt | gcagacaccc | acaatcaact | 900 |
| acacactgcg | ggactaccgc | aagttcttcc | aggacatcgg | ctttgaagat | ggctggctca | 960 |
| tgcggcagga | cacagaaggg | ctggtggaag | ccacgatgcc | acctggcgtg | cagctgcact | 1020 |
| gcctctatgg | cactggcgtc | cccacaccag | actccttcta | ctatgagagc | ttccctgacc | 1080 |
| gtgaccctaa | aatctgcttt | ggtgacggcg | atggtactgt | gaacttgaag | agtgccctgc | 1140 |
| agtgccaggc | ctggcagagc | cgccaggagc | caagtgtt | gctgcaggag | ctgccaggca | 1200 |
| gcgagcacat | cgagatgctg | ccaacgcca | ccaccctggc | ctatctgaaa | cgtgtgctcc | 1260 |
| ttgggccctg | actcctgtgc | cacaggactc | ctgtggctcg | gccgtggacc | tgctgttggc | 1320 |
| ctctggggct | gtcatggccc | acgcgttttg | caaagtttgt | gactcaccat | tcaaggcccc | 1380 |
| gagtcttgga | ctgtgaagca | | | | | 1400 |

<210> SEQ ID NO 11
<211> LENGTH: 412
<212> TYPE: PRT
<213> ORGANISM: Homo sapiens

<400> SEQUENCE: 11

Met Gly Leu His Leu Arg Pro Tyr Arg Val Gly Leu Leu Pro Asp Gly

```
              1               5              10              15
Leu Leu Phe Leu Leu Leu Leu Met Leu Leu Ala Asp Pro Ala Leu
                20              25              30
Pro Ala Gly Arg His Pro Val Val Leu Val Pro Gly Asp Leu Gly
                35              40              45
Asn Gln Leu Glu Ala Lys Leu Asp Lys Pro Thr Val His Tyr Leu
        50              55              60
Cys Ser Lys Lys Thr Glu Ser Tyr Phe Thr Ile Trp Leu Asn Leu Glu
65              70              75              80
Leu Leu Leu Pro Val Ile Ile Asp Cys Trp Ile Asp Asn Ile Arg Leu
                85              90              95
Val Tyr Asn Lys Thr Ser Arg Ala Thr Gln Phe Pro Asp Gly Val Asp
            100             105             110
Val Arg Val Pro Gly Phe Gly Lys Thr Phe Ser Leu Glu Phe Leu Asp
            115             120             125
Pro Ser Lys Ser Ser Val Gly Ser Tyr Phe His Thr Met Val Glu Ser
        130             135             140
Leu Val Gly Trp Gly Tyr Thr Arg Gly Glu Asp Val Arg Gly Ala Pro
145             150             155             160
Tyr Asp Trp Arg Arg Ala Pro Asn Glu Asn Gly Pro Tyr Phe Leu Ala
                165             170             175
Leu Arg Glu Met Ile Glu Met Tyr Gln Leu Tyr Gly Gly Pro Val
            180             185             190
Val Leu Val Ala His Ser Met Gly Asn Met Tyr Thr Leu Tyr Phe Leu
            195             200             205
Gln Arg Gln Pro Gln Ala Trp Lys Asp Lys Tyr Ile Arg Ala Phe Val
        210             215             220
Ser Leu Gly Ala Pro Trp Gly Gly Val Ala Lys Thr Leu Arg Val Leu
225             230             235             240
Ala Ser Gly Asp Asn Asn Arg Ile Pro Val Ile Gly Pro Leu Lys Ile
                245             250             255
Arg Glu Gln Gln Arg Ser Ala Val Ser Thr Ser Trp Leu Leu Pro Tyr
            260             265             270
Asn Tyr Thr Trp Ser Pro Glu Lys Val Phe Val Gln Thr Pro Thr Ile
        275             280             285
Asn Tyr Thr Leu Arg Asp Tyr Arg Lys Phe Phe Gln Asp Ile Gly Phe
        290             295             300
Glu Asp Gly Trp Leu Met Arg Gln Asp Thr Glu Gly Leu Val Glu Ala
305             310             315             320
Thr Met Pro Pro Gly Val Gln Leu His Cys Leu Tyr Gly Thr Gly Val
            325             330             335
Pro Thr Pro Asp Ser Phe Tyr Tyr Glu Ser Phe Pro Asp Arg Asp Pro
            340             345             350
Lys Ile Cys Phe Gly Asp Gly Asp Gly Thr Val Asn Leu Lys Ser Ala
        355             360             365
Leu Gln Cys Gln Ala Trp Gln Ser Arg Gln Glu His Gln Val Leu Leu
    370             375             380
Gln Glu Leu Pro Gly Ser Glu His Ile Glu Met Leu Ala Asn Ala Thr
385             390             395             400
Thr Leu Ala Tyr Leu Lys Arg Val Leu Leu Gly Pro
            405             410

<210> SEQ ID NO 12
```

<211> LENGTH: 1236
<212> TYPE: DNA
<213> ORGANISM: Mus musculus

<400> SEQUENCE: 12

```
atggatcgcc atctctgcac ctgtcgcgag acccagctcc ggagtggcct cctgttacct      60
ctgtttctac taatgatgct ggcagacctg acgctcccgg cccaacgtca ccccccggtg     120
gtgctggtgc ctggtgattt gggtaaccag ttggaagcaa agctggataa gccaaaggtt     180
gtacactacc tttgctccaa gaagacggac agctacttca cactctggct gaatctggaa     240
ctgcttctgc ctgttatcat tgactgctgg attgacaata tcaggctggt ttacaacaga     300
acatctcggg ccacccagtt tcccgatggt gtggacgtgc gtgtccctgg ctttggggaa     360
acattttcta tggaattcct agaccccagc aagaggaatg tgggttccta tttctacact     420
atggtggaga gccttgtggg ctggggctac acacggggtg aagacgttcg aggtgctccc     480
tatgattggc ggcgagcccc aaatgaaaac gggccctact tcttggccct gcgagagatg     540
atcgaggaga tgtaccagat gtatgggggc cccgtggtgc tggtcgccca gcatgggc      600
aacgtgtaca tgctctactt tctgcagcgg cagccacaag tctggaagga caaatatatc     660
catgccttcg tctcactggg ggcgccctgg ggggcgtgg ccaagacgct gcgtgtcctg      720
gcctcaggag acaacaatcg cattcccgtc attgggccac tgaagatccg ggaacagcag     780
cgatctgccg tctctaccag ctggctactg ccatacaacc acacttggtc acatgaaaag     840
gtatttgtat acacacccac gactaactac acgctccggg actatcaccg gttcttccgg     900
gacatcggtt tcgaagatgg ctggttcatg cggcaggaca cagaagggct ggttgaagcc     960
atgacgccac ccggggtgga gctgcactgc ttgtatggca ctggtgttcc cacgccaaac    1020
tctttctact acgagagctt tcctgatcgg daccccaaaa tctgcttcgg cgatggtgac    1080
ggcacggtga acctggagag cgtcctgcag tgccaagcct ggcagagccg ccaagagcac    1140
agagtatcat tgcaggagct gccgggaagc gagcacattg agatgctagc caatgccacc    1200
accttggctt atctgaaacg tgtgcttctg gaacct                              1236
```

<210> SEQ ID NO 13
<211> LENGTH: 412
<212> TYPE: PRT
<213> ORGANISM: Mus musculus

<400> SEQUENCE: 13

Met Asp Arg His Leu Cys Thr Cys Arg Glu Thr Gln Leu Arg Ser Gly
1               5                  10                  15

Leu Leu Leu Pro Leu Phe Leu Leu Met Met Leu Ala Asp Leu Thr Leu
            20                  25                  30

Pro Ala Gln Arg His Pro Pro Val Val Leu Val Pro Gly Asp Leu Gly
        35                  40                  45

Asn Gln Leu Glu Ala Lys Leu Asp Lys Pro Lys Val Val His Tyr Leu
    50                  55                  60

Cys Ser Lys Lys Thr Asp Ser Tyr Phe Thr Leu Trp Leu Asn Leu Glu
65                  70                  75                  80

Leu Leu Leu Pro Val Ile Ile Asp Cys Trp Ile Asp Asn Ile Arg Leu
                85                  90                  95

Val Tyr Asn Arg Thr Ser Arg Ala Thr Gln Phe Pro Asp Gly Val Asp
            100                 105                 110

Val Arg Val Pro Gly Phe Gly Glu Thr Phe Ser Met Glu Phe Leu Asp
        115                 120                 125

Pro Ser Lys Arg Asn Val Gly Ser Tyr Phe Tyr Thr Met Val Glu Ser
130                 135                 140

Leu Val Gly Trp Gly Tyr Thr Arg Gly Glu Asp Val Arg Gly Ala Pro
145                 150                 155                 160

Tyr Asp Trp Arg Arg Ala Pro Asn Glu Asn Gly Pro Tyr Phe Leu Ala
                165                 170                 175

Leu Arg Glu Met Ile Glu Glu Met Tyr Gln Met Tyr Gly Gly Pro Val
                180                 185                 190

Val Leu Val Ala His Ser Met Gly Asn Val Tyr Met Leu Tyr Phe Leu
                195                 200                 205

Gln Arg Gln Pro Gln Val Trp Lys Asp Lys Tyr Ile His Ala Phe Val
210                 215                 220

Ser Leu Gly Ala Pro Trp Gly Gly Val Ala Lys Thr Leu Arg Val Leu
225                 230                 235                 240

Ala Ser Gly Asp Asn Asn Arg Ile Pro Val Ile Gly Pro Leu Lys Ile
                245                 250                 255

Arg Glu Gln Gln Arg Ser Ala Val Ser Thr Ser Trp Leu Leu Pro Tyr
                260                 265                 270

Asn His Thr Trp Ser His Glu Lys Val Phe Val Tyr Thr Pro Thr Thr
                275                 280                 285

Asn Tyr Thr Leu Arg Asp Tyr His Arg Phe Phe Arg Asp Ile Gly Phe
                290                 295                 300

Glu Asp Gly Trp Phe Met Arg Gln Asp Thr Glu Gly Leu Val Glu Ala
305                 310                 315                 320

Met Thr Pro Pro Gly Val Glu Leu His Cys Leu Tyr Gly Thr Gly Val
                325                 330                 335

Pro Thr Pro Asn Ser Phe Tyr Tyr Glu Ser Phe Pro Asp Arg Asp Pro
                340                 345                 350

Lys Ile Cys Phe Gly Asp Gly Asp Gly Thr Val Asn Leu Glu Ser Val
                355                 360                 365

Leu Gln Cys Gln Ala Trp Gln Ser Arg Gln Glu His Arg Val Ser Leu
370                 375                 380

Gln Glu Leu Pro Gly Ser Glu His Ile Glu Met Leu Ala Asn Ala Thr
385                 390                 395                 400

Thr Leu Ala Tyr Leu Lys Arg Val Leu Leu Glu Pro
                405                 410

<210> SEQ ID NO 14
<211> LENGTH: 22
<212> TYPE: DNA
<213> ORGANISM: Artificial sequence
<220> FEATURE:
<223> OTHER INFORMATION: Synthetic primer

<400> SEQUENCE: 14
cagggtagct cacaactctt tg                                              22

<210> SEQ ID NO 15
<211> LENGTH: 24
<212> TYPE: DNA
<213> ORGANISM: Artificial sequence
<220> FEATURE:
<223> OTHER INFORMATION: Synthetic primer

<400> SEQUENCE: 15
caaagctctg gactgttttc ctgc                                            24

```
<210> SEQ ID NO 16
<211> LENGTH: 30
<212> TYPE: DNA
<213> ORGANISM: Artificial sequence
<220> FEATURE:
<223> OTHER INFORMATION: Synthetic primer

<400> SEQUENCE: 16
gaattcctag accccagcaa gaagaatgtg                                        30

<210> SEQ ID NO 17
<211> LENGTH: 22
<212> TYPE: DNA
<213> ORGANISM: Artificial sequence
<220> FEATURE:
<223> OTHER INFORMATION: Synthetic primer

<400> SEQUENCE: 17
ccctccccag agatggatat tt                                                22

<210> SEQ ID NO 18
<211> LENGTH: 15
<212> TYPE: DNA
<213> ORGANISM: Artificial sequence
<220> FEATURE:
<223> OTHER INFORMATION: Synthetic primer

<400> SEQUENCE: 18
atggatcgcc atctc                                                        15

<210> SEQ ID NO 19
<211> LENGTH: 24
<212> TYPE: DNA
<213> ORGANISM: Artificial sequence
<220> FEATURE:
<223> OTHER INFORMATION: Synthetic primer

<400> SEQUENCE: 19
tcaaggttcc agaagcacac gttt                                              24
```